United States Patent
Liu et al.

(10) Patent No.: US 11,591,325 B2
(45) Date of Patent: Feb. 28, 2023

(54) 2-POLYSUBSTITUTED AROMATIC RING-PYRIMIDINE DERIVATIVES, PREPARATION AND MEDICAL APPLICATION THEREOF

(71) Applicants: ZHEJIANG UNIVERSITY, Zhejiang (CN); SHANGHAI INSTITUTE OF MATERIA MEDICA, CHINESE ACADEMY OF SCIENCES, Shanghai (CN)

(72) Inventors: Tao Liu, Zhejiang (CN); Jia Li, Shanghai (CN); Yongzhou Hu, Zhejiang (CN); Yubo Zhou, Shanghai (CN); Xiaowu Dong, Zhejiang (CN); Anhui Gao, Shanghai (CN); Pinrao Song, Zhejiang (CN); Peipei Wang, Shanghai (CN); Lexian Tong, Zhejiang (CN); Xiaobei Hu, Shanghai (CN); Mingbo Su, Shanghai (CN)

(73) Assignees: ZHEJIANG UNIVERSITY, Zhejiang (CN); SHANGHAI INSTITUTE OF MATERIA MEDICA, CHINESE ACADEMY OF SCIENCES, Shhanghai (CN)

( * ) Notice: Subject to any disclaimer, the term of this patent is extended or adjusted under 35 U.S.C. 154(b) by 706 days.

(21) Appl. No.: 16/348,499

(22) PCT Filed: Nov. 8, 2017

(86) PCT No.: PCT/CN2017/110029
§ 371 (c)(1),
(2) Date: May 9, 2019

(87) PCT Pub. No.: WO2018/086546
PCT Pub. Date: May 17, 2018

(65) Prior Publication Data
US 2021/0284625 A1  Sep. 16, 2021

(30) Foreign Application Priority Data
Nov. 10, 2016 (CN) .......................... 201610988036.4

(51) Int. Cl.
| | |
|---|---|
| *C07D 413/14* | (2006.01) |
| *A61P 35/02* | (2006.01) |
| *A61P 35/00* | (2006.01) |
| *C07D 401/14* | (2006.01) |
| *C07D 405/14* | (2006.01) |
| *C07D 409/14* | (2006.01) |
| *C07D 417/14* | (2006.01) |

(52) U.S. Cl.
CPC ............ *C07D 413/14* (2013.01); *A61P 35/00* (2018.01); *A61P 35/02* (2018.01); *C07D 401/14* (2013.01); *C07D 405/14* (2013.01); *C07D 409/14* (2013.01); *C07D 417/14* (2013.01)

(58) Field of Classification Search
CPC .. C07D 401/14; C07D 405/14; C07D 409/14; C07D 413/14; C07D 417/14
See application file for complete search history.

(56) References Cited

U.S. PATENT DOCUMENTS

| | | | | |
|---|---|---|---|---|
| 2009/0093486 | A1* | 4/2009 | Niyaz .................. | C07D 251/46 544/321 |
| 2011/0237612 | A1* | 9/2011 | Greul ..................... | A01N 43/54 514/275 |
| 2012/0157427 | A1* | 6/2012 | Baker-Glenn ....... | C07D 405/14 514/210.2 |
| 2017/0029413 | A1* | 2/2017 | Holladay ............. | A61K 31/506 |

* cited by examiner

Primary Examiner — Matthew P Coughlin

(57) ABSTRACT

The present invention provides a 2-polysubstituted aromatic ring-pyrimidine derivative and an optical isomer thereof, or a pharmaceutically acceptable salt or solvate thereof, the compound, and an optical isomer thereof or a pharmaceutically thereof acceptable salts or solvates can be used in the preparation of anti-tumor drugs. The invention designs and synthesizes a series of novel small molecule Chk1 inhibitors by using N-substituted pyridin-2-aminopyrimidine obtained by structure-based virtual screening as a lead compound, and carries out Chk1 kinase inhibitory activity test. The experiment confirmed that said compounds possess potent anticancer activity, Chk1 kinase inhibitory activity, and are promising Chk1 inhibitors, and can be used as new cancer therapeutic drugs, which can be applied to treat solid tumors or hematologic tumors related to proliferative disease of human or animal. The 2-polysubstituted aromatic ring-pyrimidine derivatives provided by the present invention has the structure of the formula I:

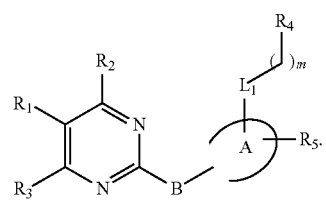

1 Claim, 1 Drawing Sheet

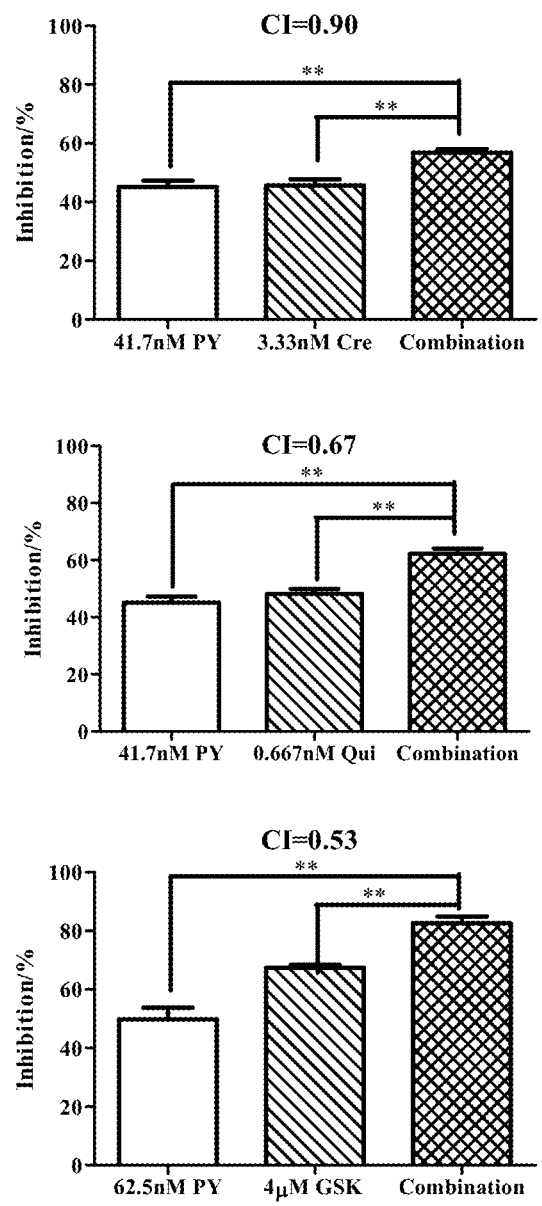

2-POLYSUBSTITUTED AROMATIC RING-PYRIMIDINE DERIVATIVES, PREPARATION AND MEDICAL APPLICATION THEREOF

CROSS REFERENCE OF RELATED APPLICATION

This is a U.S. National Stage under 35 U.S.C 371 of the International Application PCT/CN2017/110029, filed Nov. 8, 2017, which claims priority under 35 U.S.C. 119(a-d) to CN 201610988036.4, filed Nov. 10, 2016.

BACKGROUND OF THE PRESENT INVENTION

Field of Invention

The present invention relates to the field of medicine, and more particularly to a 2-polysubstituted aromatic ring-pyrimidine derivative and an optical isomer thereof, or a pharmaceutically acceptable salt or solvate thereof, a pharmaceutical composition therewith and the same in the field of antitumor applications.

Description of Related Arts

With the changes in human living environment and the aging of the population, malignant tumors are seriously threatening human life. In China, malignant tumors have become the first deadly disease. Traditional cancer treatment methods include surgery, radiation therapy and drug chemotherapy, among which drug chemotherapy is the most important. In recent years, as tumor molecular targets have been gradually explained, many targeted anti-tumor drugs have entered clinical applications, but due to the complexity of the tumors and genetic diversity, single-targeted drugs are not enough to cure tumors. Traditional chemotherapeutic drugs are mostly DNA-damaging drugs, which induce tumor cell apoptosis by directly interfering with DNA synthesis of tumor cells, regulating DNA transcription and repair, and prolonging the survival of cancer patients. However, due to its poor selectivity, it can cause a variety of toxic side effects, and it will produce significant drug resistance during the treatment. Therefore, according to the action characteristics of DNA-damaging drugs, drugs with low toxicity are developed to be combined with DNA-damaging drugs, which can reduce the therapeutic effect of DNA-damaging drugs while reducing the toxic side effects and more risk of drug resistance. Among them, the development of cell cycle-related drugs and their strategies in combination with DNA-damaging drugs have attracted great interest and attention from drug researchers in recent years.

Eukaryotic cells have their own regulatory mechanisms. When exposed to external stimuli such as radiotherapy or chemotherapy, it can be temporarily blocked in the G1, S or G2/M phase for DNA repair, and after completion of the repair, it will enter the next phase. A large number of protein kinases in cells interact with the same or different signaling pathways, forming an intricate signal network that regulates cell growth, proliferation, angiogenesis, metastasis, apoptosis and other life activities. Among them, the tumor gene suppressor protein p53 is mainly responsible for the regulation of the G1 checkpoint, while the S and G2/M phases are mainly regulated by the cell cycle checkpoint kinase 1 (Checkpoint kinase 1). Most tumor cells rely more on S or G2/M phase arrest due to the loss of p53 function as a defense mechanism for DNA damage-induced apoptosis. In the p53-deficient tumor cells, inhibition of Chk1 protein can abrogate cell cycle arrest and directly induce tumor cell apoptosis, while normal cells are temporarily blocked in G1 phase due to the existence of intact p53 regulatory mechanism. Therefore, Chk1 inhibitor can be used as an adjuvant therapy to selectively enhance the sensitivity of tumor cells to radiotherapy or chemotherapy and improve the therapeutic effect.

In addition, in the context of specific genetic defects, such as the inherent DNA damage is too high to cause large replication pressure, Chk1 inhibitors can also be used alone, killing tumor cells through a "synthetic lethal" mechanism to achieve therapeutic purpose. Based on this therapeutic strategy, Chk1 inhibitors can be used alone in the treatment of B-cell lymphoma, leukemia, neuroblastoma, and some sensitive tumors with high expression of proto-oncogenes such as breast and lung cancer.

In the past two decades, small molecular compounds of different structural types have been discovered as Chk1 inhibitors, and these compounds have shown strong anti-tumor effects in preclinical evaluation. At present, 11 small molecule Chk1 inhibitors have entered clinical research, which proves the correctness of Chk1 as a tumor treatment target.

SUMMARY OF THE PRESENT INVENTION

An object of the present invention is to provide a 2-polysubstituted aromatic ring-pyrimidine derivative and an optical isomer thereof, or a pharmaceutically acceptable salt or solvate thereof. It is a novel 2-polysubstituted aromatic ring-pyrimidine derivative with strong anticancer activity and Chk1 inhibition.

The 2-polysubstituted aromatic ring-pyrimidine derivatives provided by the present invention comprise the structure of the general formula (I):

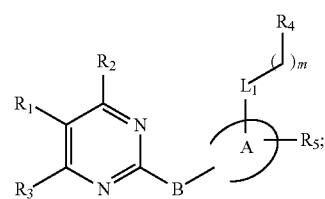

and an optical isomer thereof or a pharmaceutically acceptable salt or solvate thereof;

wherein ring A is selected from substituted or unsubstituted five- or six-membered aryl groups, and contains from 1 to 3 five- or six-membered heterocyclic aryl groups selected from O, N and S, the substituted substituents being selected from

and $R_5$; wherein ring A is preferably a 5 to 6-membered nitrogen-containing aromatic heterocyclic ring:

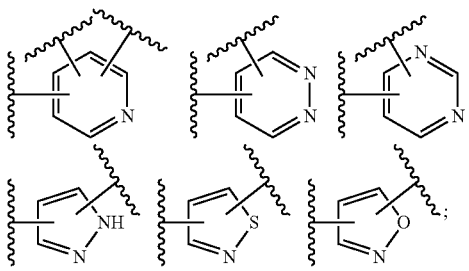

B is selected from —NH,

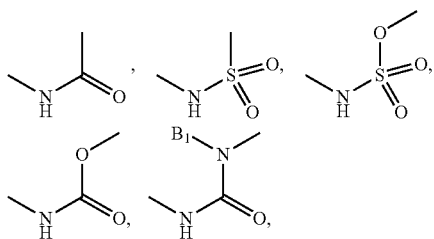

wherein B₁ is from H, $C_{1-4}$ alkyl, halogenated $C_{1-4}$ alkyl, $C_{1-4}$ alkoxy, halogenated $C_{1-4}$ alkoxy;

$R_1$ is selected from a halogen atom, a $C_{1-6}$ alkyl group, a halogenated $C_{1-6}$ alkyl group, a $C_{3-6}$ cycloalkyl group, a halogenated $C_{3-6}$ cycloalkyl group, a $C_{1-6}$ alkoxy group, halogenated $C_{1-6}$ alkoxy, $C_{2-6}$ alkenyl, $C_{2-6}$ hydroxy substituted alkenyl, $C_{2-6}$ alkynyl, $C_{2-6}$ hydroxy substituted alkynyl, unsubstituted or substituted 5- or 6-membered aromatic or aromatic heterocyclic ring, said aromatic heterocyclic ring comprising 1 to 3 hetero atoms selected from O, N, and S, the substitution being a mono-, di- or tri-substitution, said substituent being selected from the group consisting of Ra; The aryl or heterocyclic aryl group is preferably selected from the group consisting of a benzene ring, a furan, a thiophene, a pyrazole, a thiazole, and a pyrimidine;

Ra is selected from H, halogen, nitro, cyano, $C_{1-3}$ alkyl, halogenated $C_{1-3}$ alkyl, —C(=O)ORb, —C(=O)NHRb, —NHRb, —ORb —NHCORb; Rb is selected from H, $C_{1-3}$ alkyl, halogenated $C_{1-3}$ alkyl, $C_{1-3}$ alkoxy, halogenated $C_{1-3}$ alkoxy, $C_{1-7}$ alkylamine;

$R_2$ is selected from the group consisting of H, —NHRc, —N(Rc)₂, —ORc, —SRc; Rc is selected from the group consisting of $C_{1-7}$ alkyl, halogenated $C_{1-7}$ alkyl, $C_{1-7}$ hydroxyalkyl, $C_{1-7}$ aminoalkyl;

$R_3$ is selected from the group consisting of halogen, nitro, cyano, $C_{1-3}$ alkyl, halogenated $C_{1-3}$ alkyl, $C_{1-3}$ alkoxy, halogenated $C_{1-3}$ alkoxy, $C_{1-3}$ alkylamino, halogenated $C_{1-3}$ alkylamino group;

$L_1$ is selected from O, S, NH or a deletion;

m=0~2;

$R_4$ is selected from $C_{1-7}$ alkyl, halogenated $C_{1-7}$ alkyl, hydroxy substituted $C_{1-7}$ alkyl, $C_{1-7}$ alkylamino, halogenated $C_{1-7}$ alkylamino, $C_{1-7}$ alkoxy, halogenated $C_{1-7}$ alkoxy group, five- to eight-membered nitrogen-containing aliphatic heterocyclic ring;

$R_5$ is selected from the group consisting of halogen, nitro, cyano, trifluoromethyl, $C_{1-3}$ alkyl, $C_{1-3}$ alkoxy, amide and substituted alkyl amide.

Preferably, the 2-polysubstituted aromatic ring-pyrimidine derivative comprises a structure of formula II:

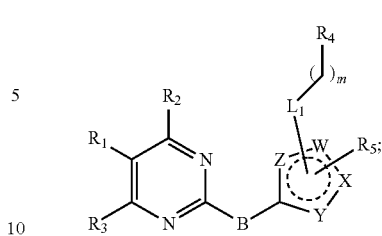

and an optical isomer thereof or a pharmaceutically acceptable salt or solvate thereof, wherein: W, X, Y and Z are identical or different and are independently selected from N, C and O;

B is selected from —NH,

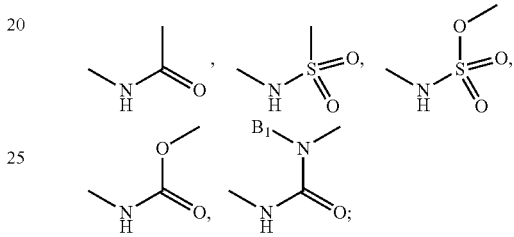

wherein B₁ is selected from the group consisting of H, $C_{1-4}$ alkyl, halogenated $C_{1-4}$ alkyl, $C_{1-4}$ alkoxy, halogenated $C_{1-4}$ alkoxy;

$R_1$ is selected from halogen atom, $C_{1-6}$ alkyl group, halogenated $C_{1-6}$ alkyl group, $C_{3-6}$ cycloalkyl group, halogenated $C_{3-6}$ cycloalkyl group, $C_{1-6}$ alkoxy group, halogenated $C_{1-6}$ alkoxy, $C_{2-6}$ alkenyl, $C_{2-6}$ hydroxy substituted alkenyl, $C_{2-6}$ alkynyl, $C_{2-6}$ hydroxy substituted alkynyl, unsubstituted or substituted 5- or 6-membered aromatic or aromatic heterocyclic ring, said aromatic heterocyclic ring comprising 1 to 3 hetero atoms selected from O, N and S, the substitution being a mono-, di- or tri-substitution, said substituent being selected from the group consisting of Ra;

Ra is selected from H, halogen, nitro, cyano, $C_{1-3}$ alkyl, halogenated $C_{1-3}$ alkyl, —C(=O)ORb, —C(=O)NHRb, —NHRb, —ORb —NHCORb; Rb is selected from H, $C_{1-3}$ alkyl, halogenated $C_{1-3}$ alkyl, $C_{1-3}$ alkoxy, halogenated $C_{1-3}$ alkoxy, $C_{1-7}$ alkylamine;

$R_2$ is selected from the group consisting of H, —NHRc, —N(Rc)₂, —ORc, —SRc; Rc is selected from the group consisting of $C_{1-7}$ alkyl, halogenated $C_{1-7}$ alkyl, $C_{1-7}$ hydroxyalkyl, $C_{1-7}$ alkylamino group, $C_{1-7}$ alkoxy group;

$R_3$ is selected from the group consisting of halogen, nitro, cyano, $C_{1-3}$ alkyl, halogenated $C_{1-3}$ alkyl, $C_{1-3}$ alkoxy, halogenated $C_{1-3}$ alkoxy, $C_{1-3}$ alkylamino, halogenated $C_{1-3}$ alkylamino group;

$L_1$ is selected from O, S, NH or a deletion;

m=0~2;

$R_4$ is selected from the group consisting of H, $C_{1-7}$ alkyl, halogenated $C_{1-7}$ alkyl, hydroxy substituted $C_{1-7}$ alkyl, $C_{1-7}$ alkylamino, halogenated $C_{1-7}$ alkylamino, $C_{1-7}$ alkoxy group, halogenated $C_{1-7}$ alkoxy group, and five- to eight-membered nitrogen-containing aliphatic heterocyclic ring;

$R_5$ is selected from the group consisting of halogen, nitro, cyano, trifluoromethyl, $C_{1-3}$ alkyl, $C_{1-3}$ alkoxy, amide, substituted alkyl amide.

Preferably, the 2-polysubstituted aromatic ring-pyrimidine derivative, comprises a structure of formula III:

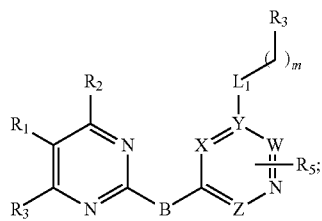

III

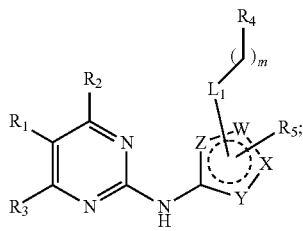

IV and an optical isomer thereof or a pharmaceutically acceptable salt or solvate thereof;

wherein W, X, Y and Z are the same or different and are each independently selected from N or C;

B is selected from —NH,

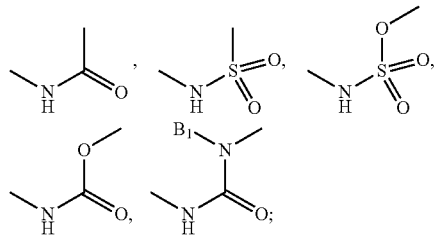

wherein $B_1$ is selected from H, $C_{1-4}$ alkyl, halogenated $C_{1-4}$ alkyl, $C_{1-4}$ alkoxy, halogenated $C_{1-4}$ alkoxy;

$R_1$ is selected from halogen atom, $C_{1-6}$ alkyl group, halogenated $C_{1-6}$ alkyl group, $C_{3-6}$ cycloalkyl group, halogenated $C_{3-6}$ cycloalkyl group, $C_{1-6}$ alkoxy group, halogenated $C_{1-6}$ alkoxy, $C_{2-6}$ alkenyl, $C_{2-6}$ hydroxy substituted alkenyl, $C_{2-6}$ alkynyl, $C_{2-6}$ hydroxy substituted alkynyl, unsubstituted or substituted 5- or 6-membered aromatic or aromatic heterocyclic ring, said aromatic heterocyclic ring comprising 1 to 3 hetero atoms selected from O, N and S, the substitution being a mono-, di- or tri-substitution, said substituent being selected from the group consisting of Ra;

$R_a$ is selected from H, halogen, nitro, cyano, $C_{1-3}$ alkyl, halogenated $C_{1-3}$ alkyl, —C(=O)ORb, —C(=O)NHRb, —NHRb, —ORb —NHCORb; Rb is selected from H, $C_{1-3}$ alkyl, halogenated $C_{1-3}$ alkyl, $C_{1-3}$ alkoxy, halogenated $C_{1-3}$ alkoxy, $C_{1-7}$ alkylamine;

$R_2$ is selected from the group consisting of H, —NHRc, —N(Rc)$_2$, —ORc, —SRc; Rc is selected from the group consisting of $C_{1-7}$ alkyl, halogenated $C_{1-7}$ alkyl, $C_{1-7}$ hydroxyalkyl, $C_{1-7}$ alkylamine group, $C_{1-7}$ alkoxy group;

$R_3$ is selected from the group consisting of halogen, nitro, cyano, $C_{1-3}$ alkyl, halogenated $C_{1-3}$ alkyl, $C_{1-3}$ alkoxy, halogenated $C_{1-3}$ alkoxy, $C_{1-3}$ alkylamino, halogenated $C_{1-3}$ alkylamino group;

$L_1$ is selected from O, S, NH or a deletion;

m=0~2;

$R_4$ is selected from the group consisting of H, $C_{1-7}$ alkyl, halogenated $C_{1-7}$ alkyl, hydroxy substituted $C_{1-7}$ alkyl, $C_{1-7}$ alkylamino, halogenated $C_{1-7}$ alkylamino, $C_{1-7}$ alkoxy group, halogenated $C_{1-7}$ alkoxy group, and five- to eight-membered nitrogen-containing aliphatic heterocyclic ring;

$R_5$ is selected from the group consisting of halogen, nitro, cyano, trifluoromethyl, $C_{1-3}$ alkyl, $C_{1-3}$ alkoxy, amide, substituted alkyl amide.

Preferably, the 2-polysubstituted aromatic ring-pyrimidine derivative comprises a structure of formula IV:

and an optical isomer thereof or a pharmaceutically acceptable salt or solvate thereof, wherein:

W, X, Y and Z are the same or different and are independently selected from N, C and O;

$R_1$ is selected from halogen atom, $C_{1-6}$ alkyl group, halogenated $C_{1-6}$ alkyl group, $C_{3-6}$ cycloalkyl group, halogenated $C_{3-6}$ cycloalkyl group, $C_{1-6}$ alkoxy group, halogenated $C_{1-6}$ alkoxy, $C_{2-6}$ alkenyl, $C_{2-6}$ hydroxy substituted alkenyl, $C_{2-6}$ alkynyl, $C_{2-6}$ hydroxy substituted alkynyl, unsubstituted or substituted 5- or 6-membered aromatic or aromatic heterocyclic ring, said aromatic heterocyclic ring comprising 1 to 3 hetero atoms selected from O, N and S, the substitution being a mono-, di- or tri-substitution, said substituent being selected from the group consisting of Ra;

$R_a$ is selected from H, halogen, nitro, cyano, $C_{1-3}$ alkyl, halogenated $C_{1-3}$ alkyl, —C(=O)ORb, —C(=O)NHRb, —NHRb, —ORb —NHCORb; Rb is selected from H, $C_{1-3}$ alkyl, halogenated $C_{1-3}$ alkyl, $C_{1-3}$ alkoxy, halogenated $C_{1-3}$ alkoxy, $C_{1-7}$ alkylamine;

$R_2$ is selected from the group consisting of H, —NHRc, —N(Rc)$_2$, —ORc, —SRc; Rc is selected from the group consisting of $C_{1-7}$ alkyl, halogenated $C_{1-7}$ alkyl, $C_{1-7}$ hydroxyalkyl, $C_{1-7}$ alkylamino group, $C_{1-7}$ alkoxy group;

$R_3$ is selected from the group consisting of halogen, nitro, cyano, $C_{1-3}$ alkyl, halogenated $C_{1-3}$ alkyl, $C_{1-3}$ alkoxy, halogenated $C_{1-3}$ alkoxy, $C_{1-3}$ alkylamino, halogenated $C_{1-3}$ alkylamino group;

$L_1$ is selected from O, S, NH or a deletion;

m=0-2;

$R_4$ is selected from the group consisting of H, $C_{1-7}$ alkyl, halogenated $C_{1-7}$ alkyl, hydroxy substituted $C_{1-7}$ alkyl, $C_{1-7}$ alkylamino, halogenated $C_{1-7}$ alkylamino, $C_{1-7}$ alkoxy group, halogenated $C_{1-7}$ alkoxy group, and five- to eight-membered nitrogen-containing aliphatic heterocyclic ring;

$R_5$ is selected from the group consisting of halogen, nitro, cyano, trifluoromethyl, $C_{1-3}$ alkyl, $C_{1-3}$ alkoxy, amide, substituted alkyl amide.

Preferably, in the 2-polysubstituted aromatic ring-pyrimidine derivative, the compound is selected from the group consisting of:

$N^4$-methyl-5-(1-methyl-1H-pyrazol-4-yl)-$N^2$-(1-methyl-5-(piperidin-4-yloxy)pyrazol-3-yl)-2,4-diaminopyrimidine;

$N^4$-methyl-5-(1-methyl-1H-pyrazol-4-yl)-$N^2$-(3-(piperidin-4-yloxy)isoxazol-5-yl)-2,4-diaminopyrimidine;

$N^4$-methyl-5-(1-methyl-1H-pyrazol-4-yl)-$N^2$-(1-methyl-2-(piperidin-4-yloxy)imidazol-4-yl)-2,4-diaminopyrimidine;

$N^4$-methyl-5-(1-methyl-1H-pyrazol-4-yl)-$N^2$-(2-(piperidin-4-yloxy)isothiazol-5-yl)-2,4-diaminopyrimidine;

$N^4$-methyl-5-(1-methyl-1H-pyrazol-4-yl)-$N^2$-(2-(piperidin-4-yloxy)-4,5-2H-oxazoline-5-yl)-2,4-diaminopyrimidine; and $N^4$-methyl-5-(1-methyl-1H-pyrazol-4-yl)-$N^2$-(2-(piperidin-4-yloxy)thiazol-5-yl)-2,4-diaminopyrimidine.

Preferably, the 2-polysubstituted aromatic ring-pyrimidine derivative, comprises a structure of formula V:

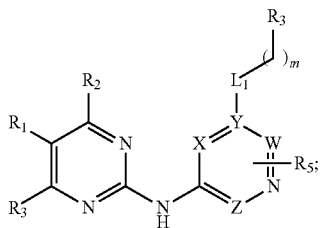

and an optical isomer thereof or a pharmaceutically acceptable salt or solvate thereof, wherein:

W, X, Y and Z are the same or different and are each independently selected from N or C;

$R_1$ is selected from halogen atom, $C_{1-6}$ alkyl group, halogenated $C_{1-6}$ alkyl group, $C_{3-6}$ cycloalkyl group, halogenated $C_{3-6}$ cycloalkyl group, $C_{1-6}$ alkoxy group, halogenated $C_{1-6}$ alkoxy, $C_{2-6}$ alkenyl, $C_{2-6}$ hydroxy substituted alkenyl, $C_{2-6}$ alkynyl, $C_{2-6}$ hydroxy substituted alkynyl, unsubstituted or substituted 5- or 6-membered aromatic or aromatic heterocyclic ring, said aromatic heterocyclic ring comprising 1 to 3 hetero atoms selected from O, N and S, the substitution being a mono-, di- or tri-substitution, said substituent being selected from the group consisting of Ra;

Ra is selected from H, halogen, nitro, cyano, $C_{1-3}$ alkyl, halogenated $C_{1-3}$ alkyl, —C(=O)ORb, —C(=O)NHRb, —NHRb, —ORb —NHCORb; Rb is selected from H, $C_{1-3}$ alkyl, halogenated $C_{1-3}$ alkyl, $C_{1-3}$ alkoxy, halogenated $C_{1-3}$ alkoxy, $C_{1-7}$ alkylamine;

$R_2$ is selected from the group consisting of H, —NHRc, —N(Rc)$_2$, —ORc, —SRc; Rc is selected from the group consisting of $C_{1-7}$ alkyl, halogenated $C_{1-7}$ alkyl, $C_{1-7}$ hydroxyalkyl, $C_{1-7}$ alkane Amino group, $C_{1-7}$ alkoxy group;

$R_3$ is selected from the group consisting of halogen, nitro, cyano, $C_{1-3}$ alkyl, halogenated $C_{1-3}$ alkyl, $C_{1-3}$ alkoxy, halogenated $C_{1-3}$ alkoxy, $C_{1-3}$ alkylamino, halogenated $C_{1-3}$ alkylamino group;

$L_1$ is selected from O, S, NH or a deletion;

m=0~2;

$R_4$ is selected from the group consisting of H, $C_{1-7}$ alkyl, halogenated $C_{1-7}$ alkyl, hydroxy substituted $C_{1-7}$ alkyl, $C_{1-7}$ alkylamino, halogenated $C_{1-7}$ alkylamino, $C_{1-7}$ alkoxy group, halogenated $C_{1-7}$ alkoxy group, and five- to eight-membered nitrogen-containing aliphatic heterocyclic ring;

$R_5$ is selected from the group consisting of halogen, nitro, cyano, trifluoromethyl, $C_{1-3}$ alkyl, $C_{1-3}$ alkoxy, amide, substituted alkyl amide.

In the 2-polysubstituted aromatic ring-pyrimidine derivative, the compound is selected from the group consisting of:
5-phenyl-N-(2-cyano-3-(piperidin-3-oxy)pyridin-5-yl)-2-aminopyrimidine;
5-(3-fluorophenyl)-N-(2-cyano-3-(piperidin-3-yloxy)pyridin-5-yl)-2-aminopyrimidine;
5-(4-fluorophenyl)-N-(2-cyano-3-(piperidin-3-yloxy)pyridin-5-yl)-2-aminopyrimidine;
5-(3-methoxyphenyl)-N-(2-cyano-3-(piperidin-3-yloxy)pyridin-5-yl)-2-aminopyrimidine;
5-(4-methoxyphenyl)-N-(2-cyano-3-(piperidin-3-yloxy)pyridin-5-yl)-2-aminopyrimidine;
5-(pyridin-3-yl)-N-(2-cyano-3-(piperidin-3-oxy)pyridin-5-yl)-2-aminopyrimidine;
5-(pyridin-4-yl)-N-(2-cyano-3-(piperidin-3-yloxy)pyridin-5-yl)-2-aminopyrimidine;
5-(thien-2-yl)-N-(2-cyano-3-(piperidin-3-yloxy)pyridin-5-yl)-2-aminopyrimidine;
5-(furan-2-yl)-N-(2-cyano-3-(piperidin-3-yloxy)pyridin-5-yl)-2-aminopyrimidine;
5-trifluoromethyl-N-(2-cyano-3-(piperidin-3-oxy)pyridin-5-yl)-2-aminopyrimidine;
(R)-5-(1-methyl-1H-pyrazol-4-yl)-N-(2-cyano-3-(piperidin-3-yloxy)pyridin-5-yl)-2-aminopyrimidine;
(S)-5-(1-methyl-1H-pyrazol-4-yl)-N-(2-cyano-3-(piperidin-3-yloxy)pyridin-5-yl)-2-aminopyrimidine;
4-methoxy-5-(3-fluorophenyl)-N-(2-cyano-3-(piperidin-4-methyl)oxypyridin-5-yl)-2-aminopyrimidine;
4-methoxy-5-(1-methyl-1H-pyrazol-4-yl)-N-(2-cyano-3-(piperidin-4-methyl)oxypyridin-5-yl)2-aminopyrimidine;
4-methoxy-5-(3-fluorophenyl)-N-(2-cyano-3-(2-dimethylaminoethoxy)pyridin-5-yl)-2-aminopyrimidine;
4-methoxy-5-(1-methyl-1H-pyrazol-4-yl)-N-(2-cyano-3-(2-dimethylaminoethoxy)pyridine-5-yl) 2-aminopyrimidine;
4-methoxy-5-trifluoromethyl-N-(2-cyano-3-(piperidin-4-methyl)oxypyridin-5-yl)-2-aminopyrimidine;
$N^4$-methyl-5-phenyl-$N^2$-(2-cyano-3-(piperidin-3-oxy)pyridin-5-yl)-2,4-diaminopyrimidine;
$N^4$-methyl-5-(3-fluorophenyl)-$N^2$-(2-cyano-3-(piperidin-3-yloxy)pyridin-5-yl)-2,4-diaminopyrimidine;
$N^4$-methyl-5-(4-fluorophenyl)-$N^2$-(2-cyano-3-(piperidin-3-yloxy)pyridin-5-yl)-2,4-diaminopyrimidine;
$N^4$-methyl-5-(2-fluorophenyl)-$N^2$-(2-cyano-3-(piperidin-3-oxy)pyridin-5-yl)-2,4-diaminopyrimidine;
$N^4$-methyl-5-(3-methoxyphenyl)-$N^2$-(2-cyano-3-(piperidin-3-yloxy)pyridin-5-yl)-2,4-diaminopyrimidine;
$N^4$-methyl-5-(4-methoxyphenyl)-$N^2$-(2-cyano-3-(piperidin-3-yloxy)pyridin-5-yl)-2,4-diaminopyrimidine;
$N^4$-methyl-5-(2,4-dimethoxyphenyl)-$N^2$-(2-cyano-3-(piperidin-3-yloxy)pyridin-5-yl)-2,4-diaminopyrimidine;
$N^4$-methyl-5-(pyridin-3-yl)-$N^2$-(2-cyano-3-(piperidin-3-yloxy)pyridin-5-yl)-2,4-diaminopyrimidine;
$N^4$-methyl-5-(pyridin-4-yl)-$N^2$-(2-cyano-3-(piperidin-3-yloxy)pyridin-5-yl)-2,4-diaminopyrimidine;
$N^4$-methyl-5-(thiophen-2-yl)-$N^2$-(2-cyano-3-(piperidin-3-oxy)pyridin-5-yl)-2,4-diaminopyrimidine;
$N^4$-methyl-5-(furan-2-yl)-$N^2$-(2-cyano-3-(piperidin-3-yloxy)pyridin-5-yl)-2,4-diaminopyrimidine;
$N^4$-methyl-5-(5-chloro-furan-2-yl)-$N^2$-(2-cyano-3-(piperidin-3-yloxy)pyridin-5-yl)-2,4-diaminopyrimidine;
$N_4$-methyl-5-(5-methoxycarbonylthiophen-2-yl)-$N^2$-(2-cyano-3-(piperidin-3-yloxy)pyridin-5-yl)-2,4-diaminopyrimidine;
$N^4$-methyl-5-(1-methyl-1H-pyrazol-4-yl)-$N^2$-(2-cyano-3-(piperidin-3-yloxy)pyridin-5-yl)-2,4-diaminopyrimidine;
$N^4$-methyl-5-(1-methyl-1H-pyrazol-5-yl)-$N^2$-(2-cyano-3-(piperidin-3-yloxy)pyridin-5-yl)-2,4-diaminopyrimidine;
$N^4$-methyl-5-trifluoromethyl-$N^2$-(2-cyano-3-(piperidin-3-oxy)pyridin-5-yl)-2,4-diaminopyrimidine;
$N^4$-methyl-5-(1-methyl-1H-pyrazol-4-yl)-$N^2$-(2-cyano-3-(piperidin-4-methyl)oxypyridin-5-yl)-2,4-diaminopyrimidine;
(R)—$N^4$-methyl-5-(1-methyl-1H-pyrazol-4-yl)-$N^2$-(2-cyano-3-(piperidin-3-yloxy)pyridine-5-yl)-2,4-diaminopyrimidine;
(S)—$N^4$-methyl-5-(1-methyl-1H-pyrazol-4-yl)-$N^2$-(2-cyano-3-(piperidin-3-yloxy)pyridine-5-yl)-2,4-diaminopyrimidine;
(R)—$N^4$-methyl-5-trifluoromethyl-$N^2$-(2-cyano-3-(piperidin-3-oxy)pyridin-5-yl)-2,4-diaminopyrimidine;

(S)—N$^4$-methyl-5-trifluoromethyl-N$^2$-(2-cyano-3-(piperidin-3-oxy)pyridin-5-yl)-2,4-diaminopyrimidine;
(R)—N$^4$-methyl-5-(1-methyl-1H-pyrazol-4-yl)-N$^2$-(2-cyano-3-(pyrrole-3-oxy)pyridin-5-yl)-2,4-diaminopyrimidine;
(S)—N$^4$-methyl-5-(1-methyl-1H-pyrazol-4-yl)-N$^2$-(2-cyano-3-(pyrrole-3-oxy)pyridin-5-yl)-2,4-diaminopyrimidine;
N$^4$-methyl-5-(1-methyl-1H-pyrazol-4-yl)-N$^2$-(2-cyano-3-(piperidin-4-yloxy)pyridin-5-yl)-2,4-diaminopyrimidine;
N$^4$-methyl-5-(1-methyl-1H-pyrazol-4-yl)-N$^2$-(2-cyano-3-(2-dimethylaminoethoxy)pyridin-5-yl)-2,4-diaminopyrimidine;
(R)—N$^4$-methyl-5-(1-methyl-1H-pyrazol-4-yl)-N$^2$-(2-cyano-3-(1-dimethylaminopropyl-2-oxy) pyridin-5-yl)-2,4-diaminopyrimidine;
(S)—N$^4$-methyl-5-(1-methyl-1H-pyrazol-4-yl)-N$^2$-(2-cyano-3-(1-dimethylaminopropyl-2-oxy) pyridin-5-yl)-2,4-diaminopyrimidine;
N$^4$-methyl-5-(1-methyl-1H-pyrazol-4-yl)-N$^2$-(2-cyano-3-(N-methylpiperidin-4-yloxy)pyridine-5-yl)2,4-diaminopyrimidine;
N$^4$-methyl-5-trifluoromethyl-N$^2$-(2-cyano-3-(N-methylpiperidin-4-yloxy)pyridin-5-yl)-2,4-diaminopyrimidine;
N$^4$-methyl-5-(4-methylthiazol-2-yl)-N$^2$-(2-cyano-3-(piperidin-3-yloxy)pyridin-5-yl)-2,4-diaminopyrimidine;
and a pharmaceutically acceptable salt or solvate thereof.

The invention adopts a method familiar to technicians in this field to prepare salt of 2-pyrimidine derivatives described in the invention. The salt may be an organic acid salt, a mineral acid salt and so on, and the organic acid salt includes a citrate, a fumarate, an oxalate, a malate, a L-malate, and a D-malate, lactate, camphorsulfonate, p-toluenesulfonate, methanesulfonate, benzoate, etc.; the inorganic acid salt includes a hydrohalide, a sulfate, a phosphate, a nitrate, and so on. For example, with a lower alkylsulfonic acid such as methanesulfonic acid, trifluoromethanesulfonic acid or the like may form a mesylate salt, a triflate salt; and an arylsulfonic acid such as benzenesulfonic acid or p-toluenesulfonic acid; with organic carboxylic acids such as acetic acid, fumaric acid, tartrate, L-tartaric acid, D-tartaric acid, oxalic acid, maleic acid, malate, L-malic acid, D-malic acid, succinic acid or citric acid and so on may form corresponding salts; and with an amino acid such as glutamic acid or aspartic acid may form a glutamate or an aspartate. Corresponding salts may also be formed with inorganic acids such as hydrohalic acids (e.g., hydrofluoric acid, hydrobromic acid, hydroiodic acid, hydrochloric acid), nitric acid, carbonic acid, sulfuric acid or phosphoric acid.

The second purpose of the invention is to provide a pharmaceutical composition comprising at least one active ingredient together with one or more pharmaceutically acceptable carriers or excipients, said active ingredient it may be a 2-substituted pyrimidine compound of the present invention, an optical isomer of the compound, a solvate of the compound or an optical isomer thereof in a pharmaceutically acceptable salt, the compound or an optical isomer thereof Any one or any of a variety of them.

The carrier includes conventional diluents, excipients, fillers, binders, wetting agents, disintegrating agents, absorption enhancers, surfactants, adsorption carriers, lubricants, etc. in the pharmaceutical field, etc. and fragrances, sweetener may also be added if necessary. The medicament of the present invention can be prepared into various forms such as tablets, powders, granules, capsules, oral liquids and injectable preparations, and the medicaments of the above respective dosage forms can be prepared according to a conventional method in the pharmaceutical field.

The present invention also provides a compound of the formula (I) to the formula (V), and an optical isomer thereof, or a pharmaceutically acceptable salt or solvate thereof, and an optical isomer thereof, or a pharmaceutically acceptable compound thereof. The use of accepted salts or solvates, alone and/or in combination with radiation therapy, other drugs, in the preparation of Chk1 inhibitors, particularly in the preparation of therapeutically proliferative diseases. The cell proliferative diseases include tumors, and the tumors are breast cancer, ovarian cancer, narcoma, lung cancer, prostate cancer, colon cancer, rectal cancer, renal cancer, pancreatic cancer, blood cancer, lymphoma, neuroblastoma, and glioma, head cancer, neck cancer, thyroid cancer, liver cancer, vulvar cancer, cervical cancer, endometrial cancer, testicular cancer, bladder cancer, esophageal cancer, stomach cancer, nasopharyngeal cancer, buccal cancer, oral cancer, gastrointestinal stromal tumor, skin cancer, multiple myeloma. The antitumor agent which can be used in combination with the compound provided by the present invention or a pharmaceutically acceptable salt intended includes, but is not limited to, at least one of the following classes: antimetabolite (gemcitabine, 5-fluorouracil, hydroxyurea, pemetrexed); bioalkylatingagengts (eg cisplatin, carboplatin); topoisomerase inhibitors (irinotecan, doxorubicin); small molecule inhibitors (MEK inhibitors, PARP inhibitors, Scr kinase inhibitors, mTOR inhibitors, farnesyltransferase inhibitors, etc.).

Another object of the present invention is to provide a process for the preparation of the above target compound by the following steps:

First Method:

(1) 5-Bromo-2-substituted-3-nitropyridine (or 5-bromo-2-cyano-3-nitropyridine) was reacted with different fatty alcohols under basic conditions (in the presence of NaH) to obtain different substituted pyridine fragments;

(2) Starting with 5-bromo-2,4-dichloropyrimidine, followed by methyl etherification or methylamination to give 5-bromo-2-chloro-4-substituted pyrimidine then was ammoniated to get 5-bromo-N$^4$-methylpyrimidine-2,4-diamine or 5-bromo-4-methoxypyrimidin-2-amine. 2-Aminopyrimidine was brominated to obtain 5-bromo-2-aminopyrimidine. The Suzuki-Miyaura coupling reaction was occurred between 5-bromo-N$^4$-methylpyrimidine-2,4-diamine or 5-bromo-4-methoxypyrimidin-2-amine or 5-bromo-2-aminopyrimidine and corresponding borate or boric acid and then Buchwald-Hartwig cross-coupling was occurred between the product of the Suzuki-Miyaura coupling reaction and the substituted pyridine fragment from the first step, followed by acidic deprotection to obtain the target compound; or 5-bromo-N$^4$-methylpyrimidine-2,4-diamine was firstly carried out Buchwald-Hartwig cross-coupling with the substituted pyridine fragment from the first step, then followed by Suzuki-Miyaura coupling reaction with corresponding borate or boric acid, and then deprotection under acidic conditions to obtain the target compound; Compound 1-6 was prepared according to the following synthetic route:

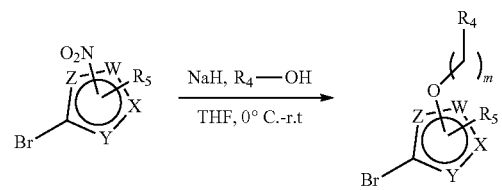

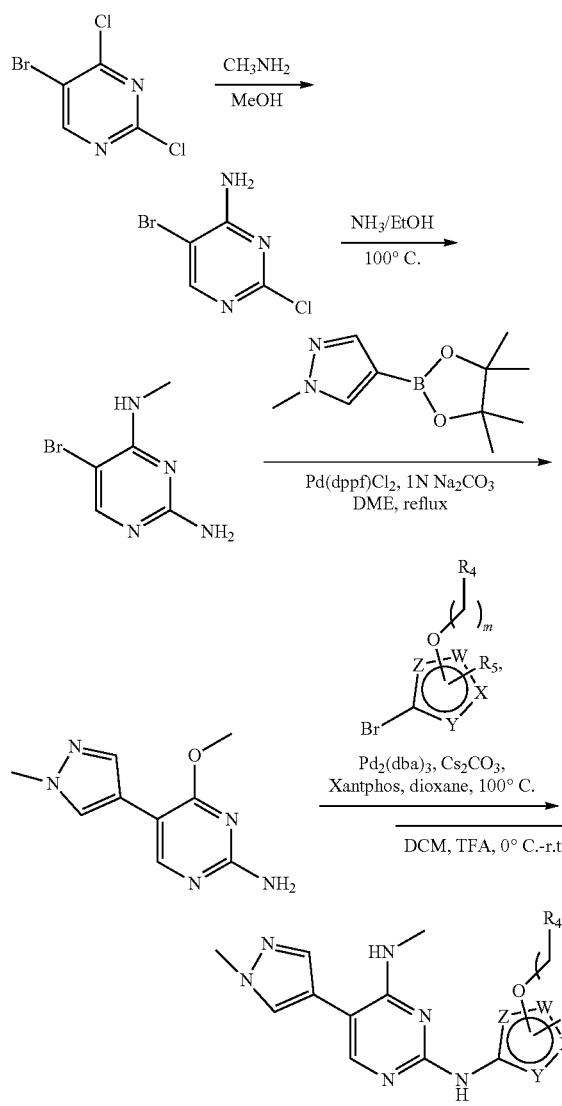
W, X, Y, Z = C/N/O
Compound 7-16 was prepared according to the following synthetic route:
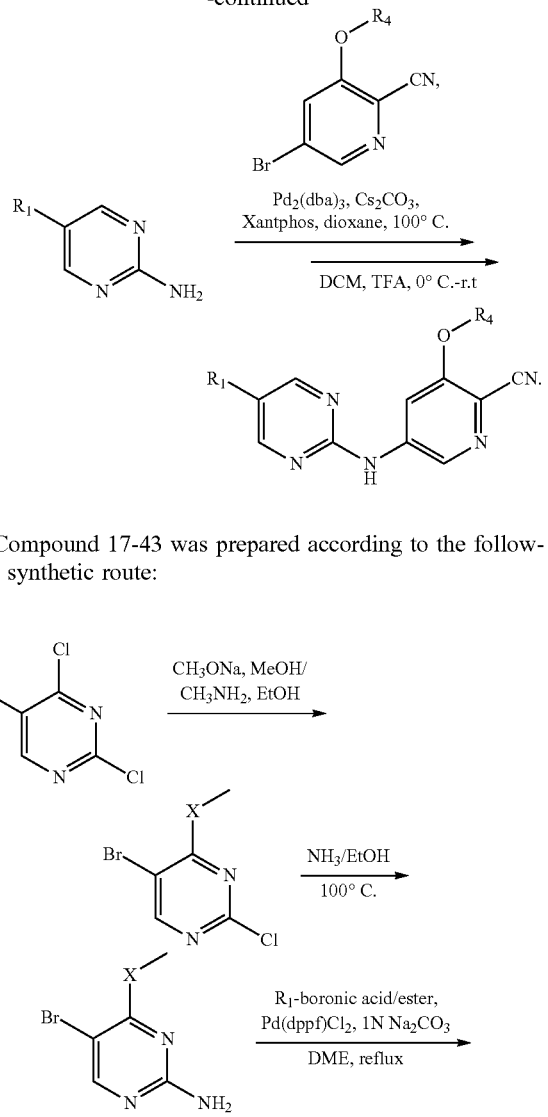
Compound 17-43 was prepared according to the following synthetic route:
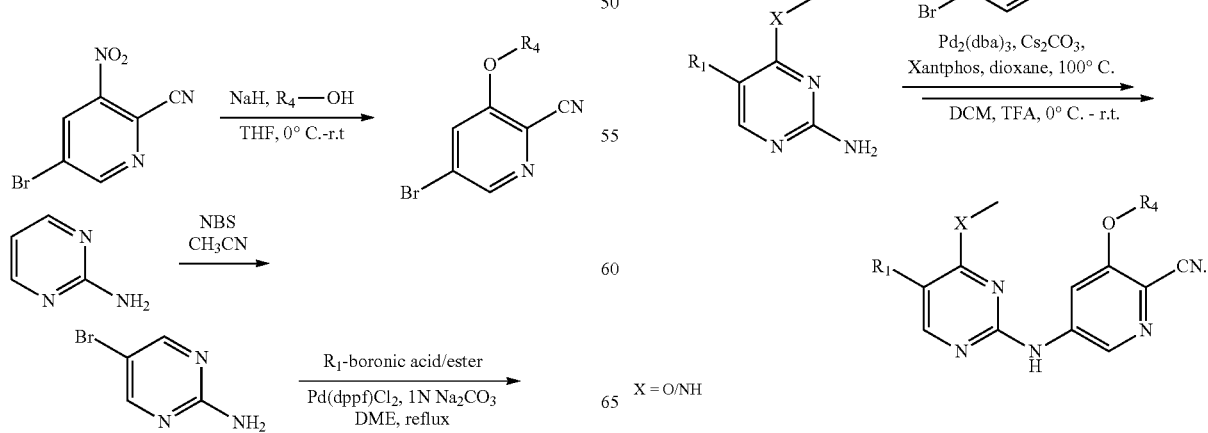
X = O/NH Compound 44 was prepared according to the following synthetic route:

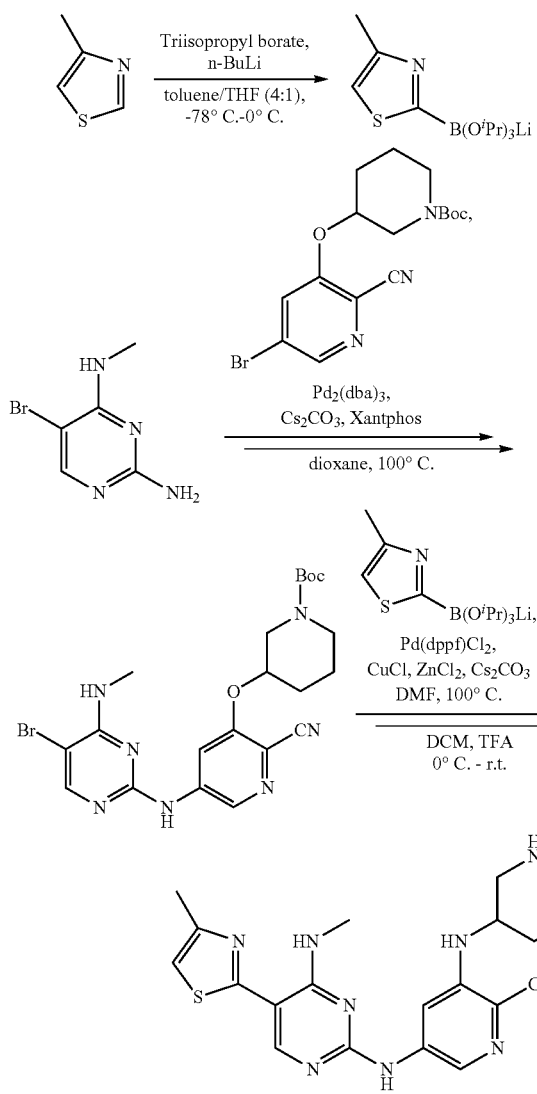

Second Method:
(1) 5-Bromo-2-cyano-3-nitropyridine was reacted with different fatty alcohols under basic conditions (conditions of NaH) to obtain different substituted pyridine fragments;
(2) 2,4-Dichloro-5-trifluoromethylpyrimidine as starting material, followed by methyl etherification or methylamination, then ammoniation to obtain 2,4-disubstituted-5-trifluoromethylpyrimidine. 2-Chloro-5-trifluoromethylpyrimidine was ammoniated to get 2-amino-5-trifluoromethylpyrimidine. Buchwal-Hartwig cross-coupling was carried out between 2,4-disubstituted-5-trifluoromethylpyrimidine or 2-amino-5-trifluoromethylpyrimidine with the substituted pyridine fragment from the first step, and finally removing the Boc protecting group to obtain the target compound.

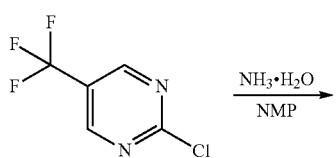

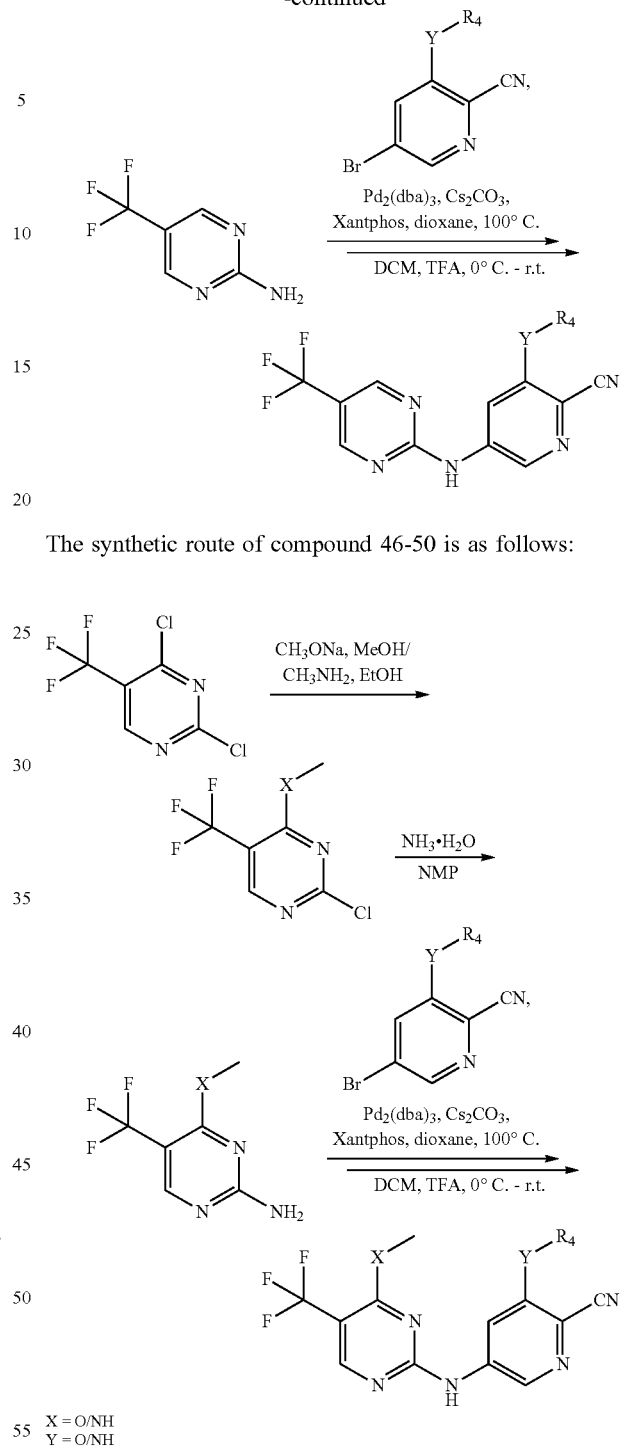

The synthetic route of compound 46-50 is as follows:

X = O/NH
Y = O/NH

The inventors of the present invention have experimentally confirmed that most of the compounds of the present invention have moderate to strong Chk1 kinase inhibitory activity and are useful for the treatment of solid tumors or blood cancers associated with cell proliferation in humans or animals. A series of novel small molecule Chk1 inhibitors were designed and synthesized by using 2-aminopyrimidine as a lead compound obtained through structure-based virtual screening, and Chk1 kinase inhibitory activity of these compounds was tested. The results showed that most of the compounds exhibited moderate to strong Chk1 inhibitory activity and were promising Chk1 inhibitors, providing new drugs for cancer therapy.

BRIEF DESCRIPTION OF THE DRAWINGS

The FIGURE is a diagram showing activity of CHK1 inhibitor combining with other drugs on MV 4-11 cell line.

DETAILED DESCRIPTION OF THE PREFERRED EMBODIMENT

Further description of the present invention was illustrated combining with the preferred embodiments. The embodiments below are exemplary only and not intended to be limiting.

Embodiment of Preparation 1

$N^4$-methyl-5-(1-methyl-1H-pyrazol-4-yl)-$N^2$-(1-methyl-5-(piperidin-4-yloxy)-pyrazol-3-yl)-2, 4-di-aminopyrimidine (Compound 1)

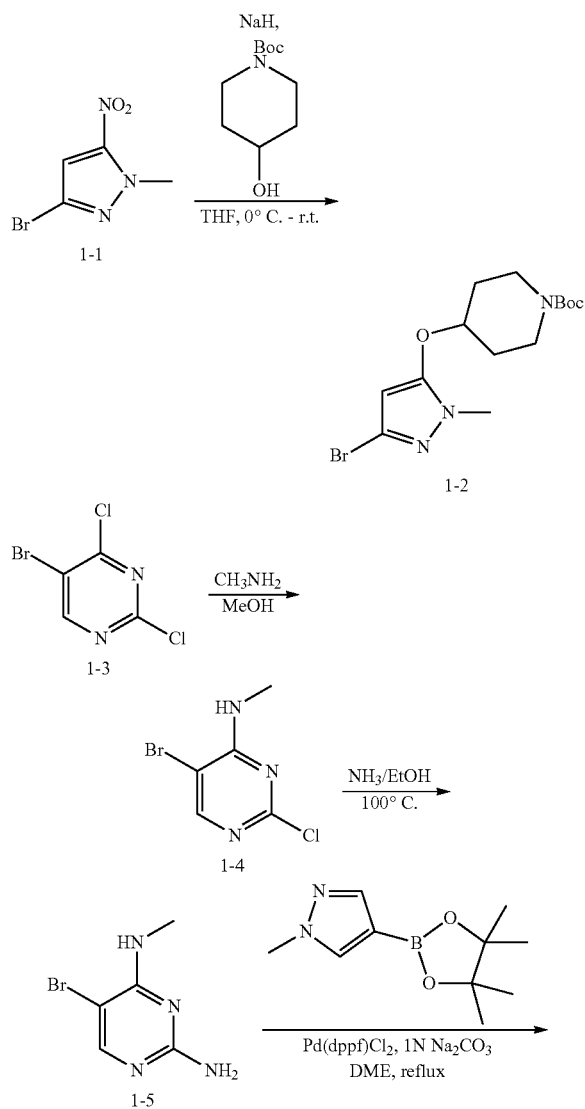

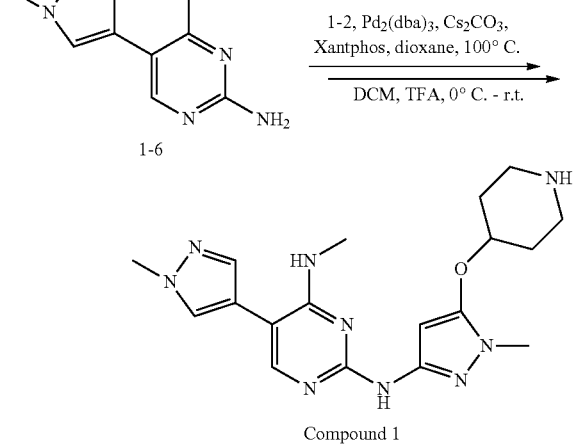

Step 1: synthesis of N-tert-butoxycarbonyl-4-((3-bromo-1-methyl-1H-pyrazol-5-yl) oxy) piperidin (Intermediate 1-2)

N-tert-Butyloxycarbonyl-4-hydroxypiperidine (460 mg, 2.29 mmol) was dissolved into anhydrous THF (7.2 mL), cooling in ice bath, adding 60% sodium hydride (108 mg, 4.5 mmol) portionwise and stirring at room temperature for 10 min; The mixture was heated to 35° C. and stirred for 10 min; Subsequently, the above sodium solution was added dropwise slowly (completed in about 20 min) to the solution of 3-bromo-1-methyl-5-nitropyrazole (360 mg, 1.75 mmol) in anhydrous THF 4.8 mL in a three-necked flask under protection of nitrogen and stirred at room temperature for 1 h. The reaction was quenched by the addition of a saturated ammonium chloride solution, and the solvent was evaporated under reduced pressure. The resultant product was purified by silica gel column chromatography eluting PE:E-tOAc (50:9) to give a yellow liquid. Yield: 79%; LCMS: m/z=361 [M+1]$^+$.

Step 2, Synthesis of 4-methylamino-2-chloro-5-bromopyrimidine (Intermediate 1-4)

To a solution of 5-bromo-2,4-dichloropyrimidine (5 g, 22 mmol) in methanol (42 mL), 33% methylamine alcohol solution (6.75 mL) was added dropwise under an ice water bath, and the reaction mixture was stirred at room temperature 30 min. The solvent was evaporated under reduced pressure and the crude product was purified by column chromatography (eluent PE:EtOAc=5:1) to give a white solid. Yield: 88%; mp: 139-141° C.; $^1$H NMR (500 MHz, DMSO-$d_6$): δ 8.85 (s, Ar—H, 1H), 7.75 (br, NH, 1H), 2.85 (d, J=3.9 Hz, $CH_3$, 3H); ESI-MS: m/z=222 $[M+1]^+$.

Step 3. Synthesis of 5-bromo-$N^4$-methyl-2,4-diaminopyrimidine (Intermediate 1-5)

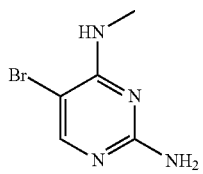

Compound 1-4 (275 mg, 1.23 mmol) was placed in a sealed tube, and a solution of ammonia-saturated ethanol (20 mL) was added and the reaction mixture was stirred at 100° C. for 24 h. After cooling to room temperature, the solvent was removed by evaporation. The residue was purified by silica gel column chromatography (eluent PE:EtOAc=2:1) to give a white solid. Yield: 78%; $^1$H NMR (500 MHz, $CDCl^3$): δ 7.86 (s, Ar—H, 1H), 5.22 (br, NH, 1H), 4.85 (br, $NH_2$, 2H), 2.99 (d, J=6.0 Hz, $CH_3$, 3H); ESI-MS: m/z=204 $[M+1]^+$.

Step 4. Synthesis of 5-(1-methyl-1H-pyrazol-4-yl)-$N^4$-methyl-2,4-diaminopyrimidine (Intermediate 1-6)

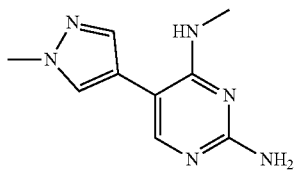

Compound 1-5 (290 mg, 1.43 mmol), 1-methyl-1H-pyrazole-4-boronic acid pinacol ester (358 mg, 1.72 mmol) and Pd(dppf)$Cl_2$ (54 mg, 0.07 mmol) were placed in reaction flask. Then ethylene glycol dimethyl ether (14 mL) and 1N aqueous $Na_2CO_3$ solution were added. The reaction was carried out under refluxing overnight. After cooling, the solvent was removed under reduced pressure. The residue was purified by column chromatography on silica gel (eluent $CH_2Cl_2$:EtOH=25:1) to give a white solid. Yield: 75%; mp: 226-228° C.; $^1$H NMR (500 MHz, DMSO-$d_6$): δ 7.88 (s, Ar—H, 1H), 7.49 (s, Ar—H, 1H), 7.35 (s, Ar—H, 1H), 6.22 (br, $NH_2$, 2H), 5.96 (q, J=4.5 Hz, NH, 1H), 3.51 (s, $CH_3$, 3H), 2.86 (d, J=4.5 Hz, $CH_3$, 3H); ESI-MS: m/z=205 $[M+1]^+$.

Step 5. Synthesis of $N^4$-methyl-5-(1-methyl-1H-pyrazol-4-yl)-$N^2$-(1-methyl-5-(piperidin-4-yloxy) pyrazol-3-yl)-2,4-diaminopyrimidine (Compound 1)

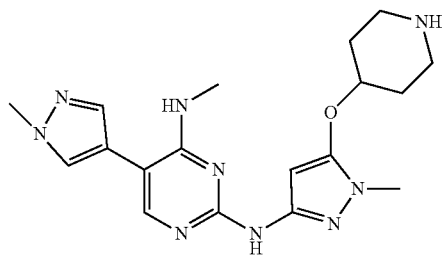 [SMILES: CNc1nc(Nc2cc(OC3CCNCC3)n(C)n2)ncc1-c1cnn(C)c1]

A mixture of compound 1-6 (169 mg, 0.986 mmol), compound 1-2 (376 mg, 0.986 mmol), tris(dibenzylideneacetone)dipalladium (9 mg, 0.00986 mmol), 4,5-bisdiphenylphosphine-9,9-dimethyloxanium (15 mg, 0.026 mmol, $Cs_2CO_3$ (450 mg, 1.38 mmol) in dry dioxane (6 mL) was heated to reflux overnight under nitrogen. The cooled reaction mixture was filtered and the filtrate was removed by evaporation. The obtained residue was purified by column chromatography on silica gel (eluent $CH_2Cl_2$:EtOH=30:1) to give a white solid. Removal of the Boc protecting group with trifluoroacetic acid gave a white solid. Yield: 65%; LCMS: m/z=385 $[M+1]^+$.

Preparative Example 2

$N^4$-Methyl-5-(1-methyl-1H-pyrazol-4-yl)-$N^2$-(3-(piperidin-4-yloxy)isoxazol-5-yl)-2,4-diaminopyrimidine (Compound 2)

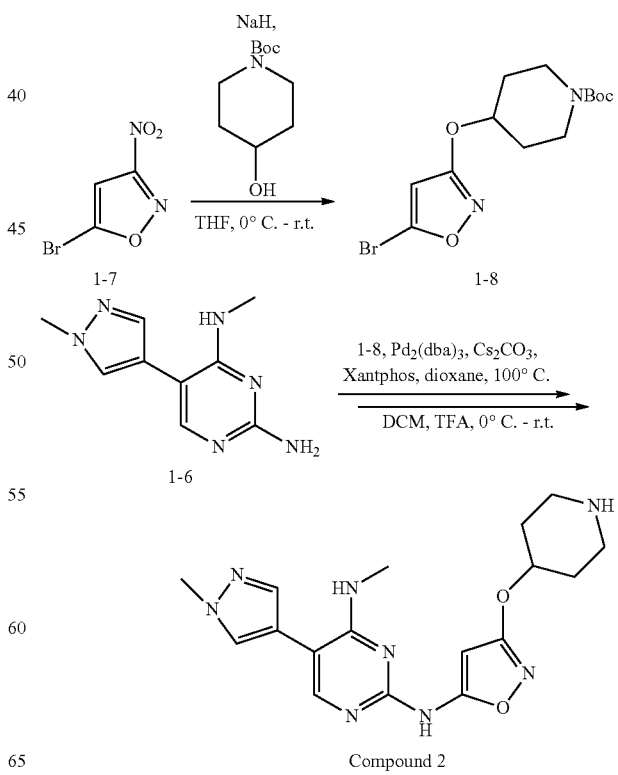

Compound 2

Step 1. Synthesis of N-tert-butoxycarbonyl-4-((5-bromo-isoxazol-3-yl)oxy)piperidine (Intermediate 1-8)

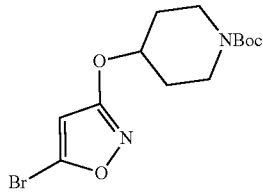 [SMILES: CC(C)(C)OC(=O)N1CCC(Oc2cc(Br)on2)CC1]

Synthetic Procedure Reference Example 1, Step 1. Compounds 1-8 were prepared from (Compound 1-7) according to the same procedure as Compound 1-2. Yield: 63%; LCMS: m/z=348 [M+1]⁺.

Step 2. N⁴-Methyl-5-(1-methyl-1H-pyrazol-4-yl)-N²-(3-(piperidin-4-yloxy)isoxazol-5-yl)-2,4-diaminopyrimidine (Compound 2)

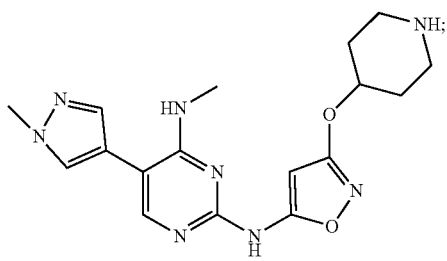 [SMILES: CNc1nc(Nc2cc(OC3CCNCC3)no2)ncc1-c1cnn(C)c1]

The synthetic procedure was carried out according to the same procedure as in PREPARATIVE EXAMPLE 1, Step 5. Compound 2 was prepared by a synthetic method similar to Compound 1, using Intermediates 1-8 and 1-6 as starting materials. Yield: 65%; LCMS: m/z=371 [M+1]⁺.

Preparative Example 3. N⁴-Methyl-5-(1-methyl-1H-pyrazol-4-yl)-N²-(1-methyl-2-(piperidin-4-yloxy)imidazol-4-yl)-2,4-diaminopyrimidine (Compound 3)

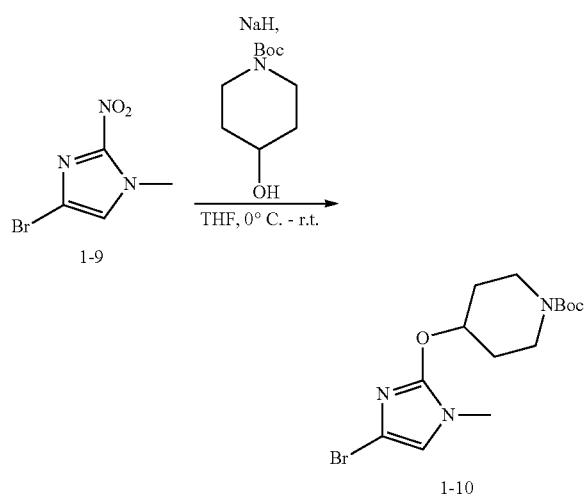

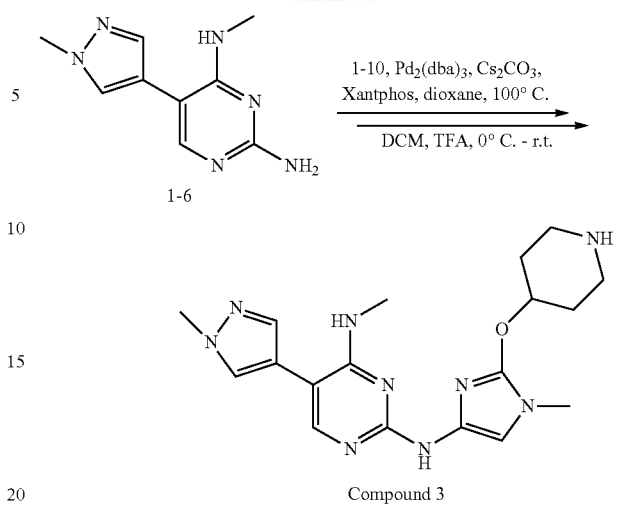

Step 1. Synthesis of N-tert-butoxycarbonyl-4-((4-bromo-1-methyl-1H-imidazol-2-yl)oxy)piperidine (Intermediate 1-10)

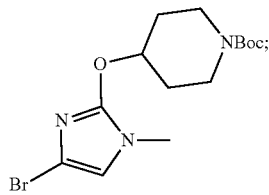 [SMILES: Cn1cc(Br)nc1OC1CCN(C(=O)OC(C)(C)C)CC1]

Synthetic Procedure Reference Example 1, Step 1. Compound 1-10 was prepared from 4-bromo-1-methyl-2-nitro-imidazole (Compound 1-9) according to the same procedure as Compound 1-2. Yield: 67%; LCMS: m/z=361 [M+1]⁺.

Step 2. N⁴-Methyl-5-(1-methyl-1H-pyrazol-4-yl)-N²-(1-methyl-2-(piperidin-3-yloxy)imidazol-4-yl)-2,4-diaminopyrimidine (Compound 3)

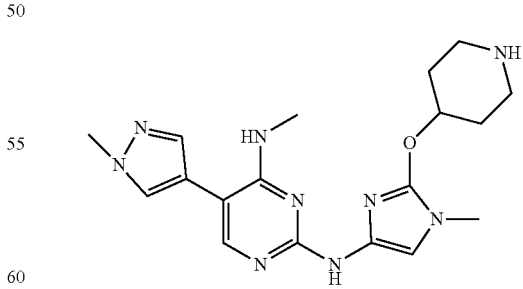

The synthetic procedure was carried out according to the same procedure as in PREPARATIVE EXAMPLE 1, Step 5. Compound 3 was prepared by a synthetic method similar to Compound 1, using Intermediates 1-10 and 1-6 as starting materials. Yield: 65%; LCMS: m/z=384 [M+1]⁺.

Preparative Example 4. N⁴-Methyl-5-(1-methyl-1H-pyrazol-4-yl)-N²-(2-(piperidin-4-yloxy)isothiazol-5-yl)-2,4-diaminopyrimidine (Compound 4)

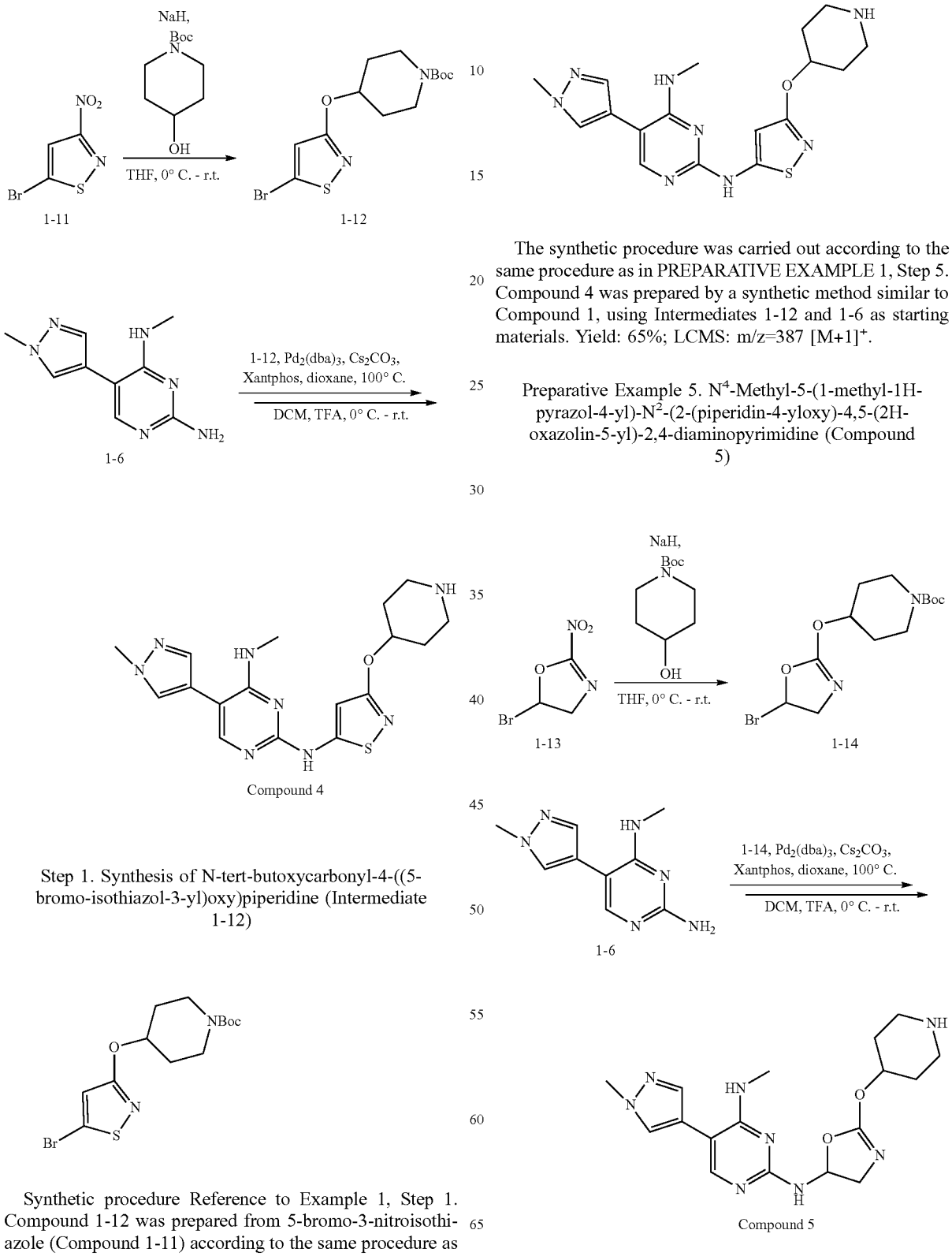

Step 1. Synthesis of N-tert-butoxycarbonyl-4-((5-bromo-isothiazol-3-yl)oxy)piperidine (Intermediate 1-12)

Synthetic procedure Reference to Example 1, Step 1. Compound 1-12 was prepared from 5-bromo-3-nitroisothiazole (Compound 1-11) according to the same procedure as Compound 1-2. Yield: 66%; LCMS: m/z=364[M+1]⁺.

Step 2. N⁴-Methyl-5-(1-methyl-1H-pyrazol-4-yl)-N²-(2-(piperidin-4-yloxy)isothiazol-5-yl)-2, 4-diaminopyrimidine (Compound 4)

The synthetic procedure was carried out according to the same procedure as in PREPARATIVE EXAMPLE 1, Step 5. Compound 4 was prepared by a synthetic method similar to Compound 1, using Intermediates 1-12 and 1-6 as starting materials. Yield: 65%; LCMS: m/z=387 [M+1]⁺.

Preparative Example 5. N⁴-Methyl-5-(1-methyl-1H-pyrazol-4-yl)-N²-(2-(piperidin-4-yloxy)-4,5-(2H-oxazolin-5-yl)-2,4-diaminopyrimidine (Compound 5)

Step 1. Synthesis of N-tert-butoxycarbonyl-4-((5-bromo-4,5-2H-oxazolin-2-yl)oxy)piperidine (Intermediate 1-14)

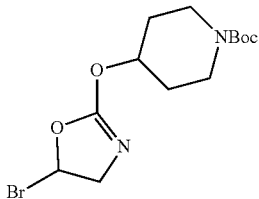 [SMILES: CC(C)(C)OC(=O)N1CCC(OC2=NCC(Br)O2)CC1]

Synthetic Procedure Reference Example 1, Step 1. Compound 1-14 was prepared from 5-bromo-2-nitro-4,5-2H-oxazoline (compound 1-13) according to the same procedure as compound 1-2. Yield: 67%; LCMS: m/z=361 [M+1]$^+$.

Step 2. N$^4$-Methyl-5-(1-methyl-1H-pyrazol-4-yl)-N$^2$-(2-(piperidin-4-yloxy)-4,5-2H-oxazolin-5-yl)-2,4-diaminopyrimidine (Compound 5)

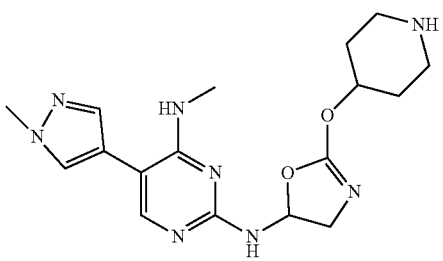 [SMILES: CNc1nc(NC2CN=C(OC3CCNCC3)O2)ncc1-c1cnn(C)c1]

The synthetic procedure was carried out according to the same procedure as in PREPARATIVE EXAMPLE 1, Step 5. Compound 5 was prepared by a synthetic method similar to Compound 1, using Intermediates 1-14 and 1-6 as starting materials. Yield: 65%; LCMS: m/z=373 [M+1]$^+$.

Preparative Example 6. N$^4$-Methyl-5-(1-methyl-1H-pyrazol-4-yl)-N$^2$-(2-(piperidin-4-yloxy)thiazol-5-yl)-2,4-diaminopyrimidine (Compound 6)

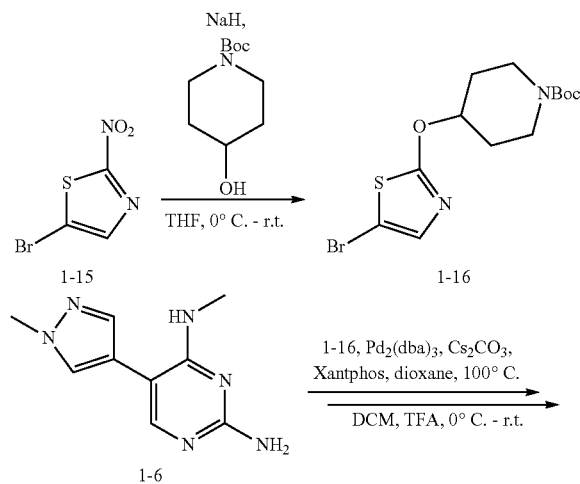

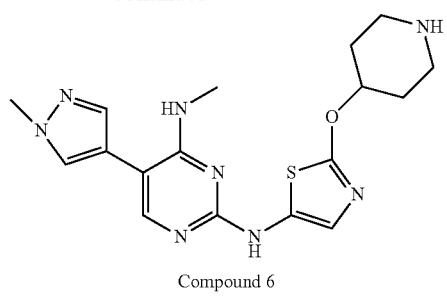

Compound 6

Step 1. Synthesis of N-tert-butoxycarbonyl-4-((5-bromo-thiazol-2-yl)oxy)piperidine (Intermediate 1-16)

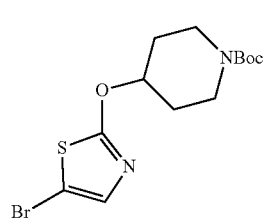 [SMILES: CC(C)(C)OC(=O)N1CCC(Oc2ncc(Br)s2)CC1]

Synthetic Procedure Reference Example 1, Step 1. Compound 1-16 was prepared from 5-bromo-2-nitrothiazole (Compound 1-15) according to the same procedure as Compound 1-2. Yield: 63%; LCMS: m/z=364 [M+1]$^+$.

Step 2. N$^4$-Methyl-5-(1-methyl-1H-thiazol4-yl)-N$^2$-(1-methyl-2-(piperidin-4-yloxy)pyrazol-4-yl)-2,4-diaminopyrimidine (Compound 6)

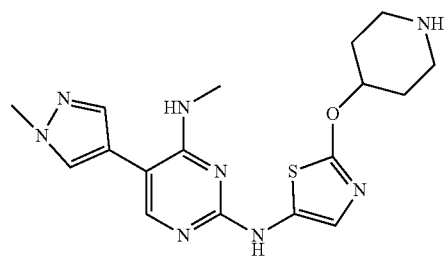 [SMILES: CNc1nc(Nc2cnc(OC3CCNCC3)s2)ncc1-c1cnn(C)c1]

The synthetic procedure was carried out according to the same procedure as in PREPARATIVE EXAMPLE 1, Step 5. Compound 6 was prepared by a synthetic method similar to Compound 1, using Intermediates 1-16 and 1-6 as starting materials. Yield: 65%; LCMS: m/z=387 [M+1]$^+$.

Preparative Example 7. 5-Phenyl-N-(2-cyano-3-(piperidin-3-oxy)pyridin-5-yl)-2-aminopyrimidine (Compound 7)

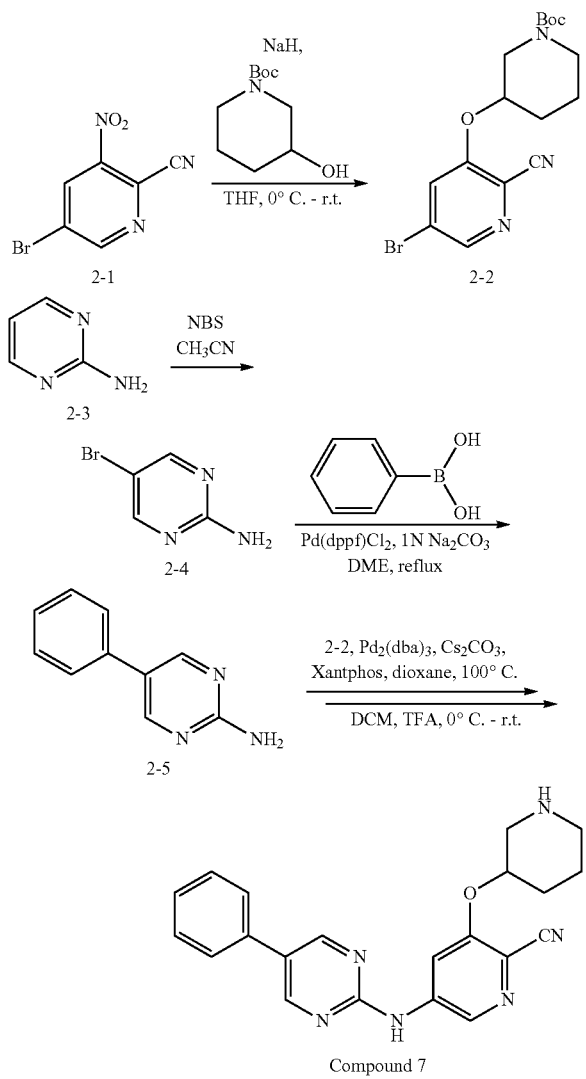

Compound 7

Step 1. Synthesis of 2-cyano-5-bromo-3-(N-tert-butoxycarbonylpiperidin-3-yloxy)pyridine (Intermediate 2-2)

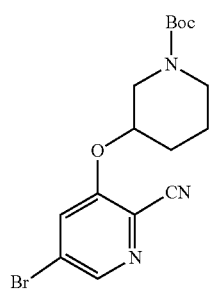 [SMILES: CC(C)(C)OC(=O)N1CCCC(Oc2cc(Br)cnc2C#N)C1]

Synthetic Procedure Reference to Example 1, Step 1. Compound 2-2 was prepared according to the same procedure as Compound 1-2, using 5-bromo-3-nitro-2-cyanopyridine (Compound 2-1) and N-tert-butoxycarbonyl-3-hydroxypiperidine as starting materials. Yield: 79%; $^1$H NMR (500 MHz, DMSO-$d_6$): δ 8.26 (s, Ar—H, 1H), 7.53 (s, Ar—H, 1H), 4.38 (br, CH, 1H), 3.63 (br, CH, 1H), 3.51 (br, CH, 1H), 3.38 (br, CH, 2H), 1.98-1.96 (m, CH, 1H), 1.91-1.85 (m, CH, 2H), 1.51 (br, CH, 1H), 1.36 (s, CH$_3$×3, 9H); ESI-MS: m/z=382 [M+1]$^+$.

Step 2. Synthesis of 5-bromo-2-aminopyrimidine (Intermediate 2-4)

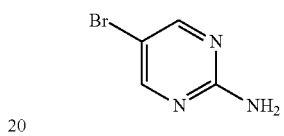

2-Aminopyrimidine (2.5 g, 26.29 mmol) was dissolved in acetonitrile (25 mL). Then N-bromosuccinimide (4.6 g, 27.9 mmol) was added in ice-bath. The reaction mixture was stirred at room temperature overnight. The mixture was evaporated under reduced pressure, and the resultant product was washed with water (100 mL) and filtered with suction. The obtained product was dried in vacuum to get a white solid. Yield: 97%; mp: 241-243° C.

Step 3. Synthesis of 2-amino-5-phenylpyrimidine (Intermediate 2-5)

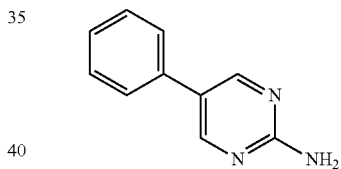

Synthetic Procedure Reference Example 1, Step 4. Compound 2-5 was prepared by using intermediate 2-4 and phenylboronic acid as starting materials. Yield: 86%; mp: 159-161° C.; $^1$H NMR (400 MHz, DMSO-$d_6$): δ 8.57 (s, Ar—H, 2H), 7.62 (d, J=7.6 Hz, Ar—H, 2H), 7.45 (t, J=7.2 Hz, Ar—H, 2H), 7.34 (t, J=7.2 Hz, Ar—H, 1H), 6.77 (s, NH$_2$, 2H); ESI-MS: m/z=172 [M+1]$^+$.

Step 4. Synthesis of 5-phenyl-N-(2-cyano-3-(piperidin-3-oxy)pyridin-5-yl)-2-aminopyrimidine (Compound 7)

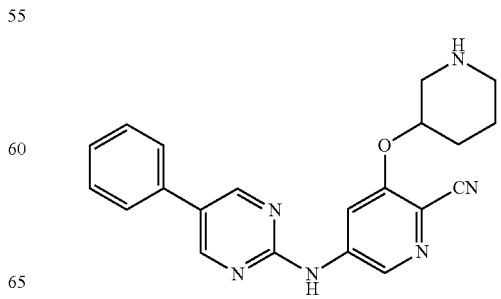

Synthetic Procedure Reference Example 1, Step 5. Compound 7 was prepared using Intermediates 2-5 and 2-2 as starting materials. Yield: 65%; mp: 84-86° C.; $^1$H NMR (500 MHz, DMSO-d$_6$): δ 10.55 (s, NH, 1H), 8.99 (s, Ar—H, 2H), 8.65 (d, J=2.0 Hz, Ar—H, 1H), 8.39 (d, J=2.0 Hz, Ar—H, 1H), 7.78 (d, J=7.0 Hz, Ar—H, 2H), 7.52 (t, J=7.5 Hz, Ar—H, 2H), 7.43 (t, j=7.0 Hz, Ar—H, 1H), 4.42-4.37 (m, CH, 1H), 3.19 (d, j=12.0 Hz, 2.0 Hz, CH$_2$, 1H), 2.81-2.77 (m, CH$_2$, 1H), 2.66-2.62 (m, CH$_2$, 1H), 2.56-2.53 (m, CH$_2$, 1H), 2.14-2.11 (m, CH$_2$, 1H), 1.76-1.71 (m, CH$_2$, 1H), 1.65-1.58 (m, CH$_2$, 1H), 1.54-1.46 (m, CH$_2$, 1H); $^{13}$C NMR (100 MHZ, DMSO-d$_6$): δ 160.22, 158.43, 157.73, 153.05, 142.82, 137.60, 133.83, 129.37, 116.42, 113.77, 111.72, 106.92, 104.53, 86.99, 57.06, 45.54, 38.63, 28.17; ESI-MS: m/z=373 [M+1]$^+$.

Preparative Example 8. 5-(3-Fluorophenyl)-N-(2-cyano-3-(piperidin-3-yloxy)pyridin-5-yl)-2-aminopyrimidine (Compound 8)

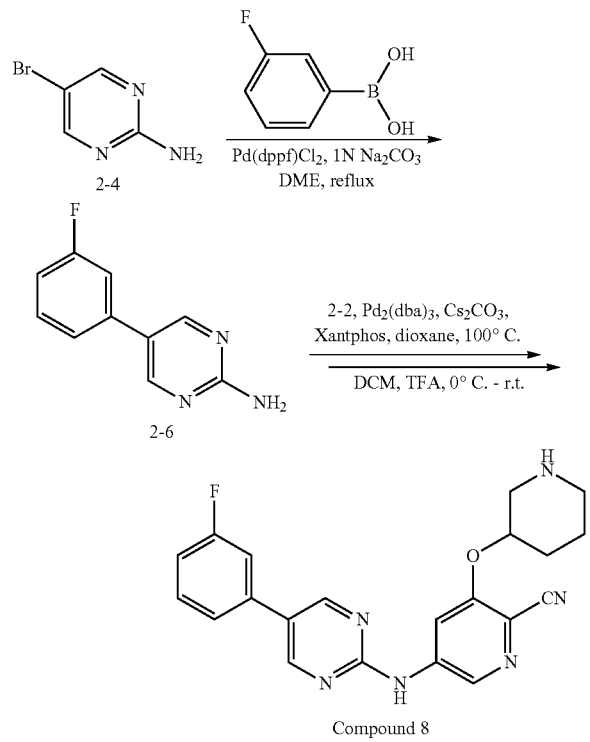

Step 1. Synthesis of 2-amino-5-(3-fluorophenyl)pyrimidine (Intermediate 2-6)

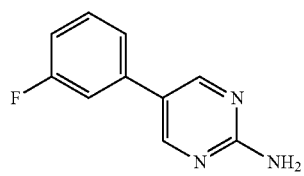 [SMILES: Nc1ncc(-c2cccc(F)c2)cn1]

Synthetic Procedure Reference Example 1, Step 4. Compound 2-6 was prepared from Intermediate 2-4 and 3-fluorophenylboronic acid to give a white solid. Yield: 83%; mp: 168-170° C.; $^1$H NMR (400 MHz, DMSO-d$_6$): δ 8.62 (s, Ar—H, 2H), 7.53-7.43 (m, Ar—H, 3H), 7.16-7.11 (m, Ar—H, 1H), 6.86 (s, NH$_2$, 2H); ESI-MS: m/z=190 [M+1]$^+$.

Step 2. Synthesis of 5-(3-fluorophenyl)-N-(2-cyano-3-(piperidin-3-yloxy)pyridin-5-yl)-2-aminopyrimidine (Compound 8)

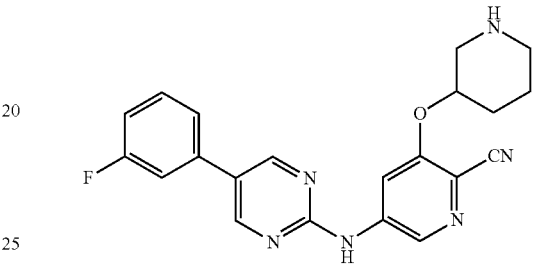

Synthetic Procedure Reference Example 1, Step 5. Compound 8 was prepared from Intermediates 2-6 and 2-2 to give a white solid. Yield: 72%; mp: 107-109° C.; NMR (500 MHz, DMSO-d$_6$): δ 10.59 (br, NH, 1H), 9.03 (s, Ar—H, 2H), 8.65 (d, J=1.5 Hz, Ar—H, 1H), 8.37 (s, Ar—H, 1H), 7.70 (d, J=10.5 Hz, Ar—H, 1H), 7.65 (d, J=8.0 Hz, Ar—H, 1H), 7.56 (dd, J=14.0 Hz, 8.0 Hz, Ar—H, 1H), 7.26 (td, J=8.5 Hz, 2.5 Hz, Ar—H, 1H), 4.42-4.37 (m, CH, 1H), 3.19 (dd, J=12.0 Hz, 2.0 Hz, CH$_2$, 1H), 2.82-2.78 (m, CH$_2$, 1H), 2.67-2.63 (m, CH$_2$, 1H), 2.57-2.52 (m, CH$_2$, 1H), 2.14-2.11 (m, CH$_2$, 1H), 1.77-1.71 (m, CH$_2$, 1H), 1.66-1.59 (m, CH$_2$, 1H), 1.54-1.47 (m, CH$_2$, 1H); ESI-MS: m/z=391 [M+1]$^+$.

Preparative Example 9. 5-(4-Fluorophenyl)-N-(2-cyano-3-(piperidin-3-oxy)pyridin-5-yl)-2-aminopyrimidine (Compound 9)

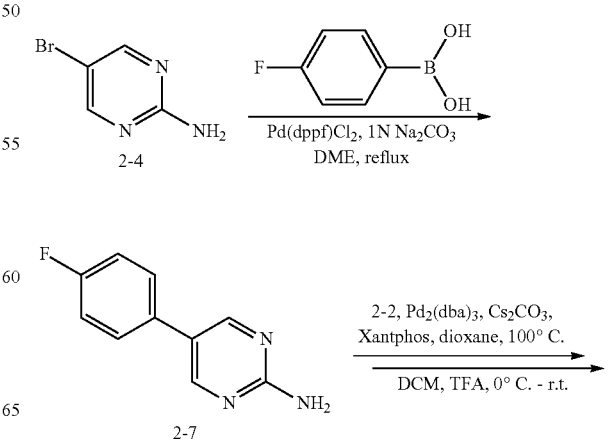

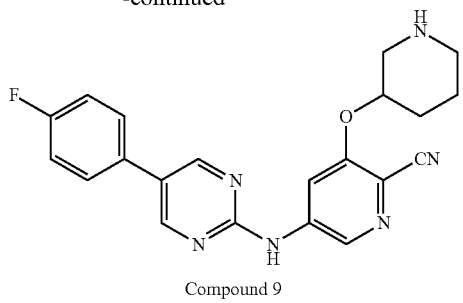

Compound 9

Step 1. Synthesis of 2-amino-5-(4-fluorophenyl)pyrimidine (Intermediate 2-7)

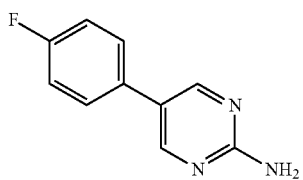

Synthetic Procedure Reference Example 1, Step 4. Compound 2-7 was prepared from the intermediate 2-4 and 4-fluorophenylboronic acid to give a white solid. Yield: 85%; mp: 172-174° C.; $^1$H NMR (400 MHz, DMSO-d$_6$): δ 8.58 (s, Ar—H, 2H), 7.68-7.64 (m, Ar—H, 2H), 7.29 (t, J=8.8 Hz, Ar—H, 2H), 6.78 (s, NH$_2$, 2H); ESI-MS: m/z=190 [M+1]$^+$.

Step 2. Synthesis of 4-(4-fluorophenyl)-N-(2-cyano-3-(piperidin-3-yloxy)pyridin-5-yl)-2-aminopyrimidine (Compound 9)

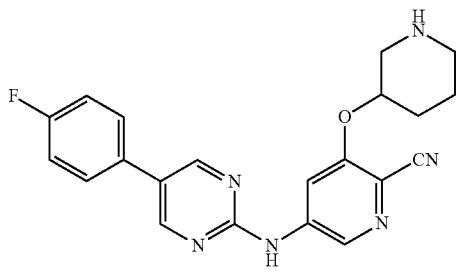 [SMILES: N#Cc1ncc(Nc2ncc(-c3ccc(F)cc3)cn2)cc1OC1CCCNC1]

Synthetic Procedure Reference Example 1, Step 5. Compound 9 was prepared from intermediates 2-7 and 2-2 to give a white solid. Yield: 78%; mp: 182-184° C.; $^1$H NMR (500 MHz, DMSO-d$_6$): δ 10.54 (br, NH, 1H), 8.96 (s, Ar—H, 2H), 8.65 (d, J=2.0 Hz, Ar—H, 1H), 8.36 (s, Ar—H, 1H), 7.83 (dd, J=8.5 Hz, 5.5 Hz, Ar—H, 2H), 7.35 (t, J=8.0 Hz, Ar—H, 2H), 4.41-4.36 (m, CH, 1H), 3.20 (dd, j=12.0 Hz, 2.5 Hz, CH$_2$, 1H), 2.82-2.78 (m, CH$_2$, 1H), 2.67-2.63 (m, CH$_2$, 1H), 2.57-2.52 (m, CH$_2$, 1H), 2.14-2.11 (m, CH$_2$, 1H), 1.77-1.71 (m, CH$_2$, 1H), 1.65-1.58 (m, CH$_2$, 1H), 1.54-1.46 (m, CH$_2$, 1H); $^{13}$C NMR (100 MHz, DMSO-d$_6$): δ 163.09, 161.14, 158.27, 157.25, 155.90, 141.82, 134.15, 130.59, 128.17, 128.11, 125.15, 116.21, 116.08, 115.91, 113.84, 109.21, 74.69, 49.65, 45.28, 29.82, 24.27; ESI-MS: m/z=391 [M+1]$^+$.

Preparative Example 10. 5-(3-Methoxyphenyl)-N-(2-cyano-3-(piperidin-3-oxy)pyridin-5-yl)-2-aminopyrimidine (Compound 10)

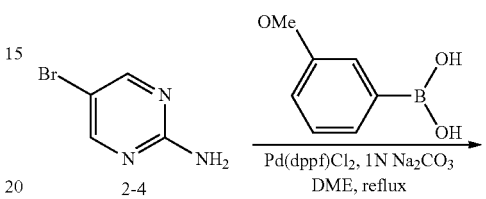

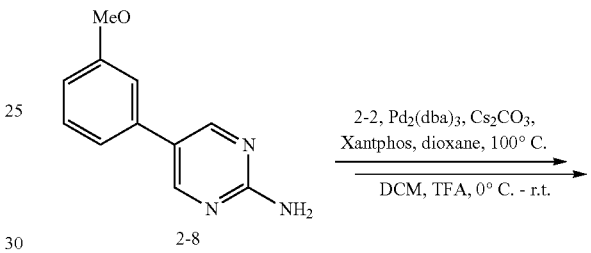

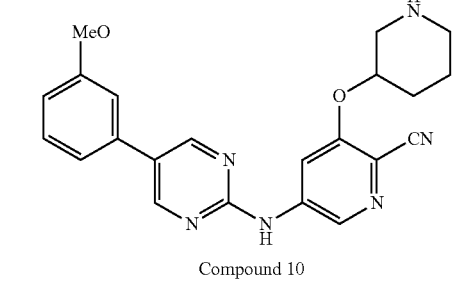

Compound 10

Step 1. Synthesis of 2-amino-5-(3-methoxyphenyl)pyrimidine (Intermediate 2-8)

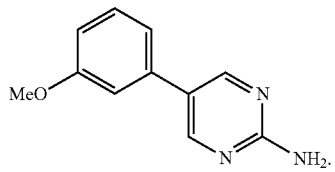

Synthetic Procedure Reference Example 1, Step 4. Compound 2-8 was prepared from intermediate 2-4 and 3-methoxyphenylboronic acid to give a white solid. Yield: 87%; mp: 133-135° C.; $^1$H NMR (400 MHz, DMSO-d$_6$): δ 8.58 (s, Ar—H, 2H), 7.36 (t, J=8.0 Hz, Ar—H, 1H), 7.18 (d, J=7.6 Hz, Ar—H, 2H), 6.90 (dd, J=8.4 Hz, 1.6 Hz, Ar—H, 1H), 6.78 (s, NH$_2$, 2H), 3.81 (s, CH$_3$, 3H); ESI-MS: m/z=202 [M+1]$^+$.

Step 2. Synthesis of 5-(3-methoxyphenyl)-N-(2-cyano-3-(piperidin-3-oxy)pyridin-5-yl)-2-aminopyrimidine (Compound 10)

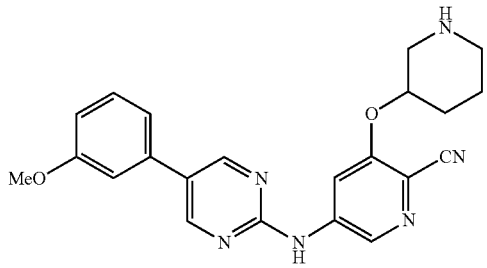 [SMILES: COc1cccc(-c2cnc(Nc3cnc(C#N)c(OC4CCCNC4)c3)nc2)c1]

Synthetic Procedure Reference Example 1, Step 5. Compound 10 was prepared from intermediates 2-8 and 2-2 to give a white solid. Yield: 74%; mp: 102-104° C.; $^1$H NMR (500 MHz, DMSO-$d_6$): δ 10.54 (br, NH, 1H), 8.98 (s, Ar—H, 2H), 8.65 (d, J=2.0 Hz, Ar—H, 1H), 8.37 (d, J=2.0 Hz, Ar—H, 1H), 7.42 (t, J=8.0 Hz, Ar—H, 1H), 7.33-7.32 (m, Ar—H, 2H), 6.99-6.97 (m, Ar—H, 1H), 4.42-4.37 (m, CH, 1H), 3.85 (s, CH$_3$, 3H), 3.20 (dd, J=12.0 Hz, 2.0 Hz, CH$_2$, 1H), 2.82-2.78 (m, CH$_2$, 1H), 2.68-2.64 (m, CH$_2$, 1H), 2.57-2.53 (m, CH$_2$, 1H), 2.14-2.11 (m, CH$_2$, 1H), 1.77-1.71 (m, CH$_2$, 1H), 1.66-1.59 (m, CH$_2$, 1H), 1.55-1.47 (m, CH$_2$, 1H); $^{13}$C NMR (100 MHz, DMSO-$d_6$): δ 159.92, 158.41, 157.25, 156.03, 141.83, 135.43, 134.18, 130.23, 125.86, 118.19, 116.23, 113.84, 113.65, 111.37, 109.21, 74.66, 55.22, 49.63, 45.29, 29.81, 24.24; ESI-MS: m/z=403 [M+1]$^+$.

Preparative Example 11

5-(4-Methoxyphenyl)-N-(2-cyano-3-(piperidin-3-oxy)pyridin-5-yl)-2-aminopyrimidine (Compound 11)

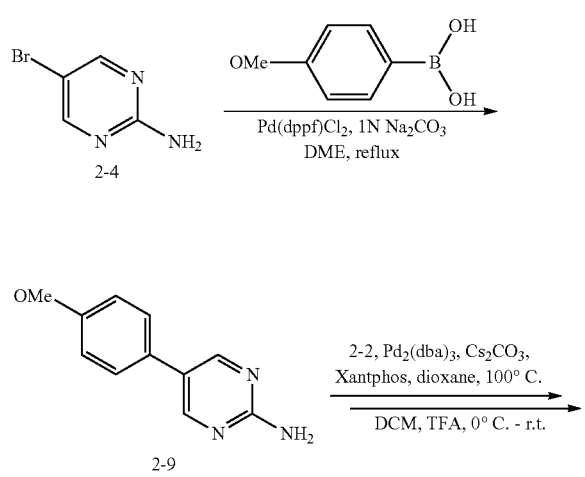

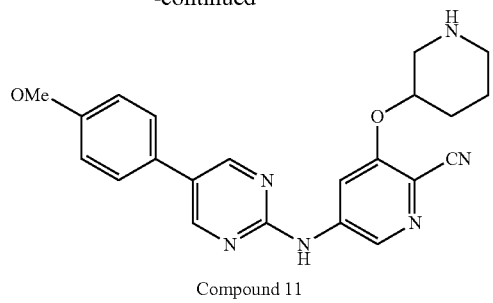

Compound 11

Step 1. Synthesis of 2-amino-5-(4-methoxyphenyl)pyrimidine (Intermediate 2-9)

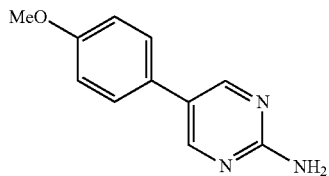 [SMILES: COc1ccc(-c2cnc(N)nc2)cc1]

Synthetic Procedure Reference Example 1, Step 4. Compound 2-9 was prepared from intermediate 2-4 and 4-methoxyphenylboronic acid to give a white solid. Yield: 82%; mp: 165-167° C.; $^1$H NMR (400 MHz, DMSO-$d_6$): δ 8.51 (s, Ar—H, 2H), 7.55 (d, J=8.8 Hz, Ar—H, 2H), 7.01 (d, J=8.8 Hz, Ar—H, 2H), 6.67 (s, NH$_2$, 2H), 3.78 (s, CH$_3$, 3H); ESI-MS: m/z=202 [M+1]$^+$.

Step 2. Synthesis of 5-(4-methoxyphenyl)-N-(2-cyano-3-(piperidin-3-yloxy)pyridin-5-yl)-2-aminopyrimidine (Compound 11)

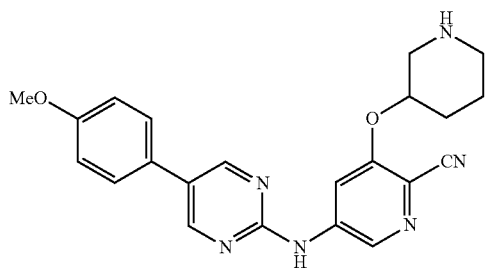 [SMILES: COc1ccc(-c2cnc(Nc3cnc(C#N)c(OC4CCCNC4)c3)nc2)cc1]

Synthetic Procedure Reference Example 1, Step 5. Compound 11 was prepared from intermediates 2-9 and 2-2 to give a white solid. Yield: 75%; mp: 218-220° C.; $^1$H NMR (400 MHz, DMSO-$d_6$): δ 10.47 (s, NH, 1H), 8.91 (s, Ar—H, 2H), 8.64 (s, Ar—H, 1H), 8.36 (s, Ar—H, 1H), 7.71 (d, J=8.8 Hz, Ar—H, 2H), 7.06 (d, J=8.8 Hz, Ar—H, 2H), 4.40-4.36 (m, CH, 1H), 3.81 (s, CH$_3$, 3H), 3.20 (d, J=12.0 Hz, CH$_2$, 1H), 2.81-2.78 (m, CH$_2$, 1H), 2.67-2.62 (m, CH$_2$, 1H), 2.56-2.51 (m, CH$_2$, 1H), 2.14-2.12 (m, CH$_2$, 1H), 1.76-1.72 (m, CH$_2$, 1H), 1.66-1.57 (m, CH$_2$, 1H), 1.54-1.46 (m, CH$_2$, 1H); $^{13}$C NMR (100 MHz, DMSO-$d_6$): δ 159.25, 157.86, 157.26, 155.34, 141.92, 134.08, 127.20, 126.29, 125.85, 116.24, 114.61, 113.65, 109.00, 74.69, 55.20, 49.69, 45.31, 29.84, 24.31; ESI-MS: m/z=403 [M+1]⁺.

Preparative Example 12

5-(Pyridin-3-yl)-N-(2-cyano-3-(piperidin-3-oxy)pyridin-5-yl)-2-aminopyrimidine (Compound 12)

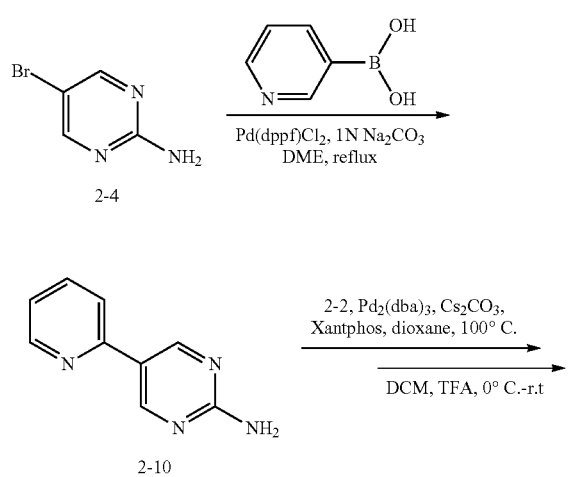

Step 1. Synthesis of 2-amino-5-(pyridin-3-yl)pyrimidine (Intermediate 2-10)

Synthetic Procedure Reference Example 1, Step 4. Compound 2-10 was prepared from intermediate 2-4 and pyridine-3-boronic acid to give a white solid. Yield: 79%; mp: 183-185° C.; $^1$H NMR (400 MHz, DMSO-d$_6$): δ 8.87 (s, Ar—H, 1H), 8.64 (s, Ar—H, 2H), 8.53 (br, Ar—H, 1H), 8.05 (d, J=7.6 Hz, Ar—H, 1H), 7.46 (d, J=4.0 Hz, Ar—H, 1H), 6.89 (s, NH$_2$, 2H); ESI-MS: m/z=173 [M+1]⁺.

Step 2. Synthesis of 5-(pyridin-3-yl)-N-(2-cyano-3-(piperidin-3-yloxy)pyridin-5-yl)-2-aminopyrimidine (Compound 12)

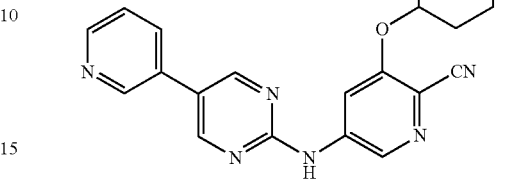

Synthetic Procedure Reference Example 1, Step 5. Compound 12 was prepared from intermediates 2-10 and 2-2 to give a white solid. Yield: 75%; mp: 221-223° C.; $^1$H NMR (500 MHz, DMSO-d$_6$): δ 10.61 (br, NH, 1H), 9.06 (s, Ar—H, 2H), 9.00 (d, J=2.5 Hz, Ar—H, 1H), 8.67 (d, J=1.5 Hz, Ar—H, 1H), 8.62 (dd, J=4.5 Hz, 1.5 Hz, Ar—H, 1H), 8.37 (d, J=2.0 Hz, Ar—H, 1H), 8.21 (td, J=8.0 Hz, 2.0 Hz, Ar—H, 1H), 7.54 (dd, J=8.0 Hz, 4.0 Hz, Ar—H, 1H), 4.43-4.39 (m, CH, 1H), 3.20 (dd, J=12.0 Hz, 2.0 Hz, CH$_2$, 1H), 2.83-2.78 (m, CH$_2$, 1H), 2.69-2.65 (m, CH$_2$, 1H), 2.59-2.54 (m, CH$_2$, 1H), 2.15-2.12 (m, CH$_2$, 1H), 1.78-1.72 (m, CH$_2$, 1H), 1.67-1.60 (m, CH$_2$, 1H), 1.55-1.47 (m, CH$_2$, 1H); ESI-MS: m/z=374 [M+1]⁺.

Preparative Example 13

5-(Thien-2-yl)-N-(2-cyano-3-(piperidin-3-oxy)pyridin-5-yl)-2-aminopyrimidine (Compound 13)

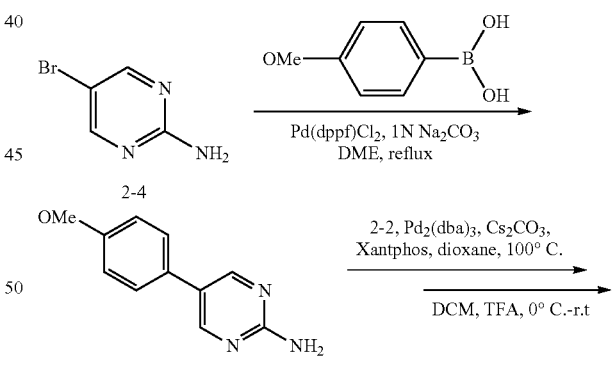

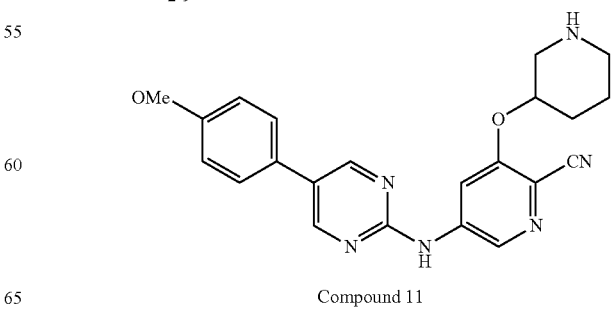

Compound 11

Step 1. Synthesis of 2-amino-5-(thien-2-yl)pyrimidine (Intermediate 2-11)

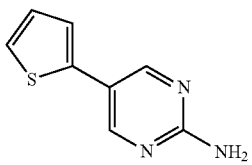 [SMILES: Nc1ncc(-c2cccs2)cn1]

Synthetic Procedure Reference Example 1, Step 4. Compound 2-11 was prepared from intermediate 2-4 and thienyl-2-boronic acid to give a white solid. Yield: 84%; mp: 156-158° C.; $^1$H NMR (400 MHz, DMSO-d$_6$): δ 8.53 (s, Ar—H, 2H), 7.49 (d, J=4.8 Hz, Ar—H, 1H), 7.38 (d, J=2.8 Hz, Ar—H, 1H), 7.12 (t, J=4.4 Hz, Ar—H, 1H), 6.87 (s, NH$_2$, 2H): ESI-MS: m/z=178 [M+1]$^+$.

Step 2. Synthesis of 5-(thien-2-yl)-N-(2-cyano-3-(piperidin-3-yloxy)pyridin-5-yl)-2-aminopyrimidine (Compound 13)

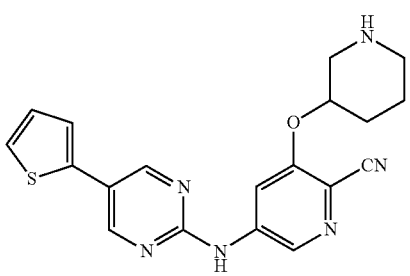 [SMILES: N#Cc1ncc(Nc2ncc(-c3cccs3)cn2)cc1OC1CCCNC1]

Synthetic Procedure Reference Example 1, Step 5. Compound 13 was prepared from intermediates 2-11 and 2-2 to give a white solid. Yield: 74%; mp: 212-214° C.; $^1$H NMR (500 MHz, DMSO-d$_6$): δ 10.58 (br, NH, 1H), 8.93 (s, Ar—H, 2H), 8.61 (d, J=2.0 Hz, Ar—H, 1H), 8.35 (d, J=2.0 Hz, Ar—H, 1H), 7.63-7.61 (m, Ar—H, 2H), 7.20 (dd, J=5.0 Hz, 3.5 Hz, Ar—H, 1H), 4.42-4.37 (m, CH, 1H), 3.19 (dd, J=12.0 Hz, 2.0 Hz, CH$_2$, 1H), 2.82-2.78 (m, CH$_2$, 1H), 2.67-2.63 (m, CH$_2$, 1H), 2.57-2.52 (m, CH$_2$, 1H), 2.14-2.10 (m, CH$_2$, 1H), 1.77-1.71 (m, CH$_2$, 1H), 1.66-1.59 (m, CH$_2$, 1H), 1.54-1.46 (m, CH$_2$, 1H); $^{13}$C NMR (100 MHz, DMSO-d$_6$): δ 158.00, 157.25, 154.63, 141.67, 136.46, 134.18, 128.55, 126.15, 124.27, 121.13, 116.20, 113.91, 109.24, 74.64, 49.63, 45.30, 29.81, 24.26; ESI-MS: m/z=379 [M+1]$^+$.

Preparative Example 14

5-(Furan-2-yl)-N-(2-cyano-3-(piperidin-3-oxy)pyridin-5-yl)-2-aminopyrimidine (Compound 14)

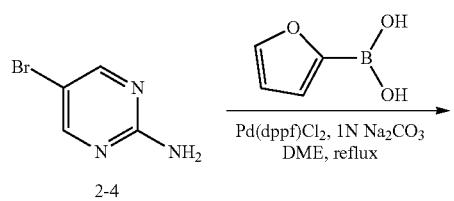

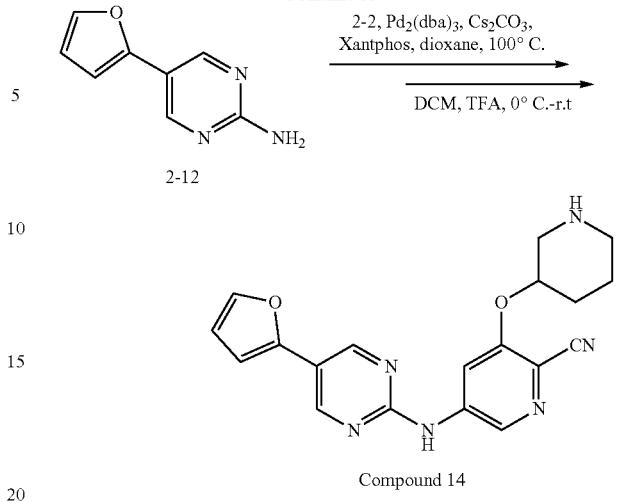

Step 1. Synthesis of 2-amino-5-(furan-2-yl)pyrimidine (Intermediate 2-12)

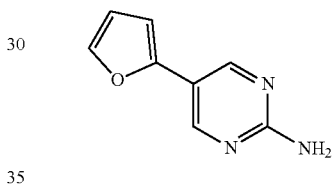

Synthetic Procedure Reference Example 1, Step 4. Compound 2-12 was prepared from intermediate 2-4 and furan-2-boronic acid to give a white solid. Yield: 83%; mp: 156-158° C.; $^1$H NMR (400 MHz, DMSO-d$_6$): δ 8.57 (s, Ar—H, 2H), 7.69 (s, Ar—H, 1H), 6.88 (s, NH, 2H), 6.78 (d, J=2.0 Hz, Ar—H, 1H), 6.56 (s, Ar—H, 1H); ESI-MS: m/z=162 [M+1]$^+$

Step 2. Synthesis of 5-(furan-2-yl)-N-(2-cyano-3-(piperidin-3-yloxy)pyridin-5-yl)-2-aminopyrimidine (Compound 14)

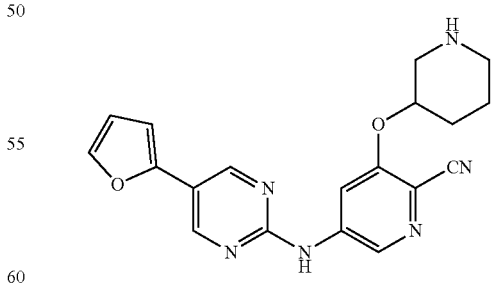

Synthetic Procedure Reference Example 1, Step 5. Compound 14 was prepared from intermediates 2-12 and 2-2 to give a white solid. Yield: 70%; mp: 200-202° C.; $^1$H NMR (400 MHz, DMSO-d$_6$): δ 10.58 (br, NH, 1H), 8.95 (s, Ar—H, 2H), 8.59 (d, J=1.2 Hz, Ar—H, 1H), 8.36 (s, Ar—H, 1H), 7.81 (s, Ar—H, 1H), 7.05 (d, J=2.8 Hz, Ar—H, 1H), 6.65 (t, J=1.6 Hz, Ar—H, 1H), 4.41-4.37 (m, CH, 1H), 3.20 (d, J=12 Hz, CH$_2$, 1H), 2.82-2.79 (m, CH$_2$, 1H), 2.67-2.62 (m, CH$_2$, 1H), 2.57-2.55 (m, CH$_2$, 1H), 2.14-2.12 (m, CH$_2$, 1H), 1.76-1.73 (m, CH$_2$, 1H), 1.67-1.58 (m, CH$_2$, 1H), 1.54-1.49 (m, CH$_2$, 1H); $^{13}$C NMR (100 MHZ, DMSO-d$_6$): δ 157.76, 157.23, 153.18, 148.23, 143.35, 141.62, 134.17, 117.90, 116.19, 113.89, 112.08, 109.23, 106.19, 74.66, 49.63, 45.30, 29.81, 24.27; ESI-MS: m/z=363 [M+1]$^+$ Preparative Example 15

(R)-5-(1-Methyl-1H-pyrazol-4-yl)-N-(2-cyano-3-(piperidin-3-yloxy)pyridine-5-yl)-2-aminopyrimidine (Compound 15)

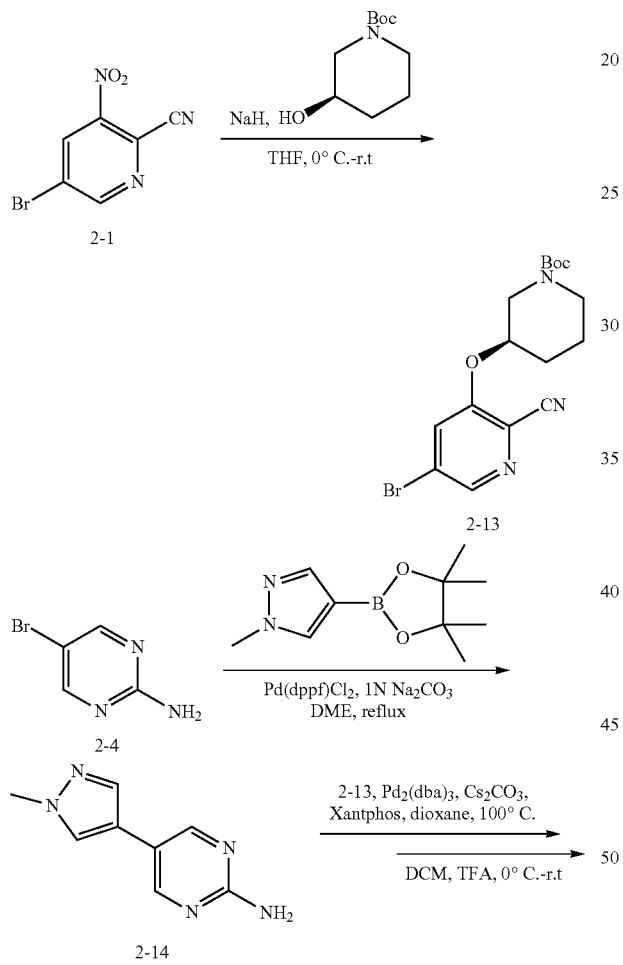

Step 1. Synthesis of (R)-2-cyano-5-bromo-3-(N-tert-butoxycarbonylpiperidin-3-yloxy)pyridine (Intermediate 2-13)

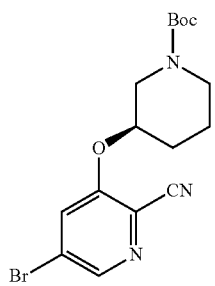 [SMILES: CC(C)(C)OC(=O)N1CCC[C@@H](Oc2cc(Br)cnc2C#N)C1]

Synthetic Procedure Reference Example 1, Step 1. Compound 2-13 was prepared from 5-bromo-3-nitro-2-cyanopyridine (Compound 2-1) and (R)—N-tert-butyloxycarbonyl-3-hydroxypiperidine as starting materials according to the same procedure as Compound 1-2, and a yellow oil. Yield: 76%; $^1$H NMR (500 MHz, DMSO-d$_6$): δ 8.26 (s, Ar—H, 1H), 7.53 (s, Ar—H, 1H), 4.38 (br, CH, 1H), 3.63 (br, CH, 1H), 3.51 (br, CH, 1H), 3.38 (br, CH, 2H), 1.98-1.96 (m, CH, 1H), 1.91-1.85 (m, CH, 2H), 1.51 (br, CH, 1H), 1.36 (s, CH$_3$×3, 9H); ESI-MS: m/z=382 [M+1]$^+$.

Step 2. Synthesis of 2-amino-5-(1-methyl-1H-pyrazol-4-yl)pyrimidine (Intermediate 2-14)

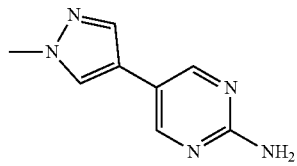

Synthetic Procedure Reference Example 1, Step 4. Compound 2-14 was prepared from intermediate 2-4 and 1-methylpyrazol-4-boronic acid pinacol ester as a white solid. Yield: 85%; mp: 174-176° C.; $^1$H NMR (400 MHz, DMSO-d$_6$): δ 8.46 (s, Ar—H, 2H), 8.03 (s, Ar—H, 1H), 7.78 (s, Ar—H, 1H), 6.57 (s, NH$_2$, 2H), 3.84 (s, CH$_3$, 3H); ESI-MS: m/z=176 [M+1]$^+$.

Step 3. Synthesis of (R)-5-(1-methyl-1H-pyrazol-4-yl)-N-(2-cyano-3-(piperidin-3-yloxy)pyridin-5-yl)-2-aminopyrimidine (Compound 15)

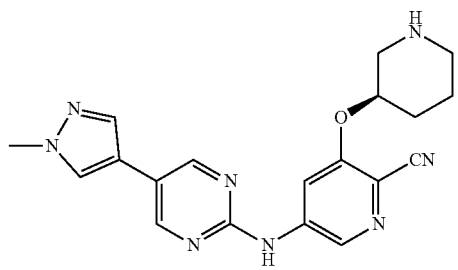 [SMILES: Cn1cc(-c2cnc(Nc3cnc(C#N)c(O[C@@H]4CCCNC4)c3)nc2)cn1]

Synthetic Procedure Reference Example 1, Step 5. Compound 15 was prepared from intermediates 2-14 and 2-13 to give a white solid. Yield: 73%; mp: 230° C. (decomposition); $^1$H NMR (500 MHz, DMSO-d$_6$): δ 10.42 (br, NH, 1H), 8.87 (s, Ar—H, 2H), 8.59 (d, J=1.5 Hz, Ar—H, 1H), 8.35 (d, J=2.0 Hz, Ar—H, 1H), 8.23 (s, Ar—H, 1H), 7.97 (s, Ar—H, 1H), 4.41-4.36 (m, CH, 1H), 3.89 (s, CH$_3$, 3H), 3.19 (dd, J=12.0 Hz, 2.0 Hz, CH$_2$, 1H), 2.82-2.78 (m, CH$_2$, 1H), 2.68-2.64 (m, CH$_2$, 1H), 2.58-2.53 (m, CH$_2$, 1H), 2.14-2.11 (m, CH$_2$, 1H), 1.78-1.72 (m, CH$_2$, 1H), 1.65-1.58 (m, CH$_2$, 1H), 1.54-1.46 (m, CH$_2$, 1H); $^{13}$C NMR (125 MHz, DMSO-d$_6$): δ 157.28, 154.26, 141.98, 135.75, 134.02, 127.58, 119.77, 116.28, 115.46, 113.46, 108.76, 74.59, 49.62, 45.27, 38.74, 29.78, 24.19; ESI-MS: m/z=377 [M+1]$^+$.

Preparative Example 16

(S)-5-(1-Methyl-1H-pyrazol-4-yl)-N-(2-cyano-3-(piperidin-3-yloxy)pyridine-5-yl-2-aminopyrimidine (Compound 16)

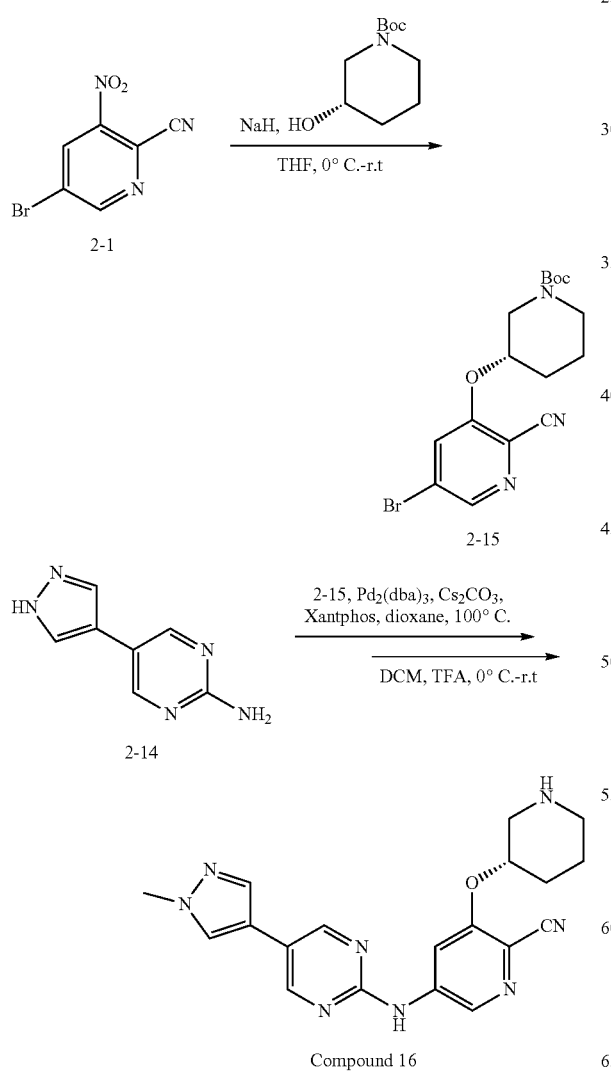

Step 1. Synthesis of (S)-2-cyano-5-bromo-3-(N-tert-butoxycarbonylpiperidin-3-yloxy)pyridine (Intermediate 2-15)

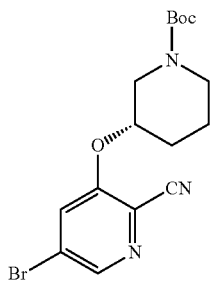 [SMILES: CC(C)(C)OC(=O)N1CCC[C@H](Oc2cc(Br)cnc2C#N)C1]

Synthetic Procedure Reference Example 1, Step 1. Compound 2-15 was prepared from 5-bromo-3-nitro-2-cyano-pyridine (Compound 2-1) and (S)—N-tert-butoxycarbonyl-3-hydroxypiperidine as starting materials according to the same procedure as Compound 1-2, a yellow oil. Yield: 78%; $^1$H NMR (500 MHz, DMSO-d$_6$): δ 8.26 (s, Ar—H, 1H), 7.53 (s, Ar—H, 1H), 4.38 (br, CH, 1H), 3.63 (br, CH, 1H), 3.51 (br, CH, 1H), 3.38 (br, CH, 2H), 1.98-1.96 (m, CH, 1H), 1.91-1.85 (m, CH, 2H), 1.51 (br, CH, 1H), 1.36 (s, CH$_3$λ3, 9H); ESI-MS: m/z=382 [M+1]$^+$.

Step 2. Synthesis of (N)-5-(1-methyl-1H-pyrazol-4-yl)-N-(2-cyano-3-(piperidin-3-yloxy)pyridin-5-yl) 2-aminopyrimidine (Compound 16)

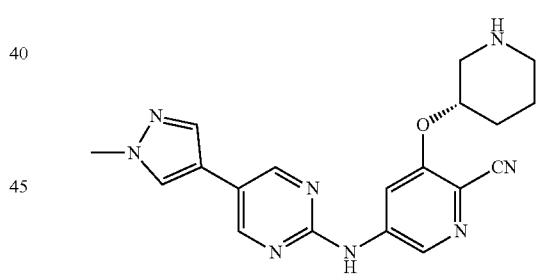

Synthetic Procedure Reference Example 1, Step 5. Compound 16 was prepared from intermediates 2-14 and 2-15 to give a white solid. Yield: 72%; mp: 230° C. (decomposition); $^1$H NMR (500 MHz, DMSO-d$_6$): δ 10.42 (br, NH, 1H), 8.87 (s, Ar—H, 2H), 8.59 (d, J=1.5 Hz, Ar—H, 1H), 8.35 (d, J=2.0 Hz, Ar—H, 1H), 8.23 (s, Ar—H, 1H), 7.97 (s, Ar—H, 1H), 4.41-4.36 (m, CH, 1H), 3.89 (s, CH$_3$, 3H), 3.19 (dd, J=12.0 Hz, 2.0 Hz, CH$_2$, 1H), 2.82-2.78 (m, CH$_2$, 1H), 2.68-2.64 (m, CH$_2$, 1H), 2.58-2.53 (m, CH$_2$, 1H), 2.14-2.11 (m, CH$_2$, 1H), 1.78-1.72 (m, CH$_2$, 1H), 1.65-1.58 (m, CH$_2$, 1H), 1.54-1.46 (m, CH$_2$, 1H); $^{13}$C NMR (125 MHz, DMSO-d$_6$): δ 157.28, 154.26, 141.98, 135.75, 134.02, 127.58, 119.77, 116.28, 115.46, 113.46, 108.76, 74.59, 49.62, 45.27, 38.74, 29.78, 24.19; ESI-MS: m/z=377 [M+1]$^+$.

Preparative Example 17

4-Methoxy-5-(3-fluorophenyl)-N-(2-cyano-3-(piperidin-4-methyl)oxypyridin-5-yl)-2-aminopyrimidine (Compound 17)

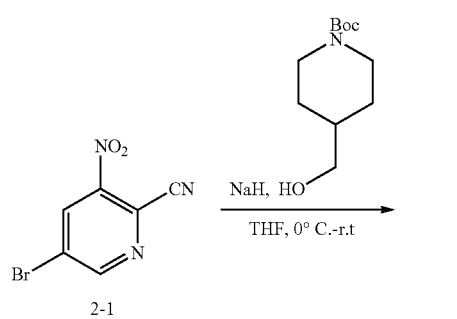

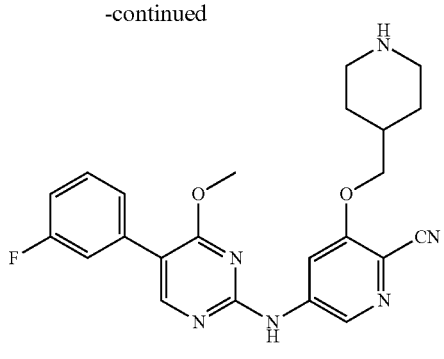

Compound 17

Step 1. Synthesis of 2-cyano-5-bromo-3-(N-tert-butoxycarbonylpiperidin-4-methyl)oxypyridine (Intermediate 2-16)

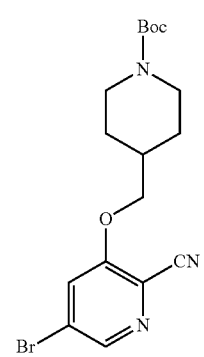 [SMILES: CC(C)(C)OC(=O)N1CCC(COc2cc(Br)cnc2C#N)CC1]

Synthetic Procedure Reference Example 1, Step 1. Compound 2-16 was prepared from 5-bromo-3-nitro-2-cyanopyridine (Compound 2-1) and N-tert-butoxycarbonylpiperidin-4-methanol as starting materials according to the same procedure as Compound 1-2. Yield: 80%; $^1$H NMR (500 MHz, CDCl$_3$): δ 8.34 (s, Ar—H, 1H), 7.51 (s, Ar—H, 1H), 4.20 (d, J=11.5 Hz, CH$_2$, 2H), 3.95 (br, CH$_2$, 2H), 2.80 (br, CH$_2$, 2H), 2.14-2.05 (m, CH, 1H), 1.89 (br, CH$_2$, 2H), 1.47 (s, CH$_3$×3, 9H), 1.33-1.26 (m, CH$_2$, 2H); ESI-MS: m/z=206 [M+1]$^+$.

Step 2. Synthesis of 4-methoxy-2-chloro-5-bromopyrimidine (Intermediate 2-17)

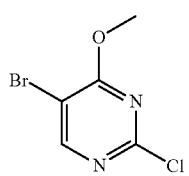

5-Bromo-2,4-dichloropyrimidine (500 mg, 2.194 mmol) was dissolved in anhydrous methanol (5 mL), and sodium methoxide (sodium 56 mg, 2.42 mmol) in methanol (1.85 mL) was added to the above solution under nitrogen. The mixture was stirred at room temperature overnight. The reaction was quenched by the addition of saturated ammonium chloride solution and was evaporated at reduced pressure to remove the solvent. Then CH$_2$Cl$_2$ (30 mL) was added and was washed with water (30 mL). The organic layer was separated and evaporated under a reduced pressure to remove the solvent. The crude product was purified by silica gel column chromatography (eluent PE:EtOAc=4:1) to give a white solid. Yield: 90%; $^1$H NMR (400 MHz, CDCl$_3$): δ 8.44 (s, Ar—H, 1H), 4.11 (s, CH$_3$, 3H); ESI-MS: m/z=223 [M+1]$^+$.

Step 3. Synthesis of 4-methoxy-5-bromo-2-aminopyrimidine (Intermediate 2-18)

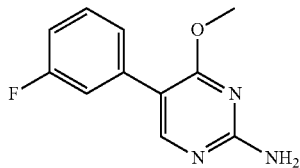 [SMILES: COc1nc(N)ncc1-c1cccc(F)c1]

Synthetic Procedure Reference Example 1, Step 3. Compound 2-18 was prepared from intermediate 2-17 as a starting material according to the same procedure as Compound 1-5, a white solid. Yield: 75%; $^1$H NMR (500 MHz, CDCl$_3$): δ 8.13 (s, Ar—H, 1H), 5.41 (s, NH$_2$, 2H), 3.91 (s, CH$_3$, 3H); ESI-MS: m/z=205 [M+1]$^+$.

Step 4. Synthesis of 4-methoxy-5-(3-fluorophenyl)-2-aminopyrimidine (Intermediate 2-19)

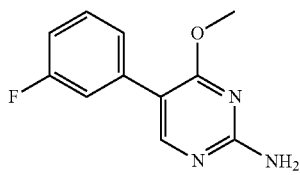 [SMILES: COc1nc(N)ncc1-c1cccc(F)c1]

Synthetic Procedure Reference Example 1, Step 4. Compound 2-19, a white solid, was prepared from intermediate 2-18 and 3-fluorophenylboronic acid as starting materials. Yield: 88%; mp: 127-128° C.; $^1$H NMR (500 MHz, CDCl$_3$): δ 7.98 (s, Ar—H, 1H), 7.46-7.42 (m, Ar—H, 1H), 7.18 (d, J=7.5 Hz, Ar—H, 1H), 7.12-7.08 (m, Ar—H, 2H), 5.19 (s, NH$_2$, 2H), 4.10 (S, NH$_2$, 2H), 3.96 (S, CH$_3$, 3H); ESI-MS: m/z=220 [M+1]$^+$.

Step 5. Synthesis of 4-methoxy-5-(3-fluorophenyl)-N-(2-cyano-3-(piperidin-4-methyl)oxypyridin-5-yl)-2-aminopyrimidine (Compound 17)

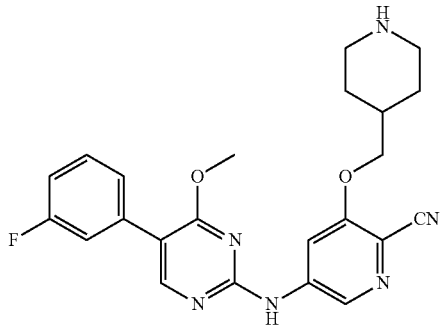 [SMILES: COc1nc(Nc2cnc(C#N)c(OCC3CCNCC3)c2)ncc1-c1cccc(F)c1]

Synthetic Procedure Reference Example 1, Step 5. Compound 17, a white solid, was prepared from intermediates 2-16 and 2-19. Yield: 79%; mp: 139-141° C.; $^1$H NMR (500 MHz, CDCl$_3$): δ 8.36 (d, J=2.0 Hz, Ar—H, 1H), 8.18 (s, Ar—H, 1H), 8.08 (d, J=2.0 Hz, Ar—H, 1H), 7.58-7.54 (m, Ar—H, 1H), 7.24-7.21 (m, Ar—H, 2H), 7.15-7.12 (m, Ar—H, 1H), 7.04 (br, NH, 1H), 4.05 (s, CH$_3$, 3H), 3.97 (d, J=6.5 Hz, CH$_2$, 2H), 3.20-3.18 (m, CH$_2$, 2H), 2.73-2.72 (m, CH$_2$, 2H), 2.13-2.06 (m, CH, 1H), 1.93-1.91 (m, CH$_2$, 2H), 1.40-1.32 (m, CH$_2$, 2H); $^{13}$C NMR (125 MHz, DMSO-d$_6$): δ 163.85, 163.46, 161.52, 158.92, 158.03, 157.93, 141.22, 136.25, 135.99, 135.92, 131.07, 131.01, 125.40, 116.22, 116.05, 115.84, 114.98, 114.82, 114.64, 114.14, 111.54, 72.92, 55.50, 44.11, 34.25, 27.19; ESI-MS: m/z=435 [M+1]$^+$.

Preparative Example 18

4-Methoxy-5-(3-fluorophenyl)-N-(2-cyano-3-(piperidin-4-methyl)oxypyridin-5-yl)-2-aminopyrimidine (Compound 18)

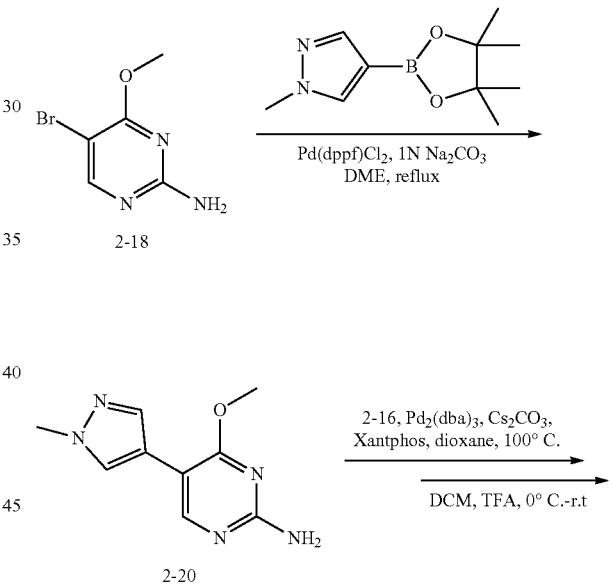

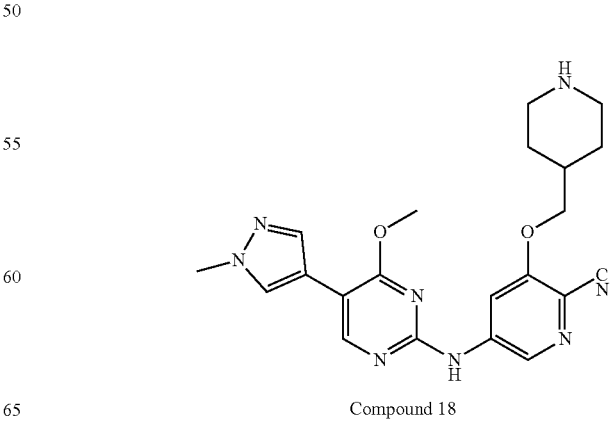

Compound 18

Step 1. Synthesis of 4-methoxy-5-(1-methyl-1H-pyrazol-4-yl)-2-aminopyrimidine (Intermediate 2-20)

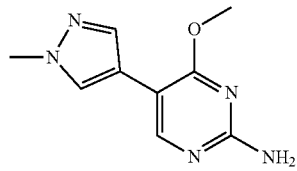

Synthetic Procedure Reference Example 1, Step 4. Compound 2-20, a white solid, was prepared from intermediate 2-18 and 1-methylpyrazol-4-boronic acid pinacol ester. Yield: 85%; $^1$H NMR (500 MHz, CDCl$_3$): δ 7.96 (s, Ar—H, 1H), 7.58 (s, Ar—H, 1H), 7.47 (s, Ar—H, 1H), 5.18 (s, NH$_2$, 2H), 3.97 (s, CH$_3$, 3H), 3.94 (s, CH$_3$, 3H); ESI-MS: m/z=206 [M+1]$^+$.

Step 2. Synthesis of 4-methoxy-5-(1-methyl-1H-pyrazol-4-yl)-N-(2-cyano-3-(piperidin-4-methyl)oxypyridin-5-yl)-2-aminopyrimidine (Compound 18)

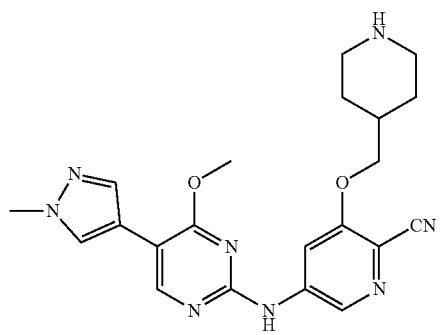 [SMILES: COc1nc(Nc2cnc(C#N)c(OCC3CCNCC3)c2)ncc1-c1cnn(C)c1]

Synthetic Procedure Reference Example 1, Step 5. Compound 18, a white solid, was prepared from intermediates 2-16 and 2-20. Yield: 82%; mp: 213-215° C.; $^1$H NMR (500 MHz, DMSO-d$_6$): δ 9.02 (s, Ar—H, 1H), 8.69 (d, J=2.0 Hz, Ar—H, 1H), 8.25 (s, Ar—H, 1H), 8.24 (d, j=2.0 Hz, Ar—H, 1H), 8.05 (s, NH, 1H), 7.70 (s, Ar—H, 1H), 5.33 (s, NH, 1H), 4.05 (d, j=6.5 Hz, CH$_2$, 2H), 3.92 (s, CH$_3$, 3H), 3.91 (s, CH$_3$, 3H), 3.31-3.28 (m, CH$_2$, 2H), 2.93-2.87 (m, CH$_2$, 2H), 2.19-2.11 (m, CH, 1H), 1.93-1.91 (m, CH$_2$, 2H), 1.55-1.47 (m, CH$_2$, 2H); ESI-MS: m/z=421 [M+1]$^+$.

Preparative Example 19

Preparation of Compounds 19 to 31.

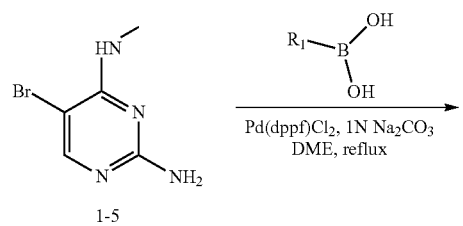

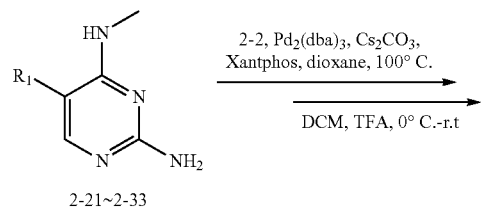

2-21: R$_1$ = phenyl
2-22: R$_1$ = 3-fluorophenyl
2-23: R$_1$ = 4-fluorophenyl
2-24: R$_1$ = 2-fluorophenyl
2-25: R$_1$ = 3-methoxyphenyl
2-26: R$_1$ = 4-methoxyphenyl
2-27: R$_1$ = 2,4-dimethoxyphenyl
2-28: R$_1$ = pyridin-3-yl
2-29: R$_1$ = pyridin-4-yl
2-30: R$_1$ = thien-2-l
2-31: R$_1$ = furan-2-yl
2-32: R$_1$ = 5-chlorofuran-2-yl
2-33: R$_1$ = 5-methoxycarbonylthien-2-yl

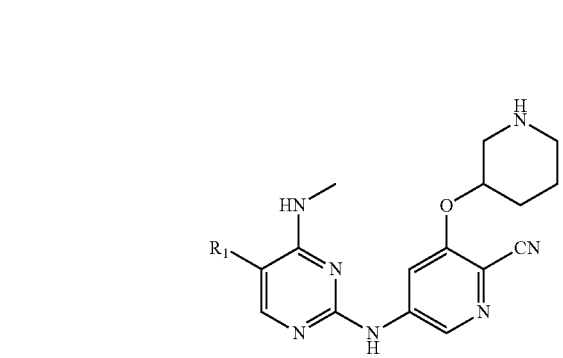

compound 19-31 compound 19: R$_1$ = phenyl
compound 20: R$_1$ = 3-fluorophenyl
compound 21: R$_1$ = 4-fluorophenyl
compound 22: R$_1$ = 2-fluorophenyl
compound 23: R$_1$ = 3-methoxyphenyl
compound 24: R$_1$ = 4-methoxyphenyl
compound 25: R$_1$ = 2,4-dimethoxyphenyl
compound 26: R$_1$ = pyridin-3-yl
compound 27: R$_1$ = pyridin-4-yl
compound 28: R$_1$ = thien-2-l
compound 29: R$_1$ = furan-2-yl
compound 30: R$_1$ = 5-chlorofuran-2-yl
compound 31: R$_1$ = 5-methoxycarbonylthien-2-yl

Step 1. Synthesis of Intermediates 2-21-2-33

The synthetic procedure was described as Example 1, Step 4. Compounds 2-21-2-33 were prepared from the intermediate 1-5 and the corresponding boronic acid to obtain white solid.

Step 2. Synthesis of Compound 19-31

The synthetic procedure was described as Example 1, Step 5. Compounds 19-31 were prepared from the intermediates 2-21 to 2-33 and 2-2 to give white solids.

The synthetic method of compound 30 is as follows:

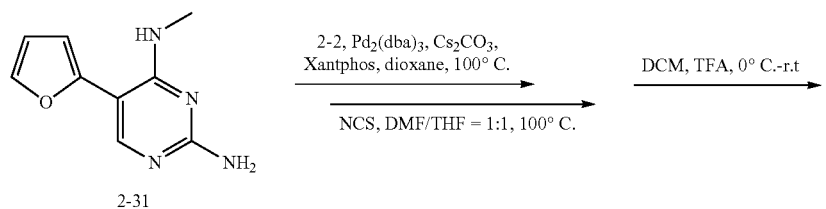

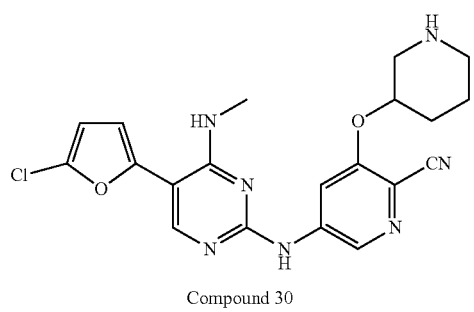

Compound 30

Synthetic Procedure Reference Example 1, Step 5. Intermediates for compound was prepared from intermediates 2-31 and 2-2, and the Boc protected intermediate (100 mg, 0.203 mmol) was dissolved in DMF/THF (1:1) mixed solution (2 mL), N-chlorosuccinimide (27 mg, 0.203 mmol) was added drop wise, and stirred at 60° C. for 5 hours. The solvent was evaporated under reduced pressure. AcOEt was added, washed with water. The organic layer was combined, dried over anhydrous sodium sulfate and evaporated under reduced pressure to get resultant product, then the Boc protected group was removed with trifluoroacetic acid to afford yellow solid.

Preparative Example 20. $N^4$-Methyl-5-(1-methyl-1H-pyrazol-4-yl)-$N^2$-(2-cyano-3-(piperidin-3-yloxy)pyridin-5-yl)-2,4-diaminopyrimidine (Compound 32)

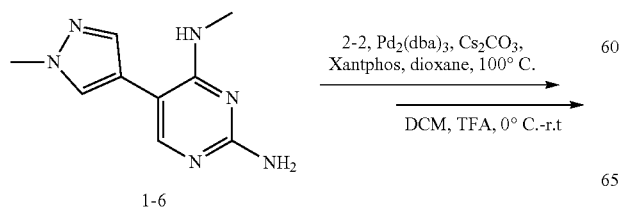

-continued

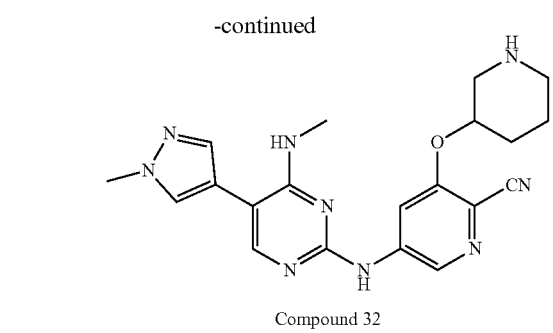

Compound 32

Step 1. Synthesis of $N^4$-methyl-5-(1-methyl-1H-pyrazol-4-yl)-$N^2$-(2-cyano-3-(piperidin-3-yloxy)pyridin-5-yl-2,4-diaminopyrimidine (Compound 32)

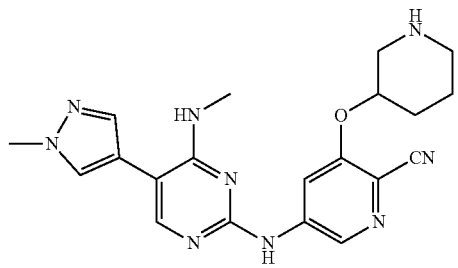 [SMILES: CNc1nc(Nc2cnc(C#N)c(OC3CCCNC3)c2)ncc1-c1cnn(C)c1]

Synthetic Procedure Reference Example 1, Step 5. Compound 32 was prepared from intermediates 1-6 and 2-2 to give a white solid. Yield: 79%; mp: 207-209° C.; $^1$H NMR (500 MHz, DMSO-$d_6$): δ 9.92 (s, NH, 1H), 8.51 (s, Ar—H, 2H), 7.91 (s, Ar—H, 1H), 7.90 (s, Ar—H, 1H), 7.61 (s, Ar—H, 1H), 6.74 (q, J=4.5 Hz, NH, 1H), 4.40-4.35 (m, CH, 1H), 3.89 (s, CH$_3$, 3H), 3.15 (dd, J=12.0 Hz, 2.0 Hz, CH$_2$, 1H), 2.94 (d, J=5.0 Hz, CH$_3$, 3H), 2.79-2.74 (m, CH$_2$, 1H), 2.63-2.59 (m, CH$_2$, 1H), 2.54-2.48 (m, CH$_2$, 1H), 2.11-2.07 (m, CH$_2$, 1H), 1.74-1.68 (m, CH$_2$, 1H), 1.62-1.55 (m, CH$_2$, 1H), 1.45-1.37 (m, CH$_2$, 1H); ESI-MS: m/z=406 [M+1]$^+$.

Preparative Example 21. N$^4$-Methyl-5-(1-methyl-1H-pyrazol-5-yl)-N$^2$-(2-cyano-3-(piperidin-3-yloxy)pyridin-5-yl)-2,4-diaminopyrimidine (Compound 33)

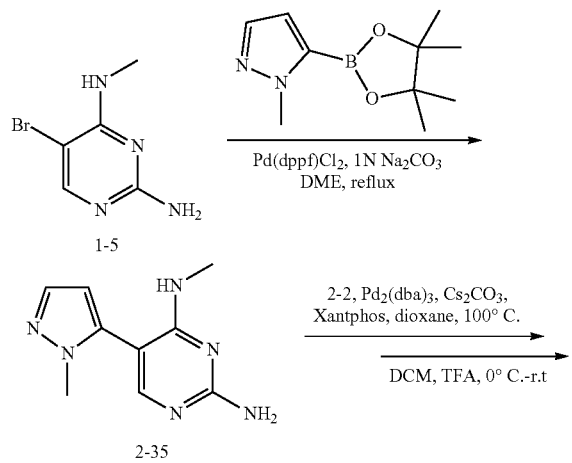

Compound 33

Step 1. Synthesis of 5-(1-methyl-1H-pyrazol-5-yl)-N$^4$-methyl-2,4-diaminopyrimidine (Intermediate 2-35)

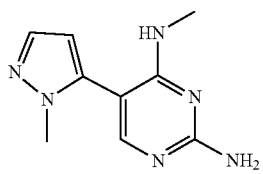

Synthetic Procedure Reference Example 1, Step 4. Compound 2-35 was prepared from intermediate 1-5 and 1-methyl-1H-pyrazole-5-boronic acid pinacol ester as a white solid. Yield: 65%; $^1$H NMR (500 MHz, DMSO-$d_6$): δ 7.54 (s, Ar—H, 1H), 7.47 (d, J=1.5 Hz, Ar—H, 1H), 6.24 (br, NH$_2$, 2H), 6.20 (d, J=1.5 Hz, Ar—H, 1H), 6.07 (q, J=4.5 Hz, NH, 1H), 3.61 (s, CH$_3$, 3H), 2.75 (d, J=4.5 Hz, CH$_3$, 3H); ESI-MS: m/z=205 [M+1]$^+$.

Step 2. Synthesis of N$^4$-methyl-5-(1-methyl-1H-pyrazol-4-yl)-N$^2$-(2-cyano-3-(piperidin-3-yloxy)pyridin-5-yl-2,4-diaminopyrimidine (Compound 33)

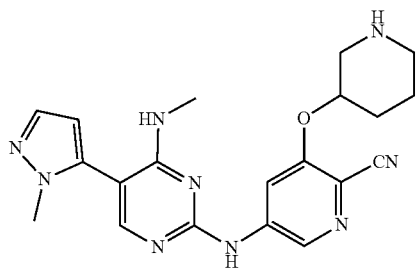 [SMILES: CNc1nc(Nc2cnc(C#N)c(OC3CCCNC3)c2)ncc1-c1ccnn1C]

Synthetic Procedure Reference Example 1, Step 5. Compound 33 was prepared from intermediates 2-35 and 2-2 to give a white solid. Yield: 74%; $^1$H NMR (400 MHz, DMSO-$d_6$): δ 10.07 (br, NH, 1H), 8.55 (s, Ar—H, 1H), 8.51 (s, Ar—H, 1H), 7.87 (s, Ar—H, 1H), 7.54 (d, J=1.6 Hz, Ar—H, 1H), 6.78 (q, J=4.0 Hz, NH, 1H), 6.32 (d, J=1.6 Hz, Ar—H, 1H), 4.41-4.36 (m, CH, 1H), 3.67 (s, CH$_3$, 3H), 3.16 (dd, j=9.6 Hz, 2.0 Hz, CH$_2$, 1H), 2.93 (d, j=3.6 Hz, CH$_3$, 3H), 2.79-2.75 (m, CH$_2$, 1H), 2.64-2.59 (m, CH$_2$, 1H), 2.54-2.49 (m, CH$_2$, 1H), 2.11-2.07 (m, CH$_2$, 1H), 1.74-1.68 (m, CH$_2$, 1H), 1.63-1.56 (m, CH$_2$, 1H), 1.45-1.37 (m, CH$_2$, 1H); $^{13}$C NMR (100 MHz, DMSO-$d_6$): δ 160.55, 159.15, 157.30, 155.63, 142.41, 138.23, 135.67, 134.32, 116.34, 113.22, 108.60, 107.38, 101.53, 74.30, 49.78, 45.27, 36.50, 29.89, 28.14, 24.20; ESI-MS: m/z=406 [M+1]$^+$.

Preparative Example 22. Preparation of Compounds 34 to 43

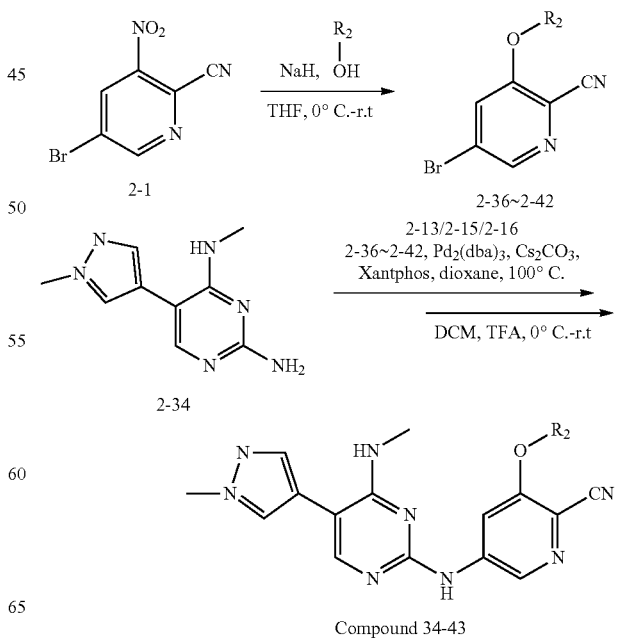

Compound 34-43

-continued

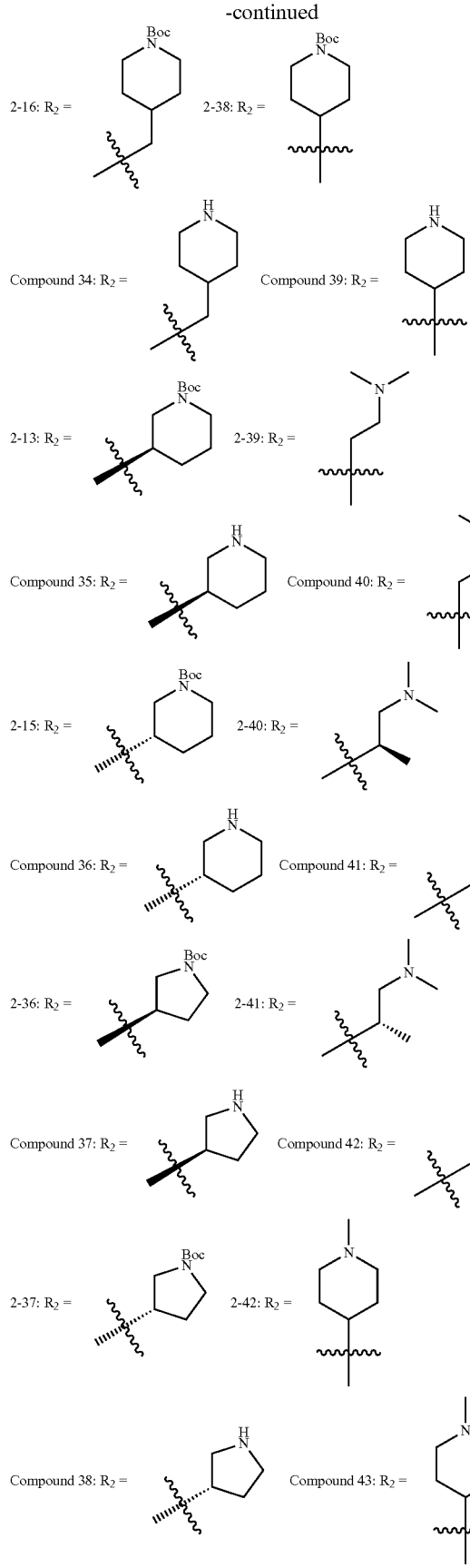

Step 1. Synthesis of Intermediates 2-36~2-42

Synthetic Procedure Reference Example 1, Step 1. Intermediates 2-36-2-42 were prepared by using 5-bromo-3-nitro-2-cyanopyridine (compound 2-1) and the corresponding alcohol as starting materials through a synthetic method similar to compound 1-2.

Step 2. Synthesis of Compound 34-43

Synthetic Procedure Reference Example 1, Step 5. Compounds 34-43 were prepared from 2-13, 2-15, 2-16, 2-36~2-42 and intermediate 2-34, respectively, to give white solids.

Preparative Example 23. $N^4$-Methyl-5-(4-methylthiazol-2-yl)-$N^2$-(2-cyano-3-(piperidin-3-yloxy)pyridin-5-yl)-2,4-diaminopyrimidine (Compound 44)

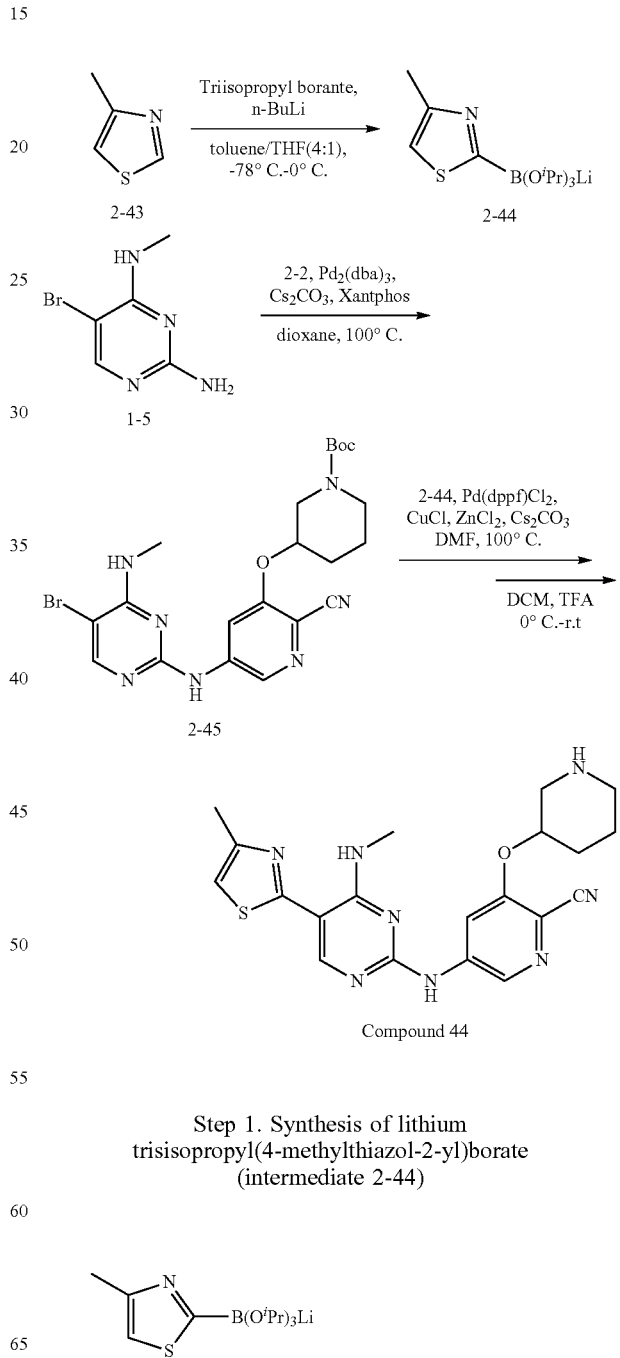

Step 1. Synthesis of lithium trisisopropyl(4-methylthiazol-2-yl)borate (intermediate 2-44)

4-Methylthiazole (1 g, 10.09 mmol), triisopropyl borate (2.35 mL, 10.09 mmol) was dissolved in a mixture of anhydrous toluene and THF (32 mL, v/v, 4:1) under nitrogen. Cooled to −78° C., n-butyl lithium (3.83 mL, 2.5 mol/L, 9.58 mmol) was added slowly within 85 min, and the reaction was stirred for 135 min. Slowly warmed to 0° C. (about 1.5 h), isopropanol (2.84 mL) was added and stirred overnight. The solvent was evaporated under reduced pressure, and anhydrous acetone (17 mL) was added, then evaporated. The mixture was filtered under a nitrogen atmosphere, washed with acetonitrile of 55° C., dried over vacuum to obtain a white solid, which was to be used directly in the next step without further purification.

Step 2. Synthesis of $N^4$-methyl-5-bromo-$N^2$-(2-cyano-3-(N-tert-butoxycarbonylpiperidin-3-yloxy) pyridin-5-yl)-2,4-diaminopyrimidine (intermediate 2-45)

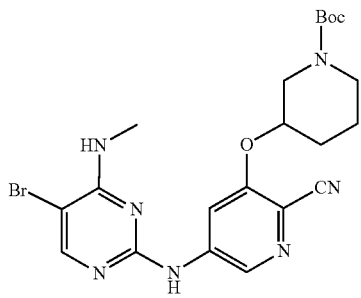 [SMILES: CNc1nc(Nc2cnc(C#N)c(OC3CCCN(C(=O)OC(C)(C)C)C3)c2)ncc1Br]

The synthetic procedure was described as Example 1, Step 5. The intermediate 2-45 was prepared from intermediates 1-5 and 2-2 to give a white solid. Yield: 70%; NMR (400 MHz, DMSO-$d_6$): δ 10.05 (s, NH, 1H), 8.46 (s, Ar—H, 1H), 8.41 (s, Ar—H, 1H), 8.13 (s, Ar—H, 1H), 7.32 (q, J=4.5 Hz, NH, 1H), 4.59 (br, CH, 1H), 3.96-3.93 (m, $CH_2$, 1H), 3.77-3.70 (m, $CH_2$, 1H), 3.54-3.43 (m, $CH_2$, 1H), 3.07-2.96 (m, $CH_2$, 1H), 2.93 (d, J=4.5 Hz, $CH_3$, 3H), 1.94 (br, $CH_2$, 2H), 1.85-1.80 (m, $CH_2$, 1H), 1.48-1.46 (m, $CH_2$, 1H), 1.38 (s, $CH_3×3$, 9H); ESI-MS: m/z=504 $[M+1]^+$.

Step 3. Synthesis of $N^4$-methyl-5-(4-methylthiazol-2-yl)-$N^2$-(2-cyano-3-(piperidin-3-yloxy)pyridin-5-yl)-2,4-diaminopyrimidine (Compound 44)

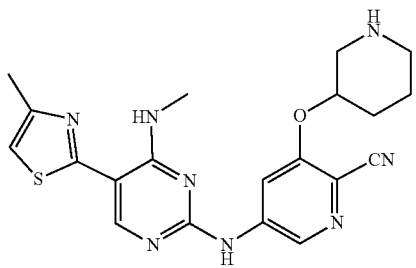 [SMILES: CNc1nc(Nc2cnc(C#N)c(OC3CCCNC3)c2)ncc1-c1nc(C)cs1]

Anhydrous DMF (10 mL) was added to a mixture of the compounds 2-45 (85.3 mg, 0.211 mmol), 2-44 (124 mg, 0.422 mmol), Pd(dppf)$Cl_2$ (7.7 mg, 0.011 mmol), CuCl (2.1 mg, 0.021 mmol), $ZnCl_2$ (28.8 mg, 0.211 mmol), $Cs_2CO_3$ (137.5 mg, 0.422 mmol) under nitrogen atmosphere. The reaction was heated to 100° C. and stirred overnight. After suction filtration, the solvent was removed under reduced pressure to give a residue, which was purified by column chromatography on silica gel (eluent $CH_2Cl_2$:EtOH=30:1) to afford a white solid. The obtained white solid was dissolved in dichloromethane (3 mL), trifluoroacetic acid (3 mL) was added dropwise, and the mixture was stirred for 30 minutes at ice-bath then stirred at room temperature for 4.5 hours. The mixture was neutralized to pH 9 with saturated sodium hydrogen carbonate solution. Ethyl acetate (40 mL) was added, and the organic layer was washed with saturated sodium chloride solution and dried over anhydrous sodium sulfate. The organic layer was evaporated under reduced pressure and the residue was purified by silica gel column chromatography, using $CH_2Cl_2$/EtOH($NH_3$) (100:3) as eluent to give a white solid. Yield: 40%; $^1$H NMR (400 MHz, DMSO-$d_6$): δ 10.05 (s, NH, 1H), 8.46 (s, Ar—H, 1H), 8.41 (s, Ar—H, 1H), 8.13 (s, Ar—H, 1H), 7.32 (q, J=4.5 Hz, NH, 1H), 4.59 (br, CH, 1H), 3.96-3.93 (m, $CH_2$, 1H), 3.77-3.70 (m, $CH_2$, 1H), 3.54-3.43 (m, $CH_2$, 1H), 3.07-2.96 (m, $CH_2$, 1H), 2.93 (d, J=4.5 Hz, $CH_3$, 3H), 1.94 (br, $CH_2$, 2H), 1.85-1.80 (m, $CH_2$, 1H), 1.48-1.46 (m, $CH_2$, 1H), 1.38 (s, $CH_3×3$, 9H); ESI-MS: m/z=504 $[M+1]^+$.

Preparative Example 24

5-Trifluoromethyl-N-(2-cyano-3-(piperidin-3-oxy) pyridin-5-yl)-2-aminopyrimidine (Compound 45)

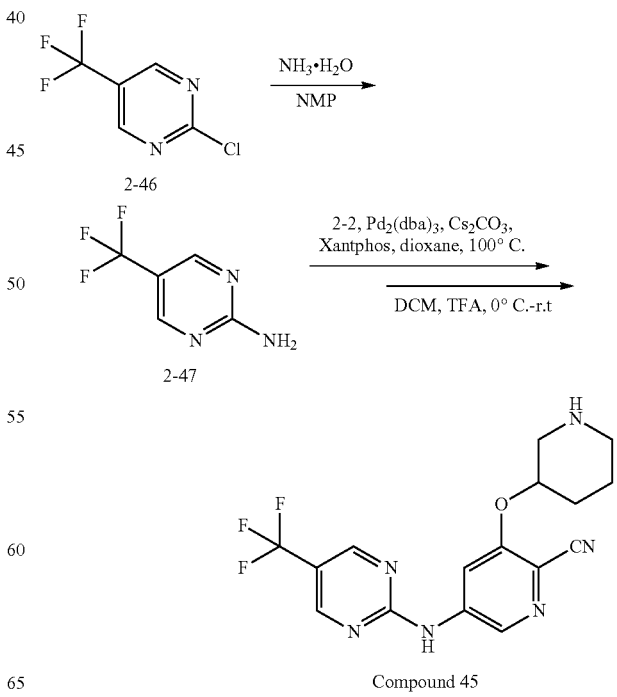

Compound 45

Step 1. Synthesis of 5-trifluoromethyl-2-aminopyrimidine (Intermediate 2-47)

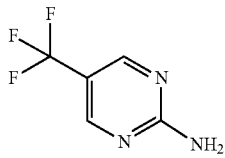

Compound 2-46 (225 mg, 1.23 mmol) was placed in a sealed tube, ammonium hydroxide (10 mL) and N-methylpyrrolidone (10 mL) were added, and the mixture was stirred at 120° C. for 24 h. After cooling to room temperature, the solvent was removed under reduced pressure to give a residue. Purified by silica gel column chromatography (eluent PE:EtOAc=2:1) to give a white solid. LC-MS: m/z=164 [M+1]$^+$.

Step 2. Synthesis of 5-trifluoromethyl-N-(2-cyano-3-(piperidin-3-oxy)pyridin-5-yl)-2-aminopyrimidine (Compound 45)

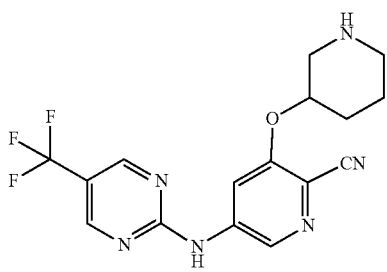 [SMILES: N#Cc1ncc(Nc2ncc(C(F)(F)F)cn2)cc1OC1CCCNC1]

Synthetic Procedure Reference Example 1, Step 5. Compound 45 was prepared from intermediates 2-47 and 2-2 to give a white solid. LC-MS: m/z=365 [M+1]$^+$.

Preparative Example 25. Preparation of Compound 46-50

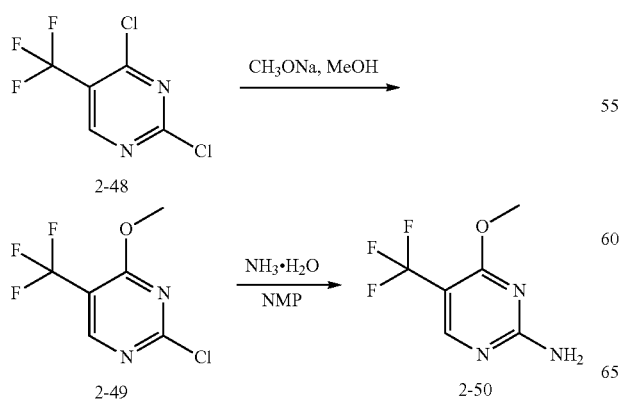

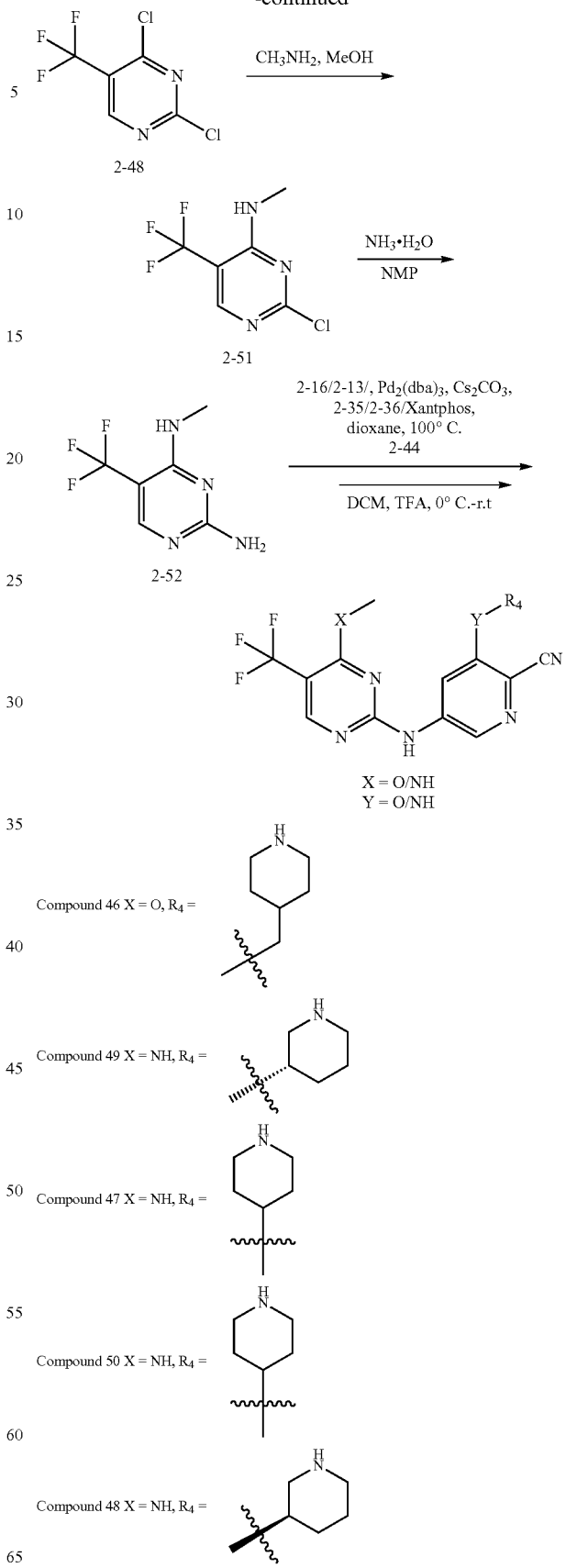

Step 1. Synthesis of Intermediate 2-49/2-51

The synthetic steps were carried out according to the same procedure as in Example 17, Step 2, and Example 1, Step 2, respectively, to obtain the compounds 2-49/2-51, and the mass spectral data were LC-MS: m/z=194 [M+1]⁺ and LC-MS: m/z=193 [M+1]⁺, respectively.

Step 2. Synthesis of Intermediates 2-50/2-52

The synthetic steps were carried out according to the same procedure as in Example 24, Step 1. Compound 2-50/2-52 was prepared from 2-49/2-51, respectively, to give a white solid. The mass spectral data were LC-MS: m/z=194 [M+1]⁺ and LC-MS: m/z=193[M+1]⁺, respectively.

Step 3. Synthesis of Compound 46-50

The procedure of synthesis was described as that of Example 5, Step 5. Compound 46-50 were prepared from 2-16, 2-13, 2-35, 2-44 and intermediate 2-50/2-52, respectively, to give white solids. The mass spectral data were LC-MS: m/z=409 [M+1]⁺, LC-MS: m/z=394 [M+1]⁺, LC-MS: m/z=394 [M+1]⁺, LC-MS: m/z=394 [M+1]⁺, and LC-MS: m/z=393 [M+1]⁺, respectively.

The NMR and MS data of the intermediates 2-21~2-33, 2-3~2-42, compounds 19-31, and 34-43 are shown in Table 1-1, 1-2, 1-3, 1-4.

TABLE 1-1

| Compounds Number | Name of the Compounds | Nuclear magnetic resonance and mass spectrometry data |
|---|---|---|
| Intermediate 2-21 | 5-phenyl-$N^4$-methyl-2, 4-diaminopyrimidine | $^1$H NMR (500 MHz, CDCl$_3$): δ 7.69 (br, Ar-H, 1H), 7.49 (d, J = 5.5 Hz, Ar-H, 2H), 7.13-7.09 (m, Ar-H, 3H), 6.43 (q, J = 4.5 Hz, NH, 1H), 6.25 (br, NH2, 2H), 2.85 (d, J = 4.5 Hz, CH$_3$, 3H); ESI-MS: m/z = 201 [M + 1]⁺ |
| Intermediate 2-22 | 5-(3-fluorophenyl)-$N^4$-methyl-2, 4-diaminopyrimidine | $^1$H NMR (500 MHz, CDCl$_3$): δ 7.60 (br, Ar-H, 1H), 7.47-7.43 (m, Ar-H, 1H), 7.16-7.11 (m, Ar-H, 3H), 6.36 (q, J = 4.5 Hz, NH, 1H), 6.21 (br, NH$_2$, 2H), 2.79 (d, J = 4.5 Hz, CH$_3$, 3H); ESI-MS: m/z = 219 [M + 1]⁺ |
| Intermediate 2-23 | 5-(4-fluorophenyl)-$N^4$-methyl-2, 4-diaminopyrimidine | $^1$H NMR (500 MHz, CDCl$_3$): δ 7.57 (s, Ar-H, 1H), 7.31 (d, J = 8.5 Hz, Ar-H, 2H), 7.07 (d, J = 8.5 Hz, Ar-H, 2H), 6.17 (q, J = 4.5 Hz, NH, 1H), 6.11 (br, NH$_2$, 2H), 2.85 (d, J = 4.5 Hz, CH$_3$, 3H); ESI-MS: m/z = 219 [M + 1]⁺ |
| Intermediate 2-24 | 5-(2-fluorophenyl)-$N^4$-methyl-2, 4-diaminopyrimidine | $^1$H NMR (500 MHz, CDCl$_3$): δ 7.49 (s, Ar-H, 1H), 7.41-7.37 (m, Ar-H, 1H), 7.30- 7.27 (m, Ar-H, 1H), 7.25-7.22 (m, Ar-H, 2H), 6.08 (br, NH, 2H), 6.04 (q, J = 4.5 Hz, NH), 2.75 (d, J = 4.5 Hz, CH$_3$, 3H); ESI-MS: m/z = 219 [M + 1]⁺ |
| Intermediate 2-25 | 5-(3 -methoxyphenyl)-$N^4$ -methyl-2, 4-diaminopyrimidine | $^1$H NMR (500 MHz, DMSO-d$_6$): δ 7.55 (s, Ar-H, 1H), 7.34-7.30 (m, Ar-H, 1H), 6.88-6.86 (m, Ar-H, 2H), 6.84 (s, Ar-H, 1H), 6.15 (q, J = 4.5 Hz, NH), 6.01 (br, NH, , 2H), 3.78 (s, CH$_3$, 3H), 2.77 (d, J = 4.5 Hz, CH$_3$, 3H); ESI-MS: m/z = 231 [M + 1]⁺ |
| Intermediate 2-26 | 5-(4-methoxyphenyl)-$N^4$-methyl-2, 4-diaminopyrimidine | $^1$H NMR (500 MHz, CDCl$_3$): δ 7.47 (s, Ar-H, 1H), 7.22 (d, J = 8.5 Hz, Ar-H, 2H), 6.99 (d, J = 8.5 Hz, Ar-H, 2H), 6.09 (q, J = 4.5 Hz, NH, 1H), 6.03 (br, NH$_2$, 2H), 3.77 (s, CH$_3$, 3H), 2.76 (d, J = 4.5 Hz, CH$_3$, 3H); ESI-MS: m/z = 231 [M + 1]⁺$_o$ |
| Intermediate 2-27 | 5 -(2, 4-dimethoxyphenyl) -$N^4$-methyl-2, 4-diaminopyrimidine | $^1$H NMR (400 MHz, CDCl$_3$): δ 7.35 (br, Ar-H, 1H), 6.99 (d, J = 8.0 Hz, Ar-H, 1H), 6.61 (s, Ar-H, 1H), 6.57 (d, J = 8.0 Hz, Ar-H, 1H), 5.87 (br, NH$_2$, 2H), 5.62 (br, NH, 1H), 3.79 (s, CH$_3$, 3H), 3.71 (s, CH$_3$, 3H), 2.72 (d, J = 4.5 Hz, CH$_3$, 3H); ESI-MS: m/z = 261 [M + 1]⁺ |
| Intermediate 2-28 | 5-(pyri din-3-yl)-$N^4$ -methyl-2, 4-diaminopyrimidine | $^1$H NMR (500 MHz, DMSO-d$_6$): δ 8.50 (br, Ar-H, 2H), 7.72 (d, J = 8.0 Hz, Ar-H, 1H), 7.56 (s, Ar-H, 1H), 7.43-7.40 (m, Ar-H, 1H), 6.35 (q, J = 4.5 Hz, NH, 1H), 6.14 (br, NH, , 2H), 2.76 (d, J = 4.5 Hz, CH$_3$, 3H); ESI-MS: mz = 202 [M + 1]⁺ |
| Intermediate 2-29 | 5-(pyridin-4-yl)-$N^4$-methyl--2, 4-diaminopyrimidine | $^1$H NMR (500 MHz, DMSO-d$_6$): δ 8.43 (br, Ar-H, 1H), 7.31 (d, J = 8.5 Hz, Ar-H, 2H), 7.08 (d, J = 8.5 Hz, Ar-H, 2H), 6.18 (q, J = 4.5 Hz, NH, 1H), 6.17 (br, NH$_2$, 2H), 2.82 (d, J = 4.5 Hz, CH$_3$, 3H); ESI-MS: m/z = 202 [M + 1]⁺ |
| Intermediate 2-30 | 5-(thien-2-yl)-$N^4$-methyl-2, 4-diaminopyrimidine | $^1$H NMR (500 MHz, DMSO-d$_6$): δ 7.66 (s, Ar-H, 1H), 7.51 (d, J = 4.5 Hz, Ar-H, 1H), 7.13-7.11 (m, Ar-H, 1H), 7.06 (d, J = 2.5 Hz, Ar-H, 1H), 6.30 (q, J = 4.5 Hz, NH, 1H), 6.21 (br, NH$_2$, 2H), 2.80 (d, J = 4.5 Hz, CH$_3$, 3H): ESI-MS: m/z = 207 [M + 1]⁺ |
| Intermediate 2-31 | 5-(furan-2-yl)-$N^4$-methyl-2, 4-diaminopyrimidine | $^1$H NMR (500 MHz, DMSO-d$_6$): δ 7.64 (s, Ar-H, 1H), 7.57-7.48 (m, Ar-H, 1H), 6.54 (br, Ar-H, 2H), 6.44 (q, J = 3.5 Hz, NH, 1H), 6.22 (br, NH, 2H), 2.86 (d, J = 4.5 Hz, CH$_3$, 3H); ESI-MS: m/z = 191 [M + 1]⁺ |

TABLE 1-1-continued

| Compounds Number | Name of the Compounds | Nuclear magnetic resonance and mass spectrometry data |
|---|---|---|
| Intermediate 2-33 | 5-(5-methoxycarbonylthien-2-yl)-$N^4$-methyl-2, 4-diaminopyrimidine | $^1$H NMR (500 MHz, DMSO-$d_6$): δ 7.78 (d, J = 4.0 Hz, Ar-H, 1H), 7.77 (s, Ar-H, 1H), 7.16 (d, J = 4.0 Hz, Ar-H, 1H), 6.56 (q, J = 4.5 Hz, NH, 1H), 6.40 (br, NH$_2$, 2H), 3.82 (s, CH$_3$, 3H), 2.80 (d, J = 4.5 Hz, CH$_3$, 3H); ESI-MS: m/z = 265 [M + 1]$^+$ |

TABLE 1-2

| Compounds Number | Name of the Compounds | Nuclear magnetic resonance and mass spectrometry data |
|---|---|---|
| Compound 19 | $N^4$-methyl-5-phenyl-$N^2$-(2-cyano-3-(piperidin-3-oxy)pyridin-5-yl)-2, 4-diaminopyrimidine | $^1$H NMR (500 MHz, DMSO-$d_6$): δ 9.96 (br, NH, 1H), 8.54 (s, Ar-H, 1H), 8.53 (s, Ar-H, 1H), 7.82 (s, Ar-H, 1H), 7.50-7.47 (m, Ar-H, 2H), 7.42-7.40 (m, Ar-H, 3H), 6.77 (q, J = 4.5 Hz, NH, 1H), 4.41-4.36 (m, CH, 1H), 3.16 (dd, J = 12.0 Hz, 2.0 Hz, CH$_2$, 1H), 2.93 (d, J = 4.5 Hz, CH$_3$, 3H), 2.79-2.75 (m, CH$_2$, 1H), 2.64-2.60 (m, CH$_2$, 1H), 2.54-2.49 (m, CH$_2$, 1H), 2.11-2.08 (m, CH$_2$, 1H), 1.75-1.69 (m, CH$_2$, 1H), 1.63-1.56 (m, CH$_2$, 1H), 1.46-1.38 (m, CH$_2$, 1H); 13c NMR (125 MHz, DMSO-$d_6$): δ 160.20, 158.17, 157.35, 153.93, 142.67, 134.67, 134.19, 129.02, 128.78, 127.46, 116.43, 112.85, 112.77, 108.20, 74.26, 49.78, 45.27, 29.89, 28.28, 24.19; ESI-MS: m/z = 402 [M + 1]$^+$ |
| Compound 20 | $N^4$-methyl-5-(3-fluorophenyl)-$N^2$-(2-cyano-3-(piperidin-3-yloxy)pyridin-5-yl)-2, 4-diaminopyrimidine | $^1$H NMR (500 MHz, DMSO-$d_6$): δ 10.03 (s, NH, 1H), 8.53 (d, J = 4.0 Hz, Ar-H, 2H), 7.86 (s, Ar-H, 1H), 7.54 (q, J = 6.5 Hz, Ar-H, 1H), 7.26-7.21 (m, Ar-H, 3H), 6.92 (q, J = 4.0 Hz, NH, 1H), 4.41-4.38 (m, CH, 1H), 3.16 (d, J = 10.5 Hz, CH$_2$, 1H), 2.92 (d, J = 4.5 Hz, CH$_3$, 3H), 2.78-2.76 (m, CH$_2$, 1H), 2.65-2.61 (m, CH$_2$, 1H), 2.55-2.53 (m, CH$_2$, 1H), 2.09 (br, CH$_2$, 1H), 1.73-1.71 (m, CH$_2$, 1H), 1.63-1.56 (m, CH$_2$, 1H), 1.45-1.39 (m, CH$_2$, 1H); $^{13}$C NMR (125 MHz, DMSO-$d_6$): δ 163.39, 161.45, 160.05, 158.36, 157.29, 154.18, 142.58, 137.13, 137.07, 134.25, 130.95, 130.88, 124.97, 116.40, 115.74, 115.57, 114.34, 114.17, 112.99, 111.62, 108.32, 74.07, 49.50, 45.13, 29.71, 28.26, 23.88; ESI-MS: m/z = 420 [M + 1]$^+$ |
| Compound 21 | $N^4$-methyl-5-(4-fluorophenyl)-$N^2$-(2-cyano-3-(piperidin-3-yloxy)pyridin-5-yl)-2, 4-diaminopyrimidine | $^1$H NMR (400 MHz, DMSO-$d_6$): δ 9.96 (br, NH, 1H), 8.53 (s, Ar-H, 1H), 8.52 (s, Ar-H, 1H), 7.80 (s, Ar-H, 1H), 7.44-7.41 (m, Ar-H, 2H), 7.31-7.28 (m, Ar-H, 2H), 6.77 (q, J = 4.6 Hz, NH, 1H), 4.40-4.35 (m, CH, 1H), 3.15 (dd, J = 12.0 Hz, 2.0 Hz, CH$_2$, 1H), 2.92 (d, J = 3.6 Hz, CH$_3$, 3H), 2.78-2.74 (m, CH$_2$, 1H), 2.63-2.59 (m, CH$_2$, 1H), 2.54-2.49 (m, CH$_2$, 1H), 2.11-2.07 (m, CH$_2$, 1H), 1.74-1.68 (m, CH$_2$, 1H), 1.63-1.56 (m, CH$_2$, 1H), 1.45-1.37 (m, CH$_2$, 1H); 13c NMR (100 MHz, DMSO-$d_6$): δ 162.64, 160.70, 160.32, 158.24, 157.34, 153.92, 142.64, 134.18, 131.08, 131.02, 116.41, 115.89, 115.72, 112.87, 111.90, 108.22, 74.28, 49.80, 45.28, 29.89, 28.22, 24.21; ESI-MS: mz = 420 [M + 1]$^+$ |
| Compound 22 | $N^4$-methyl-5-(2-fluorophenyl)-$N^2$-(2-cyano-3-(piperidin-3-oxy)pyridin-5-yl)-2, 4-diaminopyrimidine | $^1$H NMR (400 MHz, DMSO-$d_6$) δ 9.99 (br, NH, 1H), 8.55 (s, Ar-H, 1H), 8.53 (s, Ar-H, 1H), 7.82 (s, Ar-H, 1H), 7.50-7.45 (m, Ar-H, 1H), 7.40-7.37 (m, Ar-H, 1H), 7.33-7.29 (m, Ar-H, 2H), 6.73 (q, J = 3.6 Hz, NH, 1H), 4.42-4.37 (m, CH, 1H), 3.16 (dd, J = 9.6 Hz, 2.0 Hz, CH$_2$, 1H), 2.92 (d, J = 3.6 Hz, CH$_3$, 3H), 2.78-2.74 (m, CH$_2$, 1H), 2.64-2.60 (m, CH$_2$, 1H), 2.54-2.49 (m, CH$_2$, 1H), 2.11-2.08 (m, CH$_2$, 1H), 1.73-1.70 (m, CH$_2$, 1H), 1.64-1.57 (m, CH$_2$, 1H), 1.46-1.38 (m, CH$_2$, |

TABLE 1-2-continued

| Compounds Number | Name of the Compounds | Nuclear magnetic resonance and mass spectrometry data |
|---|---|---|
| | | 1H); $^{13}$C NMR (100 MHz, DMSO-d$_6$): δ 160.92, 160.29, 158.97, 158.69, 157.33, 154.77, 142.58, 134.24, 132.09, 130.10, 130.03, 124.92, 122.03, 121.90, 116.38, 116.08, 115.91, 112.99, 108.40, 106.78, 74.30, 49.79, 45.28, 29.88, 28.15, 24.20; ESI-MS: mz = 420 [M + 1]$^+$ |
| Compound 23 | N$^4$-methyl-5-(3-methoxyphenyl)-N$^2$-(2-cyano-3-(piperidin-3-yloxy)pyridin-5-yl)-2, 4-diaminopyrimidine | $^1$H NMR (400 MHz, DMSO-d$_6$): δ 9.96 (br, NH, 1H), 8.54 (s, Ar-H, 1H), 8.53 (s, Ar-H, 1H), 7.84 (s, Ar-H, 1H), 7.40-7.37 (m, Ar-H, 1H), 6.97-6.95 (m, Ar-H, 3H), 6.79 (q, J = 3.6 Hz, NH, 1H), 4.40-4.35 (m, CH, 1H), 3.81 (s, CH$_3$, 3H), 3.16 (dd, J = 9.6 Hz, 1.6 Hz, CH$_2$, 1H), 2.94 (d, J = 3.6 Hz, CH$_3$, 3H), 2.79-2.74 (m, CH$_2$, 1H), 2.63-2.59 (m, CH$_2$, 1H), 2.54 (dd, J = 17.6 Hz, 2.4 Hz, CH$_2$, 1H), 2.11-2.08 (m, CH$_2$, 1H), 1.74-1.68 (m, CH$_2$, 1H), 1.63-1.56 (m, CH$_2$, 1H), 1.46-1.37 (m, CH$_2$, 1H); $^{13}$C NMR (100 MHz, DMSO-d$_6$):δ160.14, 159.60, 158.16, 157.34, 153.81, 142.65, 135.97, 134.17, 130.06, 120.92, 116.41, 114.06, 113.33, 112.85, 112.66, 108.19, 74.29, 55.01, 49.82, 45.29, 29.91, 28.26, 24.23; ESI-MS: m/z = 432 [M + 1]$^+$ |
| Compound 24 | N$^4$-methyl-5-(4-methoxyphenyl)-N$^2$-(2-cyano-3-(piperidin-3-yloxy)pyridin-5-yl)-2, 4-diaminopyrimidine | $^1$H NMR (400 MHz, DMSO-d$_6$): δ 9.92 (s, NH, 1H), 8.53 (s, Ar-H, 2H), 7.77 (s, Ar-H, 1H), 7.32 (d, J = 7.2 Hz, Ar-H, 2H), 7.05 (d, J = 7.2 Hz, Ar-H, 2H), 6.68 (q, J = 3.6 Hz, NH, 1H), 4.40-4.35 (m, CH, 1H), 3.80 (s, CH$_3$, 3H), 3.15 (dd, J = 9.6 Hz, 1.6 Hz, CH$_2$, 1H), 2.92 (d, J = 3.6 Hz, CH$_3$, 3H), 2.78-2.74 (m, CH$_2$, 1H), 2.63-2.59 (m, CH$_2$, 1H), 2.54-2.49 (m, CH$_2$, 1H), 2.11-2.07 (m, CH$_2$, 1H), 1.74-1.68 (m, CH$_2$, 1H), 1.63-1.56 (m, CH$_2$, 1H), 1.45-1.37 (m, CH$_2$, 1H); $^{13}$C NMR (100 MHz, DMSO-d$_6$): δ 160.44, 158.74, 157.97, 157.35, 153.56, 142.72, 134.14, 130.07, 126.64, 116.64, 114.48, 112.74, 112.59, 108.09, 74.27, 55.15, 49.82, 45.29, 29.90, 28.25, 24.22; ESI-MS: m/z = 432 [M + 1]$^+$ |
| Compound 25 | N$^4$-methyl-5-(2, 4-dimethoxyphenyl)-N$^2$-(2-cyano-3-(piperidin-3-yloxy)pyridin-5-yl)-2, 4-diaminopyrimidine | $^1$H NMR (400 MHz, DMSO-d$_6$): δ 9.88 (s, NH, 1H), 8.55 (s, Ar-H, 1H), 8.53 (s, Ar-H, 1H), 7.66 (s, Ar-H, 1H), 7.09 (d, J = 6.8 Hz, Ar-H, 1H), 6.67 (s, Ar-H, 1H), 6.62 (d, J = 6.8 Hz, Ar-H, 1H), 6.33 (q, J = 3.6 Hz, NH, 1H), 4.41-4.36 (m, CH, 1H), 3.82 (s, CH$_3$, 3H), 3.75 (s, CH$_3$, 3H), 3.16 (dd, J = 9.6 Hz, 1.6 Hz, CH$_2$, 1H), 2.90 (d, J = 3.6 Hz, CH$_3$, 3H), 2.79-2.74 (m, CH$_2$, 1H), 2.64-2.60 (m, CH$_2$, 1H), 2.54-2.50 (m, CH$_2$, 1H), 2.11-2.08 (m, CH$_2$, 1H), 1.73-1.70 (m, CH$_2$, 1H), 1.63-1.56 (m, CH$_2$, 1H), 1.45-1.37 (m, CH$_2$, 1H); $^{13}$C NMR (100 MHz, DMSO-d$_6$): δ 160.74, 160.71, 158.25, 158.11, 157.37, 154.11, 142.85, 134.14, 131.90, 116.48, 115.27, 112.61, 109.92, 108.01, 105.31, 98.90, 74.20, 55.36, 55.27, 49.76, 45.25, 29.87, 28.16, 24.15; ESI-MS: m/z = 462 [M + 1]$^+$ |
| Compound 26 | N$^4$-methyl-5-(pyridin-3-yl)-N$^2$-(2-cyano-3-(piperidin-3-yloxy)pyridin-5-yl)-2, 4-diaminopyrimidine | $^1$H NMR (400 MHz, DMSO-d$_6$): δ 10.00 (br, NH, 1H), 8.60-8.58 (m, Ar-H, 2H), 8.55 (s, Ar-H, 1H), 8.52 (s, Ar-H, 1H), 7.86 (s, Ar-H, 1H), 7.83-7.81 (m, Ar-H, 1H), 7.50-7.47 (m, Ar-H, 1H), 6.98 (q, J = 3.6 Hz, NH, 1H), 4.40-4.35 (m, CH, 1H), 3.16 (dd, J = 9.6 Hz, 2.0 Hz, CH$_2$, 1H), 2.92 (d, J = 3.6 Hz, CH$_3$, 3H), 2.79-2.75 (m, CH$_2$, 1H), 2.64-2.60 (m, CH$_2$, 1H), 2.54-2.49 (m, CH$_2$, 1H), 2.11-2.08 (m, CH$_2$, 1H), 1.75-1.69 (m, CH$_2$, 1H), 1.63-1.56 (m, CH$_2$, 1H), 1.46-1.38 (m, CH$_2$, 1H); $^{13}$C NMR(100 MHz, DMSO-de)-. 5 160.37, 158.58, 157.32, 154.50, 149.46, 148.44, 142.54, 136.55, 134.22, |

TABLE 1-2-continued

| Compounds Number | Name of the Compounds | Nuclear magnetic resonance and mass spectrometry data |
|---|---|---|
| | | 130.70, 123.84, 116.37, 113.01, 109.51, 108.36, 74.31, 49.81, 45.29, 29.90, 28.20, 24.22; ESI-MS: m/z = 403 [M + 1]$^+$ |
| Compound 27 | $N^4$-methyl-5-(pyridin-4-yl)-$N^2$-(2-cyano-3-(piperidin-3-yloxy)pyridin-5-yl)-2, 4-diaminopyrimidine | $^1$H NMR (400 MHz, DMSO-d$_6$): δ 10.06 (br, NH, 1H), 8.64 (d, J = 4.8 Hz, Ar-H, 2H), 8.55 (s, Ar-H, 1H), 8.50 (s, Ar-H, 1H), 7.94 (s, Ar-H, 1H), 7.46 (d, J = 4.8 Hz, Ar-H, 2H), 7.06 (q, J = 3.6 Hz, NH, 1H), 4.41-4.36 (m, CH, 1H), 3.16 (dd, J = 9.6 Hz, 2.0 Hz, CH$_2$, 1H), 2.94 (d, J = 3.6 Hz, CH$_3$, 3H), 2.79-2.75 (m, CH$_2$, 1H), 2.64-2.60 (m, CH$_2$, 1H), 2.55-2.51 (m, CH$_2$, 1H), 2.11-2.08 (m, CH$_2$, 1H), 1.73-1.71 (m, CH$_2$, 1H), 1.63-1.56 (m, CH$_2$, 1H), 1.46-1.39 (m, CH$_2$, 1H); $^{13}$C NMR (100 MHz, DMSO-d$_6$): δ 160.30, 159.20, 157.80, 155.17, 150.59, 143.14, 142.91, 134.78, 123.90, 116.85, 113.68, 110.59, 109.00, 74.78, 50.26, 45.77, 30.37, 28.76, 24.68; ESI-MS: m/z = 403 [M + 1]$^+$ |
| Compound 28 | $N^4$-methyl-5-(thien-2-yl)-$N^2$-(2-cyano-3-(piperidin-3-oxy)pyridin-5-yl)-2, 4-diaminopyrimidine | $^1$H NMR (400 MHz, DMSO-d$_6$): δ 10.05 (br, NH, 1H), 8.53 (s, Ar-H, 1H), 8.51 (s, Ar-H, 1H), 7.96 (s, Ar-H, 1H), 7.63 (d, J = 4.0 Hz, Ar-H, 1H), 7.22-7.19 (m, Ar-H, 2H), 6.95 (q, J = 3.6 Hz, NH, 1H), 4.41-4.37 (m, CH, 1H), 3.16 (dd, J = 9.6 Hz, 2.0 Hz, CH$_2$, 1H), 2.97 (d, J = 3.6 Hz, CH$_3$, 3H), 2.79-2.75 (m, CH$_2$, 1H), 2.63-2.59 (m, CH$_2$, 1H), 2.54-2.49 (m, CH$_2$, 1H), 2.11-2.08 (m, CH$_2$, 1H), 1.73-1.70 (m, CH$_2$, 1H), 1.63-1.56 (m, CH$_2$, 1H), 1.46-1.38 (m, CH$_2$, 1H); $^{13}$C NMR (100 MHz, DMSO-d$_6$): δ 160.12, 158.32, 157.34, 154.46, 142.45, 135.46, 134.25, 128.11, 126.62, 126.02, 116.40, 113.09, 108.40, 105.78, 74.29, 49.83, 45.32, 29.93, 28.39, 24.26; ESI-MS: m/z = 408 [M + 1]$^+$ |
| Compound 29 | $N^4$-methyl-5-(furan-2-yl)-$N^2$-(2-cyano-3-(piperidin-3-yloxy)pyridin-5-yl)-2, 4-diaminopyrimidine | $^1$H NMR (400 MHz, DMSO-d$_6$): δ 10.07 (br, NH, 1H), 8.53 (d, J = 1.6 Hz, Ar-H, 1H), 8.48 (d, J = 1.6 Hz, Ar-H, 1H), 8.25 (s, Ar-H, 1H), 7.75 (s, Ar-H, 1H), 7.07 (q, J = 3.6 Hz, NH, 1H), 6.77 (d, J = 2.8 Hz, Ar-H, 1H), 6.63-6.62 (m, Ar-H, 1H), 4.41-4.37 (m, CH, 1H), 3.16 (dd, J = 9.6 Hz, 2.0 Hz, CH$_2$, 1H), 3.04 (d, J = 3.6 Hz, CH$_3$, 3H), 2.80-2.76 (m, CH$_2$, 1H), 2.64-2.60 (m, CH$_2$, 1H), 2.55-2.53 (m, CH$_2$, 1H), 2.11-2.08 (m, CH$_2$, 1H), 1.75-1.69 (m, CH$_2$, 1H), 1.64-1.57 (m, CH$_2$, 1H), 1.47-1.39 (m, CH$_2$, 1H); ESI-MS: m/z = 392 [M + 1]$^+$ |
| Compound 30 | $N^4$-methyl-5-(5-chloro-furan-2-yl)-$N^2$-(2-cyano-3-(piperidin-3-yloxy)pyridin-5-yl)-2, 4-diaminopyrimidine | $^1$H NMR (400 MHz, DMSO-d$_6$): δ 10.07 (br, NH, 1H), 8.53 (d, J = 1.6 Hz, Ar-H, 1H), 8.48 (d, J = 1.6 Hz, Ar-H, 1H), 8.25 (s, Ar-H, 1H), 7.75 (s, Ar-H, 1H), 7.07 (q, J = 3.6 Hz, NH, 1H), 6.77 (d, J = 2.8 Hz, Ar-H, 1H), 6.63-6.62 (m, Ar-H, 1H), 4.41-4.37 (m, CH, 1H), 3.16 (dd, J = 9.6 Hz, 2.0 Hz, CH$_2$, 1H), 3.04 (d, J = 3.6 Hz, CH$_3$, 3H), 2.80-2.76 (m, CH$_2$, 1H), 2.64-2.60 (m, CH$_2$, 1H), 2.55-2.53 (m, CH$_2$, 1H), 2.11-2.08 (m, CH$_2$, 1H), 1.75-1.69 (m, CH$_2$, 1H), 1.64-1.57 (m, CH$_2$, 1H), 1.47-1.39 (m, CH$_2$, 1H); ESI-MS: mz = 426 [M + 1]$^+$ |
| Compound 31 | $N^4$-methyl-5-(5-methoxycarbonylthien-2-yl)-$N^2$-(2-cyano-3-(piperidin-3-yloxy)pyridin-5-yl)-2, 4-diaminopyrimidine | $^1$H NMR (400 MHz, DMSO-d$_6$): δ 10.10 (br, NH, 1H), 8.53 (s, Ar-H, 1H), 8.46 (s, Ar-H, 1H), 8.03 (s, Ar-H, 1H), 7.83 (d, J = 3.2 Hz, Ar-H, 1H), 7.29 (d, J = 2.8 Hz, Ar-H, 1H), 7.12 (q, J = 3.2 Hz, NH, 1H), 4.39-4.36 (m, CH, 1H), 3.86 (s, CH$_3$, 3H), 3.17 (dd, J = 9.6 Hz, 1.6 Hz, CH$_2$, 2H), 2.97 (d, J = 3.2 Hz, CH$_3$, 3H), 2.80-2.77 (m, CH$_2$, 1H), 2.65-2.61 (m, CH$_2$, 1H), 2.10-2.08 (m, CH$_2$, 1H), 1.74-1.71 (m, CH$_2$, 1H), 1.64-1.57 (m, CH$_2$, 1H), 1.47-1.39 (m, CH$_2$, 1H); $^{13}$C NMR (100 MHz, DMSO-d$_6$): δ 161.67, 159.83, 158.71, 157.26, 155.02, 143.51, 142.20, 134.40, 131.32, 127.40, 116.34, |

TABLE 1-2-continued

| Compounds Number | Name of the Compounds | Nuclear magnetic resonance and mass spectrometry data |
|---|---|---|
| | | 113.37, 108.61, 104.83, 74.25, 52.23, 49.76, 45.30, 29.88, 28.40, 24.17. ESI-MS: m/z = 466 [M + 1]$^+$ |

TABLE 1-3

| Compounds Number | Name of the Compounds | Nuclear magnetic resonance and mass spectrometry data |
|---|---|---|
| Intermediate 2-36 | (R)-2-cyano-5-bromo-3-(N-tert-butoxycarbonylpyrrole-3-yloxy)pyridine | $^1$H NMR (500 MHz, DMSO-d$_6$): δ 8.48 (d, J = 2.0 Hz, Ar-H, 1H), 8.29 (s, Ar-H, 1H), 5.32 (br, CH, 1H), 3.62-3.55 (m, CH, 1H), 3.49-3.44 (m, CH$_2$, 2H), 3.39-3.33 (m, CH$_2$, 1H), 2.21-2.16 (m, CH$_2$, 1H), 2.13-2.09 (m, CH$_2$, 1H), 1.41 (s, CH$_3$ × 3, 9H) ; ESI-MS: m/z = 368 [M + 1]$^+$ |
| Intermediate 2-37 | (S)-2-cyano-5-bromo-3-(N-tert-butoxycarbonylpyrrole-3-yloxy)pyridine | $^1$H NMR (500 MHz, DMSO-d$_6$): δ 8.48 (d, J = 2.0 Hz, Ar-H, 1H), 8.29 (s, Ar-H, 1H), 5.32 (br, CH, 1H), 3.62-3.55 (m, CH, 1H), 3.49-3.44 (m, CH$_2$, 2H), 3.39-3.33 (m, CH$_2$, 1H), 2.21-2.16 (m, CH$_2$, 1H), 2.13-2.09 (m, CH$_2$, 1H), 1.41 (s, CH$_3$ × 3, 9H) ; ESI-MS: m/z = 368 [M + 1]$^+$ |
| Intermediate 2-38 | 2-cyano-5-bromo-3-(N-tert-butoxycarbonylpiperidin-4-yloxy)pyridine | $^1$H NMR (500 MHz, CDCl$_3$): δ 8.34 (s, Ar-H, 1H), 7.51 (s, Ar-H, 1H), 4.66-4.62 (m, CH, 1H), 3.69-3.63 (m, CH$_2$, 2H), 3.52-3.46 (m, CH$_2$, 2H), 1.99-1.92 (m, CH$_2$, 2H), 1.90-1.82 (m, CH$_2$, 2H), 1.47 (s, CH$_3$ × 3, 9H); ESI-MS: m/z = 382 [M + 1]$^+$ |
| Intermediate 2-39 | 2-cyano-5-bromo-3-(2-dimethylamino)ethoxypyridine | $^1$H NMR (500 MHz, CDCl$_3$): δ 8.27 (s, Ar-H, 1H), 7.49 (s, Ar-H, 1H), 4.16 (t, J = 7.0 Hz, CH$_2$, 2H), 2.78 (t, J = 7.0 Hz, CH$_2$, 2H), 2.31 (s, CH$_3$ × 2, 6H); ESI-MS: m/z = 270 [M + 1]$^+$ |
| Intermediate 2-40 | (R)-2-cyano-5-bromo-3-(1-(dimethylamino)propyl-2-oxy)pyridine | $^1$H NMR (500 MHz, CDCl$_3$): δ 8.31 (s, Ar-H, 1H), 7.62 (s, Ar-H, 1H), 4.62-4.55 (m, CH, 1H), 2.76-2.71 (m, CH$_2$, 1H), 2.54-2.49 (m, CH$_2$, 1H), 2.31 (s, CH$_3$ × 2, 6H), 1.40 (d, J = 8.0 Hz, CH$_3$, 3H); ESI-MS: m/z = 284 [M + 1]$^+$ |
| Intermediate 2-41 | (S)-2-cyano-5-bromo-3-(1-(dimethylamino)propyl-2-oxy)pyridine | $^1$H NMR (500 MHz, CDCl$_3$): δ 8.31 (s, Ar-H, 1H), 7.62 (s, Ar-H, 1H), 4.62-4.55 (m, CH, 1H), 2.76-2.71 (m, CH$_2$, 1H), 2.54-2.49 (m, CH$_2$, 1H), 2.31 (s, CH$_3$ × 2, 6H), 1.40 (d, J = 8.0 Hz, CH$_3$, 3H); ESI-MS: m/z = 284 [M + 1]$^+$ |

TABLE 1-4

| Compounds Number | Name of the Compounds | Nuclear magnetic resonance and mass spectrometry data |
|---|---|---|
| Compound 34 | N$^4$-methyl-5-(1-methyl-1H-pyrazol-4-yl)-N$^2$-(2-cyano-3-(piperidin-4-methyl)oxypyridin-5-yl)-2,4-diaminopyrimidine | $^1$H NMR (400 MHz, DMSO-d$_6$): δ 9.96 (br, NH, 1H), 8.60 (s, Ar-H, 1H), 8.42 (s, Ar-H, 1H), 7.90 (s, Ar-H, 1H), 7.89 (s, Ar-H, 1H), 7.62 (s, Ar-H, 1H), 6.71 (q, J = 4.4 Hz, NH, 1H), 3.95 (d, J = 6.4 Hz, CH$_2$, 2H), 3.89 (s, CH$_3$, 3H), 2.99-2.96 (m, CH$_2$, 2H), 2.94 (d, J = 4.4 Hz, CH$_3$, 3H), 2.52-2.47 (m, CH$_2$, 2H), 1.89-1.86 (m, CH, 1H), 1.71-1.68 (m, CH$_2$, 2H), 1.22-1.12 (m, CH$_2$, 2H); ESI-MS: m/z = 420 [M + 1]$^+$ |

TABLE 1-4-continued

| Compounds Number | Name of the Compounds | Nuclear magnetic resonance and mass spectrometry data |
|---|---|---|
| Compound 35 | (R)-N$^4$-methyl-5-(1-methyl-1H-pyrazol-4-yl)-N$^2$-(2-cyano-3-(piperidin-3-yloxy)pyridin-5-yl)-2,4-diaminopyrimidine | $^1$H NMR (400 MHz, DMSO-d$_6$): δ 9.91 (s, NH, 1H), 8.52 (s, Ar-H, 1H), 8.51 (s, Ar-H, 1H), 7.91 (s, Ar-H, 1H), 7.90 (s, Ar-H, 1H), 7.61 (s, Ar-H, 1H), 6.73 (q, J = 4.0 Hz, NH, 1H), 4.40-4.35 (m, CH, 1H), 3.89 (s, CH$_3$, 3H), 3.15 (dd, J = 9.6 Hz, 2.0 Hz, CH$_2$, 1H), 2.95 (d, J = 3.6 Hz, CH$_3$, 3H), 2.79-2.75 (m, CH$_2$, 1H), 2.64-2.60 (m, CH$_2$, 1H), 2.54-2.51 (m, CH$_2$, 1H), 2.11-2.07 (m, CH$_2$, 1H), 1.75-1.69 (m, CH$_2$, 1H), 1.63-1.56 (m, CH$_2$, 1H), 1.46-1.38 (m, CH$_2$, 1H); $^{13}$C NMR (100 MHz, DMSO-d$_6$): δ 160.27, 157.75, 157.37, 153.08, 142.73, 137.65, 134.13, 129.42, 116.48, 113.78, 112.70, 108.03, 104.51, 74.25, 49.80, 45.30, 38.65, 29.90, 28.28, 24.20; ESI-MS: m/z = 406 [M + 1]$^+$ |
| Compound 36 | (S)-N$^4$-methyl-5-(1-methyl-1H-pyrazol-4-yl)-N$^2$-(2-cyano-3-(piperidin-3-yloxy)pyridin-5-yl)-2,4-diaminopyrimidine | $^1$H NMR (400 MHz, DMSO-d$_6$): δ 9.91 (s, NH, 1H), 8.52 (s, Ar-H, 1H), 8.51 (s, Ar-H, 1H), 7.91 (s, Ar-H, 1H), 7.90 (s, Ar-H, 1H), 7.61 (s, Ar-H, 1H), 6.73 (q, J = 4.0 Hz, NH, 1H), 4.40-4.35 (m, CH, 1H), 3.89 (s, CH$_3$, 3H), 3.15 (dd, J = 9.6 Hz, 2.0 Hz, CH$_2$, 1H), 2.95 (d, J = 3.6 Hz, CH$_3$, 3H), 2.79-2.75 (m, CH$_2$, 1H), 2.64-2.60 (m, CH$_2$, 1H), 2.54-2.51 (m, CH$_2$, 1H), 2.11-2.07 (m, CH$_2$, 1H), 1.75-1.69 (m, CH$_2$, 1H), 1.63-1.56 (m, CH$_2$, 1H), 1.46-1.38 (m, CH$_2$, 1H); $^{13}$C NMR (100 MHz, DMSO-d$_6$): δ 160.27, 157.75, 157.37, 153.08, 142.73, 137.65, 134.13, 129.42, 116.48, 113.78, 112.70, 108.03, 104.51, 74.25, 49.80, 45.30, 38.65, 29.90, 28.28, 24.20; ESI-MS: m/z = 406 [M + 1]$^+$ |
| Compound 37 | (R)-N$^4$-methyl-5-(1-methyl-1H-pyrazol-4-yl)-N$^2$-(2-cyano-3-(pyrrole-3-oxy)pyridin-5-yl)-2,4-diaminopyrimidine | $^1$H NMR (400 MHz, DMSO-d$_6$): δ 9.92 (br, NH, 1H), 8.60 (s, Ar-H, 1H), 8.39 (s, Ar-H, 1H), 7.91 (s, Ar-H, 2H), 7.62 (s, Ar-H, 1H), 6.72 (q, J = 4.4 Hz, NH, 1H), 4.96 (br, CH, 1H), 3.89 (s, CH$_3$, 3H), 3.16 (dd, J = 12.4 Hz, 5.2 Hz, CH$_2$, 1H), 2.94-2.93 (m, CH$_2$, 2H), 2.92 (d, J = 4.4 Hz, CH$_3$, 3H), 2.83-2.79 (m, CH$_2$, 1H), 2.10-2.02 (m, CH$_2$, 1H), 1.87-1.84 (m, CH$_2$, 1H); $^{13}$C NMR (100 MHz, DMSO-d$_6$): δ 160.28, 157.72, 157.58, 152.97, 142.66, 137.65, 133.79, 129.43, 116.48, 113.76, 112.41, 107.91, 104.64, 80.01, 52.80, 45.48, 38.66, 33.25, 28.15; ESI-MS: m/z = 392 [M + 1]$^+$ |
| Compound 38 | (S)-N$^4$-methyl-5-(1-methyl-1H-pyrazol-4-yl)-N$^2$-(2-cyano-3-(pyrrole-3-oxy)pyridin-5-yl)-2,4-diaminopyrimidine | $^1$H NMR (400 MHz, DMSO-d$_6$): δ 9.92 (br, NH, 1H), 8.60 (s, Ar-H, 1H), 8.39 (s, Ar-H, 1H), 7.91 (s, Ar-H, 2H), 7.62 (s, Ar-H, 1H), 6.72 (q, J = 4.4 Hz, NH, 1H), 4.96 (br, CH, 1H), 3.89 (s, CH$_3$, 3H), 3.16 (dd, J = 12.4 Hz, 5.2 Hz, CH$_2$, 1H), 2.94-2.93 (m, CH$_2$, 2H), 2.92 (d, J = 4.4 Hz, CH$_3$, 3H), 2.83-2.79 (m, CH$_2$, 1H), 2.10-2.02 (m, CH$_2$, 1H), 1.87-1.84 (m, CH$_2$, 1H); ESI-MS: m/z = 392 [M + 1]$^+$ |
| Compound 39 | N$^4$-methyl-5-(1-methyl-1H-pyrazol-4-yl)-N$^2$-(2-cyano-3-(piperidin-4-yloxy)pyridin-5-yl)-2,4-diaminopyrimidine | $^1$H NMR (400 MHz, DMSO-d$_6$): δ 9.90 (s, NH, 1H), 8.53 (s, Ar-H, 1H), 8.47 (s, Ar-H, 1H), 7.91 (s, Ar-H, 1H), 7.90 (s, Ar-H, 1H), 7.61 (s, Ar-H, 1H), 6.73 (q, J = 4.8 Hz, NH, 1H), 4.58-4.54 (m, CH, 1H), 3.88 (s, CH$_3$, 3H), 3.00-2.96 (m, CH$_2$, 2H), 2.94 (d, J = 4.8 Hz, CH$_3$, 3H), 2.58-2.53 (m, CH$_2$, 2H), 1.96-1.92 (m, CH$_2$, 2H), 1.61-1.53 (m, CH$_2$, 2H); ESI-MS: m/z = 406 [M + 1]$^+$ |
| Compound 40 | N$^4$-methyl-5-(1-methyl-1H-pyrazol-4-yl)-N$^2$-(2-cyano-3-(2-dimethylaminoethoxy)pyridin-5-yl)-2,4-diaminopyrimidine | $^1$H NMR (400 MHz, DMSO-d$_6$): δ 9.96 (s, NH, 1H), 8.56 (s, Ar-H, 1H), 8.48 (s, Ar-H, 1H), 7.91 (s, Ar-H, 1H), 7.90 (s, Ar-H, 1H), 7.61 (s, Ar-H, 1H), 6.73 (q, J = 4.4 Hz, NH, 1H), 4.24 (t, J = 5.6 Hz, CH$_2$, 2H), 3.88 (s, CH$_3$, 3H), 2.94 (d, J = 4.8 Hz, CH$_3$, 3H), 2.72 (t, J = 5.6 Hz, CH$_2$, 2H), 2.25 (s, CH$_3$ × 2, 6H); $^{13}$C NMR(100 MHz, DMSO-d) : δ 160.22, 158.43, 157.73, 153.05, 142.82, 137.60, 133.83, 129.37, |

TABLE 1-4-continued

| Compounds Number | Name of the Compounds | Nuclear magnetic resonance and mass spectrometry data |
|---|---|---|
| Compound 41 | (R)-$N^4$-methyl-5-(1-methyl-1H-pyrazol-4-yl)-$N^2$-(2-cyano-3-(1-dimethylaminopropyl-2-oxy)pyridin-5-yl)-2,4-diaminopyrimidine | 116.42, 113.77, 111.72, 106.92, 104.53, 66.99, 57.06, 45.54, 38.63, 28.17; ESI-MS: mz = 394 [M + 1]$^+$ $^1$H NMR (400 MHz, DMSO-$d_6$): δ 9.94 (s, NH, 1H), 8.54 (s, Ar-H, 2H), 7.92 (s, Ar-H, 1H), 7.91 (s, Ar-H, 1H), 7.63 (s, Ar-H, 1H), 6.74 (q, J = 4.4 Hz, NH, 1H), 4.69-4.65 (m, CH, 1H), 3.91 (s, $CH_3$, 3H), 2.96 (d, J = 4.4 Hz, $CH_3$, 3H), 2.63-2.58 (m, $CH_2$, 1H), 2.53-2.48 (m, $CH_2$, 1H), 2.24 (s, $CH_3$ × 2, 6H), 1.35 (d, J = 6.0 Hz, $CH_3$, 3H); ESI-MS: m/z = 408 [M + 1]$^+$ |
| Compound 42 | (S)-$N^4$-methyl-5-(1-methyl-1H-pyrazol-4-yl)-$N^2$-(2-cyano-3-(1-dimethylaminopropyl-2-oxy)pyridin-5-yl)-2,4-diaminopyrimidine | $^1$H NMR (400 MHz, DMSO-$d_6$): δ 9.94 (s, NH, 1H), 8.54 (s, Ar-H, 2H), 7.92 (s, Ar-H, 1H), 7.90 (s, Ar-H, 1H), 7.63 (s, Ar-H, 1H), 6.73 (q, J = 4.4 Hz, NH, 1H), 4.69-4.65 (m, CH, 1H), 3.90 (s, $CH_3$, 3H), 2.95 (d, J = 4.4 Hz, $CH_3$, 3H), 2.62-2.58 (m, $CH_2$, 1H), 2.51-2.48 (m, $CH_2$, 1H), 2.24 (s, $CH_3$ × 2, 6H), 1.35 (d, J = 6.0 Hz, $CH_3$, 3H); ESI-MS: m/z = 408 [M + 1]$^+$ |
| Compound 43 | $N^4$-methyl-5-(1-methyl-1H-pyrazol-4-yl)-$N^2$-(2-cyano-3-(N-methylpiperidin-4-yloxy)pyridin-5-yl-2,4-diaminopyrimidine | $^1$H NMR (400 MHz, DMSO-$d_6$): δ 9.91 (s, NH, 1H), 8.53 (s, Ar-H, 1H), 8.47 (s, Ar-H, 1H), 7.91 (s, Ar-H, 1H), 7.90 (s, Ar-H, 1H), 7.62 (s, Ar-H, 1H), 6.73 (q, J = 4.4 Hz, NH, 1H), 4.54 (br, CH, 1H), 3.89 (s, $CH_3$, 3H), 2.94 (d, J = 4.0 Hz, $CH_3$, 3H), 2.58 (br, $CH_2$, 2H), 2.22 (br, $CH_2$, 2H), 2.19 (s, $CH_3$, 3H), 1.97 (br, $CH_2$, 2H), 1.77 (br, $CH_2$, 2H); ESI-MS: mz = 420 [M + 1]$^+$ |

Chk1 Inhibition of the Compounds Disclosed in the Present Invention

With the Saurosporine as a positive control, the Chk1 enzyme inhibitory activity ($IC_{50}$) was evaluated using the ADP-Glo kit. The compound acts on Chk1 protein kinase and inhibits its phosphorylation substrate Cdc25C. The phosphorylation process consumes ATP. After the reaction, ADP-Glo™ Reagent consumes the remaining ATP. The ADP produced during the reaction can be transformed by ADP-Glo Detection Reagent. For ATP, ATP acts as a substrate for the Ultra-Glo™ luciferase catalytic reaction, producing an optical signal. The test compound was dissolved in DMSO to make a 10 mM stock solution and diluted to 12 different concentrations in a certain ratio for testing. In a 384-well plate, add 1 μL of the test compound to each well, 2 μL of 2.5× Chk1 kinase, add 2 μL of 1× buffer to the control group, incubate for 10 min at room temperature, and add 2 μL of 2.5× substrate at 37° C. Incubate for 1 h, stop the reaction by adding 5 μL of ADP-Glo™ Reagent, and incubate for 1 h at 37° C. 10 μL of ADP-Glo Detection Reagent was added, incubated at 37° C. for 30 min, and three parallel wells were set for each sample. Absorbance was measured by luminescence fluorescence microplate reader, and data were calculated using GraphPad Prism 5 software to calculate $IC_{50}$ values.

Inhibitory Activity of the Compounds Disclosed in the Present Invention on Chk1 Kinase

TABLE 2

$IC_{50}$ (μM) of compounds against Chk1 kinase

| Compd. | Chk1 ($IC_{50}$, nM) | Compd. | Chk1 ($IC_{50}$, μM) |
|---|---|---|---|
| 1 | >10 μM | 24 | 6 |
| 2 | >10 μM | 25 | 12 |
| 3 | >10 μM | 26 | 9.5 |
| 4 | >10 μM | 27 | 78.5 |
| 5 | >10 μM | 28 | 9.2 |
| 6 | >10 μM | 29 | 4.7 |
| 7 | >10 μM | 30 | 387.7 |
| 8 | >10 μM | 31 | 14.2 |
| 9 | 4.7 | 32 | 6.9 |
| 10 | 16 | 33 | 4.8 |
| 11 | 14 | 34 | 0.6 |
| 12 | 7.8 | 35 | 6.8 |
| 13 | 5.1 | 36 | 5.3 |
| 14 | 49 | 37 | 1.0 |
| 15 | 25 | 38 | 893.8 |
| 16 | 1.9 | 39 | 17.0 |
| 17 | 8.8 | 40 | 0.4 |
| 18 | 1.8 | 41 | 8.6 |
| 19 | 50 | 42 | 1.1 |
| 20 | >10 μM | 43 | 12 |
| 21 | >10 μM | 44 | 0.7 |
| 22 | >10 μM | 45 | <1 μM |
| 23 | >10 μM | 46 | <1 μM |
| 47 | <1 μM | 48 | <1 μM |
| 49 | <1 μM | 50 | <1 μM |
| Staurosporine | 1.2 | | |

As can be seen from the data in the table, most of the compounds are potent inhibitors of Chk1 protein kinase. The Chk1 inhibitory activity of 24 compounds is comparable to that of the positive compound Staurosporine, and the 5 compounds are superior to the positive control Staurosporine. Therefore, the 2-substituted pyrimidine derivatives used as Chk1 inhibitors of the present invention have broad antitumor application prospects.

Proliferative Inhibitory Activity of the Compounds Disclosed in the Present Invention on Various Tumor Cells Cell lines: human multiple myeloma cells RPMI 8226, human mantle cell lymphoma cells Mino, Jeko-1, human lymphoma cells Romas, human acute monocytic leukemia cells MV-4-11, human breast cancer cells MCF-7 Human lung cancer cell A549, human prostate cancer cell LnCAP, human gastric cancer cell BGC-823, human colon cancer cell HCT116, Colo205, human ovarian cancer cell OVCAR-8 Experimental method: MTS assay for in vitro proliferation of compounds against different tumor cell lines Inhibitory activity ($IC_{50}$).

The cells in the logarithmic growth phase were trypsinized, counted, and seeded at a density of $1\times10^4$ cells/well in a 96-well plate at 100 µL per well in a 37° C. incubator containing 5% $CO_2$ overnight. For the culture, six concentration gradients were set for each compound, and three sets of duplicate wells were set for each concentration. After the addition, the cells were cultured for 72 hours, and 20 µL of MTS was added. After incubating for 2 hours at 37° C., the absorbance at 490 nm (L1) was measured with a SpectraMAX 340 microplate reader. The reference wavelength was 690 nm (L2), and the (L1-L2) value was plotted against the different concentrations of the inhibitor, half of the inhibitory concentration $IC_{50}$ was fitted by the formula.

TABLE 3-1

Inhibition of proliferative of compounds on each tumor cell line

| Cpd. | $IC_{50}$(µM) | | | | |
| --- | --- | --- | --- | --- | --- |
| | RPMI8226 | Mino | Romas | Jeko-1 | MV-4-11 |
| 9 | 3.339 | 0.708 | 0.536 | 0.342 | 0.044 |
| 12 | 3.597 | 0.608 | 0.401 | 0.253 | 0.035 |
| 13 | $NT^b$ | $NT^b$ | $NT^b$ | $NT^b$ | 0.035 |
| 16 | $NT^b$ | $NT^b$ | $NT^b$ | $NT^b$ | 0.107 |
| 17 | 3.290 | 0.495 | 0.348 | 0.117 | 0.050 |
| 18 | $NT^b$ | $NT^b$ | $NT^b$ | $NT^b$ | 0.036 |
| 29 | 2.543 | 0.157 | 0.126 | 0.039 | 0.039 |
| 32 | 8.175 | 0.859 | 0.789 | 0.189 | 0.064 |
| 33 | $NT^b$ | $NT^b$ | $NT^b$ | $NT^b$ | 0.040 |
| 34 | $NT^b$ | $NT^b$ | $NT^b$ | $NT^b$ | 0.044 |
| 35 | 1.273 | 0.647 | 0.356 | 0.339 | 0.053 |
| 36 | 2.493 | 0.956 | 0.649 | 0.548 | 0.072 |
| 37 | 1.578 | 0.419 | 0.292 | 0.103 | 0.022 |
| 40 | 3.781 | 0.923 | 0.874 | 0.309 | 0.101 |
| 41 | 0.945 | 0.473 | 0.119 | 0.094 | 0.034 |
| 42 | 0.814 | 0.227 | 0.218 | 0.137 | 0.092 |
| 44 | 0.448 | 0.128 | 0.117 | 0.084 | 0.023 |

TABLE 3-2

| Cpd. | $IC_{50}$(µM)$^a$ | | | | | | |
| --- | --- | --- | --- | --- | --- | --- | --- |
| | MCF-7 | A549 | LnCAP | BGC-823 | HCT116 | OVCAR-8 | Colo205 |
| 9 | 1.234 | 3.714 | 9.145 | >10 | 5.217 | 0.513 | 2.843 |
| 12 | 2.541 | 2.962 | 7.860 | 9.10.2 | 4.110 | 0.274 | 3.741 |

TABLE 3-2-continued

| Cpd. | $IC_{50}$(µM)$^a$ | | | | | | |
| --- | --- | --- | --- | --- | --- | --- | --- |
| | MCF-7 | A549 | LnCAP | BGC-823 | HCT116 | OVCAR-8 | Colo205 |
| 13 | $NT^b$ | 1.843 | 6.779 | 8.130 | 4.556 | 0.662 | 0.947 |
| 16 | $NT^b$ | 3.474 | 8.776 | >10 | 3.990 | 1.527 | 2.013 |
| 17 | $NT^b$ | 4.238 | >10 | >10 | 1.896 | 0.220 | 0.878 |
| 18 | $NT^b$ | 3.172 | 6.998 | 7.113 | 1.774 | 2.136 | 1.009 |
| 29 | 2.178 | 2.183 | >10 | >10 | 1.225 | 0.329 | 0.624 |
| 32 | $NT^b$ | 5.170 | 5.996 | 7.642 | 4.183 | $NT^b$ | $NT^b$ |
| 33 | $NT^b$ | 3.165 | 5.102 | 6.183 | 2.845 | $NT^b$ | $NT^b$ |
| 34 | $NT^b$ | 3.192 | 4.628 | >10 | 1.779 | 2.110 | 3.760 |
| 35 | 1.008 | 2.162 | 2.173 | 4.810 | 0.980 | 0.789 | 0.663 |
| 36 | $NT^b$ | 5.741 | 4.892 | $NT^b$ | 2.547 | 4.178 | 2.180 |
| 37 | 0.945 | 1.784 | 0.921 | 3.175 | 0.884 | 1.230 | 3.147 |
| 40 | $NT^b$ | 3.512 | 7.164 | $NT^b$ | 2.184 | 2.942 | 5.160 |
| 41 | 1.009 | 2.173 | 2.620 | 5.170 | 1.312 | 1.187 | 0.993 |
| 42 | $NT^b$ | >10 | 5.742 | $NT^b$ | 4.189 | 2.174 | 1.032 |
| 44 | 1.134 | 3.761 | 2.146 | 3.569 | 1.208 | 5.784 | 2.177 |

$^a IC_{50}$: average of three experiments; $^b$not tested.

The Activity of the Compound Disclosed in the Present Invention in Combination with Other Drugs MV 4-11 cells were seeded at 5000/well into 96-well plates. When used in combination, the drug is determined according to the ratio of $IC_{50}$ of the two drugs. The concentration range of each drug is $IC_{20}$~$IC_{80}$ (or ⅛, ¼, ½, 1, 2 and 4 of $IC_{50}$). After 72 hours, cell viability was measured by the addition of MTS reagent, and the inhibition rate Fa was calculated as 100% of the unmedicated group. The Chou-Talalay method was used to analyze the inhibition rate Fa and the corresponding drug concentration into CompuSyn software, and the CI value and Fa-CI curve of single concentration drug were obtained. CI (combination index) is calculated as CI=DA/ICX, A+DB/ICX, B (A, B stands for two different drugs, ICX, A and ICX, B is the growth inhibition rate when the two drugs are used alone. The drug concentration at X, DA and DB are the concentrations of the two drugs when the growth inhibition rate reaches X when the two drugs are combined. The results are shown in FIG. 1. In the FIGURE: CHK1 inhibitor (35); FLT3 inhibitor Crenolanib (Cre), Quizartinib (Qui); Akt inhibitor GSK2141795 (GSK); CI=combination index, according to the judgment method of Soriano et al, 0.9≤CI≤1.1 Superposition effect, 0.8≤CI<0.9 is a low degree synergy, 0.6≤CI<0.8 is a moderate synergy, 0.4≤CI<0.6 is a highly synergistic effect, and 0.2≤CI<4 is a strong synergistic effect.

What is claimed is:

1. A 2-polysubstituted aromatic ring-pyrimidine derivative, which is selected from the group consisting of:
 $N^4$-methyl-5-(1-methyl-1H-pyrazol-4-yl)-$N^2$-(3-(piperidin-4-yloxy)isoxazol-5-yl)-2,4-diaminopyrimidine.

* * * * *